United States Patent
Mulder et al.

(10) Patent No.: US 11,857,614 B2
(45) Date of Patent: Jan. 2, 2024

(54) ENTEROCOCCUS GALLINARUM FLAGELLIN POLYPEPTIDES

(71) Applicant: CJ BIOSCIENCE, INC., Seoul (KR)

(72) Inventors: Imke Elisabeth Mulder, Aberdeen (GB); Emma Raftis, Aberdeen (GB); Emma Elizabeth Clare Hennessy, Aberdeen (GB); Delphine Louise Claudette Laute-Caly, Aberdeen (GB); Philip Cowie, Aberdeen (GB)

(73) Assignee: CJ BIOSCIENCE, INC., Seoul (KR)

( * ) Notice: Subject to any disclaimer, the term of this patent is extended or adjusted under 35 U.S.C. 154(b) by 0 days.

(21) Appl. No.: 17/025,706

(22) Filed: Sep. 18, 2020

(65) Prior Publication Data

US 2021/0138058 A1 May 13, 2021

Related U.S. Application Data

(63) Continuation of application No. PCT/EP2019/056809, filed on Mar. 19, 2019.

(30) Foreign Application Priority Data

| Mar. 19, 2018 | (GB) | 1804384 |
| Jun. 18, 2018 | (EP) | 18178350 |
| Jun. 18, 2018 | (GB) | 1809953 |
| Jul. 20, 2018 | (GB) | 1811900 |
| Jul. 30, 2018 | (GB) | 1812378 |
| Aug. 17, 2018 | (GB) | 1813423 |
| Aug. 17, 2018 | (GB) | 1813444 |
| Oct. 16, 2018 | (GB) | 1816834 |
| Oct. 29, 2018 | (GB) | 1817641 |
| Jan. 29, 2019 | (GB) | 1901199 |
| Jan. 29, 2019 | (GB) | 1901218 |
| Feb. 13, 2019 | (GB) | 1901992 |
| Feb. 13, 2019 | (GB) | 1901993 |

(51) Int. Cl.
- *A61K 39/09* (2006.01)
- *A61K 35/744* (2015.01)
- *A61K 39/00* (2006.01)
- *A61P 37/04* (2006.01)

(52) U.S. Cl.
CPC .......... *A61K 39/09* (2013.01); *A61K 35/744* (2013.01); *A61K 2039/585* (2013.01); *A61P 37/04* (2018.01)

(58) Field of Classification Search
None
See application file for complete search history.

(56) References Cited

U.S. PATENT DOCUMENTS

| 9,839,655 B2 | 12/2017 | Mulder et al. |
| 9,974,815 B2 | 5/2018 | Mulder et al. |
| 10,357,520 B2 | 7/2019 | Mulder et al. |
| 10,610,550 B2 | 4/2020 | Mulder et al. |
| 10,987,387 B2 | 4/2021 | Mulder et al. |
| 11,058,732 B2 | 7/2021 | Mulder et al. |
| 11,419,931 B2 | 8/2022 | Panzica et al. |
| 2004/0009937 A1 | 1/2004 | Chen et al. |
| 2016/0067188 A1 | 3/2016 | Cade et al. |
| 2020/0171098 A1 | 6/2020 | Mulder et al. |
| 2021/0169950 A1 | 6/2021 | Panzica et al. |
| 2022/0257745 A1 | 8/2022 | Panzica et al. |

FOREIGN PATENT DOCUMENTS

| EA | 201401117 A1 | 2/2015 |
| EP | 0904784 A1 | 3/1999 |
| EP | 1958647 A1 | 8/2008 |
| EP | 2133092 A1 | 12/2009 |
| ES | 2408279 A2 | 6/2013 |
| JP | H08259450 A | 10/1996 |
| JP | 2007116991 A | 5/2007 |
| JP | 2017506212 A | 3/2017 |
| WO | WO-03046580 A1 | 6/2003 |
| WO | WO-2006110603 A1 | 10/2006 |
| WO | WO-2008114889 A1 | 9/2008 |
| WO | WO-2008144889 A1 | 12/2008 |
| WO | WO-2009130618 A2 | 10/2009 |
| WO | WO-2011044246 A1 | 4/2011 |
| WO | WO-2012097012 A1 | 7/2012 |
| WO | WO-2013008038 A2 | 1/2013 |
| WO | WO-2013008039 A2 | 1/2013 |
| WO | WO-2013050792 A1 | 4/2013 |
| WO | WO-2014043593 A2 | 3/2014 |
| WO | WO-2014167338 A1 | 10/2014 |
| WO | WO-2015121863 A1 | 8/2015 |
| WO | WO-2017085520 A1 | 5/2017 |
| WO | WO-2019010255 A1 | 1/2019 |
| WO | WO-2019030411 A1 | 2/2019 |
| WO | WO-2019180000 A1 | 9/2019 |
| WO | WO-2019180051 A1 | 9/2019 |

OTHER PUBLICATIONS

Bowie et al. (Science, 1990, 257:1306-1310).*
Colman Res. Immunology (Jan. 1994, vol. 145, pp. 33-36).*
Greenspan et al. (Nature Biotechnology 7: 936-937, 1999).*
Bork (Genome Research, 2000, 10:398-400).*
Daillere, Romain et al., *Enterococcus hirae* and *Barnesiella intestinihominis* Facilitate Cyclophosphamide-Induced Therapeutic Immunomodulatory Effects, Immunity, 2016, vol. 45, pp. 931-943.
Nami, Yousef et al., The Prophylactic Effect of Probiotic *Enterococcus lactis* IW5 against Different Human Cancer Cells, Frontiers in Microbiology, 2015, vol. 6, Article 1317, pp. 1-11.

(Continued)

*Primary Examiner* — Robert A Zeman

(74) *Attorney, Agent, or Firm* — Morgan, Lewis & Bockius LLP

(57) ABSTRACT

The invention provides compositions comprising flagellin polypeptides from bacterial strains and the use of such compositions in the treatment of disease.

11 Claims, 35 Drawing Sheets

Specification includes a Sequence Listing.

(56) References Cited

OTHER PUBLICATIONS

Sorroza, Lita et al., A Probiotic Potential of *Enterococcus gallinarum* against *Vibrio anguillarum* Infection, Fish Pathology,2013, vol. 48, No. 1, pp. 9-12.

Theppangna, Watthana et al., Inhibitory Effects of *Enterococcus* Strains Obtained from a Probiotic Product on In Vitro Growth of *Salmonella enterica* Serovar Enteritidis Strain IFO3313, Journal of Food Protections, 2006, vol. 69, No. 9, pp. 2258-2262.

Arenberg, et al., Interferon-y-inducible Protein10 (IP-10) Is an Angiostatic Factor That Inhibits Human Non-small Cell Lung Cancer (NSCLC) Tumorigenesis and Spontaneous Metastases. 1996. J. Exp.Med.184:981-92. Sep. 1, 1996.

Atarashi et al. Induction of colonic regulatory T cells by indigenous Clostridium species. Science 331(6015):337-341 (2011).Epub Dec. 23, 2010.

Attmannspacher Ursula et al., FliL isessential for swarming: motor rotation in absence of FliL fractures theflagellar rod in swarmer cells of *Salmonella enterica* (2008), Mol Microbiol 68,328-341.

Aw, Danielle et al."Immunosenescence: emerging challenges for an ageing population." Immunology vol. 120,4 (2007): 435-46. doi:10. 1111/j.1365-2567.2007.02555.x.

Azad, M.B. et al., Probiotic supplementation during pregnancy or infancy for the prevention of asthma and wheeze: systematic review and meta-analysis BMJ 2013; 347 :f6471, Dec. 4, 2013.

Beatson SA, et al., "Variation in bacterial flagellins: from sequence to structure" Trends in Microbiology. Apr. 2006;14(4):151-155. DOI: 10.1016/j.tim.2006.02.008.

Bektas, Arsun et al. "Human T cell immunosenescence and inflammation in aging." Journal of leukocyte biology vol. 102,4 (2017): 977-988. doi:10.1189/jlb.3RI0716-335R.

Berthoud et al., "MIG (CXCL9) is a more sensitive measure than IFN-γ of vaccine induced T-cell responses in volunteers receiving investigated malaria vaccines"(2009) J Immunol Methods 340(1)33-41.

Bettelli E, Carrier Y, Gao W, Korn T, Strom TB, Oukka M, Weiner HL, Kuchroo VK. Reciprocal developmental pathways for the generation of pathogenic effector TH17 and regulatory T cells. Nature. May 11, 2006;441(7090):235-8. doi: 10.1038/nature04753. Epub Apr. 30, 2006. PMID: 16648838.

Bloch F, et al., "Production of TNF-alpha ex vivo is predictive of an immune response to flu vaccination in a frail elderly population", Eur Cytokine Netw. Sep. 1, 2016;27(3):63-67. English.doi: 10.1684/ ecn.2016.0378. PMID: 27910810.

Bohnhorst, J., Rasmussen, T., Moen, S et al. Toll-like receptors mediate proliferation and survival of multiple myeloma cells. Leukemia 20, 1138-1144 (2006). https://doi.org/10.1038/sj.leu. 2404225.

Brackett et al., "Toll-like receptor-5 agonist, entolimod, suppresses metastasis and induces immunity by stimulating an NK-dendritic-CD8+T-cell axis", (2016) PNAS, E874-E883.

Cai, Zhenyu et al., Activation of Toll-like Receptor 5 on Breast Cancer Cells by Flagellin Suppresses CellProliferation and Tumor Growth (2011) Cancer Res. 71(7): 2466-2475, DOI:10.1158/0008-5472.CAN-Oct. 1993 Published Apr. 2011.

Chan, Jason R et al. "IL-23 stimulates epidermal hyperplasia via TNF and IL-20R2-dependent mechanisms with implications for psoriasis pathogenesis." The Journal of experimental medicine vol. 203,12 (2006): 2577-87. doi:10.1084/jem.20060244.

Chen D.K. et al. "Evaluation of D-xyloseand 1% methyl-alpha-D-glucopyranoside Fermentation Tests for Distinguishing EnterococcusGallinarum From Enterococcus Faecium". J. Clin. Microbiol. Oct. 2000, 38(10): 3652-3655;PMID: 11015378.

Chung et al. 'Microbiota-stimulated immune mechanisms to maintain gut homeostasis.' Current Opinion in Immunology. 2010, vol. 22, No. 4, pp. 455-460. Epub Jul. 23, 2010.

Coffman, Robert L et al. "Vaccine adjuvants: putting innate immunity to work." Immunity vol. 33,4 (2010): 492-503. doi:10.1016/j. immuni.2010.10.002.

Darnton, Nicholas C, and Howard C Berg. "Bacterial flagella are firmly anchored." Journal of bacteriology vol. 190,24 (2008): 8223-4. doi:10.1128/JB.00908-08.

Datanase UniProt [Online] Jan. 25, 2012(Jan. 25, 2012), "Rec Name:Full=Flagellin {ECO:0000256|RuleBase:RU362073};", XP002791697, retrieved from EBI accession No. UNIPROT:G5IWG8, Database accession No. G5IWG8.

Didierlaurent AM, et al., Enhancement of adaptive immunity by the human vaccine adjuvant AS01 depends on activated dendritic cells. J Immunol. Aug. 15, 2014;193(4):1920-30. doi: 10.4049/jimmunol. 1400948. Epub Jul. 14, 2014. PMID: 25024381.

Eckburg, PB. et al., Diversity of the human intestinal microbial flora. Science. Jun. 10, 2005;308(5728):1635-8. Epub Apr. 14, 2005.

Eurasian Search Report dated May 23, 2020 for Application Serial No. 202090107 (8 pages).

Fernández-Ruiz M, et al. "Baseline serum interleukin-6 to interleukin-2 ratio is associated with the response to seasonal trivalent influenza vaccine in solid organ transplant recipients", Vaccine.Dec. 16, 2015;33(51):7176-7182. doi: 10.1016/j.vaccine.2015.10.134. Epub Nov. 10, 2015. PMID: 26555352.

Filipe M de Melo et al. "Anti-metastatic immunotherapy based on mucosal administration of flagellin and immunomodulatory P10",(2015)Immunology and Cell Biology 93, 86-98.

Fülöp T, Dupuis G, Witkowski JM, Larbi A. The Role of Immunosenescence in the Development of Age-Related Diseases. Rev Invest Clin. Mar.-Apr. 2016 68(2):84-91. PMID: 27103044.

Fraietta, Joseph et al. Jan. (2018). Determinants of response and resistance to CD19 chimeric antigen receptor (CAR) T cell therapy of chronic lymphocytic leukemia. Nature Medicine. 24.10.1038/ s41591-018-0010-1.

Frank, D. et al., Molecular-phylogenetic characterization of microbial community imbalances in human inflammatory bowel diseases. 2007. PNAS. 104(34):13780-5.online Aug. 15, 2007.

Fulop, Tamas et al., "Immunosenescence and Cancer "(2013) Critical Reviews in Oncogenesis 2013;18(6):489-513.

Fulop, Tamas et al. "Immunosenescence and Inflamm-Aging As Two Sides of the Same Coin: Friends or Foes?." Frontiers in immunology vol. 8 1960. Jan. 10, 2018, doi:10.3389/fimmu.2017. 01960.

Gaboriau-Routhiau et al. 'The key role of segmented filamentous bacteria in the coordinated maturation of gut helper T cell responses.' Immunity. 2009, vol. 31, No. 4, pp. 677-689.

Gaur and Aggarwal, Regulation of proliferation, survival and apoptosis by members of the TNF superfamily* (2003).Biochem Pharmacol.; 66(8):1403-8.

GenBank Accession No. KC456574.1 (May 3, 2013) Enterococcus casseliflavus strain ALK061 16S ribosomal RNAgene, partial sequence [Enterococcus casseliflavus], May 23, 2020:https://www.ncbi.nlm. nih.govinuccore/KC456574.1.

Geuking et al. 'Intestinal bacterial colonization induces mutualistic regulatory T cell responses.' Immunity. 2011, vol. 34, No. 5, pp. 794-806. Epub May 19, 2011.

Gewirtz et al. (2001) Cutting edge: bacterial flagellin activates basolaterally expressed TLR5 to induce epithelial proinflammatory gene expression. The Journal of Immunology. 167:(4)1882-1885.

Glenn, Justin D, and Katharine A Whartenby. "Mesenchymal stem cells: Emerging mechanisms of immunomodulation and therapy." World journal of stem cells vol. 6,5 (2014): 526-39. doi:10.4252/ wjsc.v6.i5.526.

Goldin, B.R. et al., Clinical indications for probiotics: an overview. Clin Infect Dis. Feb. 1, 2008;46 Suppl 2:S96-100; discussion S144-51. doi: 10.1086/523333.

Haabeth et al. A model for cancer-suppressive inflammation. (2012) OncoImmunology 1(1):1146-1152.

Hajam,I., Dar, P., Shahnawaz, I. et al. Bacterial flagellin—a potent immunomodulatory agent. Exp Mol Med 49, e373(2017). https:// doi.org/10.1038/emm.2017.172.

Heng, Boon Chin et al., Strategies for directing the differentiation of stem cells into the cardiomyogenic lineage in vitro (2004) Cardiovasc Res. Apr. 1, 2004;62(1):34-42.

(56) References Cited

OTHER PUBLICATIONS

International Preliminary Report on Patentability dated Sep. 11, 2020 for International Application Serial No. PCT/EP2019/056809, (16 pages).
Ivanov et al. 'Induction of intestinal Th17cells by segmented filamentous bacteria.' Cell. 2009, vol. 139, No. 3, pp. 485-498. available in PMC Apr. 30, 2010.
Jacchieri, Saul G, Structural Study of Binding of Flagellin by Toll-Like Receptor 5, Aug. 2003, Journal of Bacteriology 185(14):4243-7, DOI: 10.1128/JB.185.14.4243-4247.2003.
Kang, S. et al. (2010) "Dysbiosis of fecal microbiota inCrohn's disease patients as revealed by a custom phylogenetic microarray,"Inflammatory BowelDiseases. Dec. 2010; 16(12):2034-2042. doi: 10.1002/ibd.21319.
Kawai and Akira, "Signaling to NF-kB by Toll-like receptors" (2007) Trends in Molecular Medicine 13, 11, 460-469.
Kelley, L., Mezulis, S., Yates, C. et al. The Phyre2 web portal for protein modeling, prediction and analysis. NatProtoc 10, 845-858 (2015). https://doi.org/10.1038/nprot.2015.053.
Kinnebrew, Melissa A et al. "Bacterial flagellin stimulates Toll-like receptor 5-dependent defense against vancomycin-resistant Enterococcus infection." The Journal of infectious diseases vol. 201,4 (2010): 534-43. doi:10.1086/650203.
Klein, G."Taxonomy, Ecology and Antibiotic Resistance of Enterococci From Food and the Gastro-Intestinal Tract". Int.J. Food Microbiol. 2003, 88(2-3): 123-131; PMID: 14596985. Dec. 1, 2003.
Knudsen, Niels Peter H et al. "Different human vaccine adjuvants promote distinct antigen-independent immunological signatures tailored to different pathogens." Scientific reports vol. 6 19570. Jan. 21, 2016, doi:10.1038/srep19570.
Laukova A. et al. "Characteristics of Enterococci and Staphylococci Isolated From the Crop and Caecum of Japanese Quails Exposed to Microgravity Conditions". Vet. Med. (Praha).Oct. 1995, 40(10): 317-321,PMID: 8659081.
Laukova A. "The Effect of Culture Media on Bacteriocin Production in Various Strains of Bacteria".Vet. Med. (Praha). 1992, 37(12): 661-666; PMID: 1297243.
Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24): 7011-7018.
Leal, I S et al. "Interleukin-6 regulates the phenotype of the immune response to a tuberculosis subunit vaccine." Immunology vol. 103,3 (2001): 375-81. doi:10.1046/j.1365-2567.2001.01244.x.
Leigh, Nicholas D et al. "A flagellin-derived toll-like receptor 5 agonist stimulates cytotoxic lymphocyte-mediated tumor immunity." PloS one vol. 9,1 e85587. Jan. 14, 2014, doi:10.1371/journal.pone.0085587.
Lejeune et al. Efficiency of Recombinant Human TNF in Human Cancer Therapy. Cancer Immun. 6:6 (2006).
Li et al., "Aluminum Hydroxide Adjuvants Activate Caspase-1 and Induce IL-1β andIL-18 Release" (2007) J Immunol, 178(8),5271-5276.
Lim, Jae Sung et al. "Flagellin-dependent TLR5/caveolin-1 as a promising immune activator in immunosenescence." Aging cell vol. 14,5 (2015): 907-15. doi:10.1111/acel.12383.
Lu, Yuan, and James R Swartz. "Functional properties of flagellin as a stimulator of innate immunity." Scientific reports vol. 6 18379. Jan. 12, 2016, doi:10.1038/srep18379.
Machiels, K., A decrease of the butyrate-producing species Roseburia hominis and Faecalibacterium prausnitzii defines dysbiosis in patients with ulcerative colitis. Gut. Aug. 2014;63(8):1275-83. doi: 10.1136/gutjnl-2013-304833. Epub Sep. 10, 2013.
Macpherson, AJ et al., IgA responses in the intestinal mucosa against pathogenic and non-pathogenic microorganisms. Oct. 2001. 3(12). 1021-1035.
Macpherson, AJ., et al., The functions of mucosal T cells in containing the indigenous commensal flora of the intestine. Cell Mol Life Sci. Dec. 2002;59(12):2088-96.

Macpherson et al. 'IgA adaptation to the presence of commensal bacteria in the intestine.' Gut-Associated Lymphoid Tissues. Springer Berlin Heidelberg, 2006. 117-136.
Martinon, Fabio et al., The Inflammasome: A Molecular Platform Triggering Activation of Inflammatory Caspases and Processing of proIL-β, (2002) Mol Cell .; 10(2):417-26.
Mazmanian, SK., An immunomodulatory molecule of symbiotic bacteria directs maturation of the host immune system. Cell. Jul. 15, 2005;122(1):107-18.
Mohanty, Subhasis et al. "Prolonged proinflammatory cytokine production in monocytes modulated by interleukin 10 after influenza vaccination in older adults." The Journal of infectious diseases vol. 211,7 (2015): 1174-84. doi:10.1093/infdis/jiu573.
Morel S, et al. "Adjuvant System AS03 containing a-tocopherol modulates innate immune response and leads to improved adaptive immunity", Vaccine. Mar. 16, 2011;29(13):2461-73. doi: 10.1016/j.vaccine.2011.01.011. Epub Jan. 20, 2011. PMID:21256188.
Mori, Andres et al., "The vaccine adjuvant alum inhibits IL-12 by promoting PI3 kinase signaling while chitosan does not inhibit IL-12 and enhances Th1 and Th17 responses" (2012), Eur J Immunol42, 2709-2719.
Murphy, Craig A et al. "Divergent pro- and anti inflammatory roles for IL-23 and IL-12 in joint autoimmune inflammation." The Journal of experimental medicine vol. 198, 12 (2003): 1951-7. doi:10.1084/jem.20030896.
Nutsch et al., T cell tolerance and immunity to commensal bacteria. Current Opinion in Immunology. Aug. 2012; 24 (4):385-391. Epub May 19, 2012.
Okamoto et al., "Toll-like Receptors (TLRs) are expressed by myeloid leukaemia cell lines, but fail to trigger differentiation in response to the respective TLR ligands" (2009) British Journal of Haematology, 147, 582-590.
Okino, H et al. Release of flagellar filament-hook-rod complex by a *Salmonella typhimurium* mutant defective in the M ring of the basalbody (1989) Journal of Bacteriology 171(4):2075-82, DOI:10.1128/jb.171.4.2075-2082.1989.
Pace et al. Macrophage activation: Priming activity from a T-cell hybridoma is attributable to interferon. (1983) PNAS. 80:3782-6.
Palmer, Kelli L. et al., "Comparative Genomics of Enterococci: Variation in Enterococcus faecalis, Clade Structure inE. faecium, and Defining Characteristics of E. gallinarum and E. casseliflavus",. mBio, (2012) vol. 3 Issue 1 e00318-11.
Park, Matthew K et al., The CXC Chemokine Murine Monokine Induced by IFN-γ (CXC Chemokine Ligand 9) Is Made by APCs, Targets Lymphocytes Including Activated B Cells, and Supports Antibody Responses to a Bacterial Pathogen In Vivo, J Immunol Aug. 1, 2002, 169 (3)1433-1443; DOI: https://doi.org/10.4049/jimmunol.169.3.1433.
Pettersen EF et al., UCSF Chimera—Visualization System for Exploratory Research and Analysis (2004), Journal of Computational Chemistry 25(13):1605-12.
Porte, Rémi et al. "A Toll-Like Receptor 5 Agonist Improves the Efficacy of Antibiotics in Treatment of Primary and Influenza Virus-Associated Pneumococcal Mouse Infections." Antimicrobial agents and chemotherapy vol. 59,10 (2015): 6064-72. doi:10.1128/AAC.01210-15.
Prakash, et al., Complete genome sequences of rat and mouse segmented filamentous bacteria, a potent inducer of th17 cell differentiation. Cell Host & Microbe. Sep. 2011;10(3):273-284.
Rakoff-Nahoum S, Medzhitov R. Toll-like receptors and cancer. Nat Rev Cancer. Jan. 2009;9(1):57-63. doi:10.1038/nrc2541. Epub Dec. 4, 2008. PMID: 19052556.
Rashidi, Armin et al. "Pretransplant Gut Colonization with Intrinsically Vancomycin-Resistant Enterococci (E. gallinarum and E. casseliflavus) and Outcomes of Allogeneic Hematopoietic Cell Transplantation." Biology of blood and marrow transplantation : journal of the American Society for Blood and Marrow Transplantation vol. 24,6 (2018): 1260-1263. doi:10.1016/j.bbmt.2018.01.025.
Ren, Ke, and Richard Torres. "Role of interleukin-1 beta during pain and inflammation." Brain research reviews vol. 60,1 (2009): 57-64. doi:10.1016/j.brainresrev.2008.12.020.

(56) References Cited

OTHER PUBLICATIONS

Rhee et al. , Toll-Like Receptor 5 Engagement Modulates Tumor Development and Growth in a Mouse Xenograft Model of Human Colon Cancer. Gastroenterology. Aug. 2008;135(2):518- 528, Epub Apr. 23, 2008.
Roman, Lorena et al: "The effect of probiotic Enterococcus gallinarum L-1 on the innate immune parameters of outstanding species to marine aquaculture", Journal of Applied Animal Research, vol. 43, No. 2, Jul. 18, 2014(Jul. 18, 2014), pp. 177-183, XP055525525,IN, ISSN: 0971-2119, DOI:10.1080/09712119.2014. 928635.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Sczesnak, et al., The genome of th17 cell-inducing segmented filamentous bacteria reveals extensive auxotrophy and adaptations to the intestinal environment. Cell Host Microbe. Sep. 2011;10 (3):260-272.
Sfondrini, Lucia et al., AntitumorActivity of the TLR-5 Ligand Flagellin in Mouse Models of Cancer (2006),J Immunol Jun. 1, 2006, 176 (11)6624-6630; DOI: https://doi.org/10.4049/jimmunol. 176.11.6624.
Sgadari, C. et al., Interferon-inducible protein-10 identified as a mediator of tumor necrosis in vivo. (1996) PNAS. 93:13791-6.
Sgadari et al. Mig, the Monokine Induced By Interferon-g, Promotes Tumor Necrosis In Vivo. (1997) Blood. 89:2635-43.Nov. 26, 1996.
She et al., Investigation of the Utility of Complementary Electrochemical Detection Techniques to Examine the in Vitro Affinity of Bacterial Flagellins for a Toll-Like Receptor 5 Biosensor (2015)Anal. Chem., 87 (8), pp. 4218-4224.
Shepard et al., B. D. & Gilmore, M. S. In Electroporation and efficient transformation of Enterococcus faecalis grown in high concentrations of glycinein Methods in molecular biology: vol. 47: Electroporation protocols for microorganisms vol. 47 (ed J. A. Nickoloff) 217-226 (Humana Press Inc., 1995).
Smith and Waterman, "Comparison of biosequences", Advances in Applied Mathematics, vol. 2, Issue 4, Dec. 1981, pp. 482-489.
Smith KD, et al. Toll-like receptor 5 recognizes a conserved site on flagellin required for protofilament formation and bacterial motility. Nat Immunol. Dec. 2003;4(12):1247-53. doi: 10.1038/ni1011. Epub Nov. 16, 2003. Erratum in: Nat Immunol. Apr. 2004;5(4):451. PMID: 14625549.
Song, W., Jeon, Y., Namgung, B et al. A conserved TLR5 binding and activation hotspot on flagellin. Sci Rep 7, 40878 (2017). https://doi.org/10.1038/srep40878.
Spor, A. et al., Unravelling the effects of the environment and host genotype on the gut microbiome. Nat Rev Microbiol. Apr. 2011;9(4):279-90. doi: 10.1038/nrmicro2540.
Steiner, Theodore S., How Flagellin and Toll-Like Receptor 5 Contribute to Enteric Infection (2007). Infection and Immunity 75, 545-552, DOI: 10.1128/IAI.01506-06.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Su, Baowei et al., The effects of IL-6 and TNF-alpha as molecular adjuvants on immune responses to FMDV and maturation of dendritic cells by DNA vaccination. (2008) Vaccine. 26. 5111-22. 10.1016/j.vaccine.2008.03.089.
Sun et al., Posttranslational Modification of Flagellin FlaB in Shewanella oneidensis (2013)J Bacteriol. 195(11):2550-61.
Tanaka, Toshio et al. "IL-6 in inflammation, immunity, and disease." Cold Spring Harbor perspectives in biology vol. 6,10 a016295. Sep. 4, 2014, doi:10.1101/cshperspect.a016295.
Toshkov, Ilia A et al. "Mitigation of Radiation-Induced Epithelial Damage by the TLR5 Agonist Entolimod in a Mouse Model of Fractionated Head and Neck Irradiation." Radiation research vol. 187,5 (2017): 570-580. doi:10.1667/RR14514.1.

Turner, Linda et al. "Visualizing Flagella while Tracking Bacteria." Biophysical journal vol. 111,3 (2016): 630-639. doi:10.1016/j.bpj. 2016.05.053.
Uematsu, S., Jang, M., Chevrier, N et al. Detection of pathogenic intestinal bacteria by Toll-like receptor 5 on intestinal CD11c+ lamina propria cells. Nat Immunol 7, 868-874 (2006).https://doi. org/10.1038/ni1362.
Vijay-Kumar et al., Flagellin Treatment Protects against Chemicals, Bacteria, Viruses, and Radiation. The Journal of Immunology. 2008;180(12):8280-8285.
Wang, Xia, and Yong Lin. "Tumor necrosis factor and cancer, buddies or foes ?. " Acta pharmacologica Sinica vol. 29,11 (2008): 1275-88. doi:10.1111/j.1745-7254.2008.00889.x.
Weinberger B. Adjuvant strategies to improve vaccination of the elderly population. Curr Opin Pharmacol. Aug. 2018;41:34-41. doi: 10.1016/j.coph.2018.03.014. Epub Apr. 17, 2018. PMID: 29677646.
Yonekura K, et al., "Complete atomic model of the bacterial flagellar filament by electron cryomicroscopy", Nature. Aug. 7, 2003;424(6949):643-50. doi:10.1038/nature01830. PMID: 12904785.
Yoon et al. Structural Basis of TLR5-Flagellin Recognition and Signaling, (2013). NIH Public Access 335,859-864.
Zheng, Jin Hai, "Two-step enhanced cancer immunotherapy with engineered Salmonella typhimurium secreting heterologous flagellin", Science Translational Medicine Feb. 8, 2017:vol. 9, Issue 376,eaak9537, DOI: 10.1126/scitranslmed.aak9537.
Zhou, Qing et al. "Program death-1 signaling and regulatory T cells collaborate to resist the function of adoptively transferred cytotoxic T lymphocytes in advanced acute myeloid leukemia." Blood vol. 116,14 (2010): 2484-93. doi:10.1182/blood-2010-03-275446.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Patel., R. et al., Determination of 16S rRNA sequences of enterococci and application to species identification of nonmotile enterococcus gallinarum isolates. Journal of clinical microbiology, 1998; 36(11):3399-3407.
Sivieri, K. et al., Probiotic enterococcus faecium CRL 183 inhibit chemically induced colon cancer in male wistar rats. Eur Food Res Technol. 2008; 228:231-237.
Vetrovsky, T. and Baldrian, P., The variability of the 16S rRNA gene in bacterial genomes and its consequences for bacterial community analyses. Plos One. Feb. 2013; 8(2): e57923.
Jul. 26, 2021 Non-Final Office Action U.S. Appl. No. 17/024,628.
Aiello, Anna et al., "Immunosenescence and its Hallmarks: How to Opposed Aging Strategically? A Review of Potential Options for Therapeutic Intervention", Frontiers in Immunology, Sep. 2019, vol. 10, Article 2247, pp. 1-19.
Bertram, J. et al. Establishment of a cloned line of Lewis lung carcinoma cells adapted to cell culture. (1980) Cancer let. 11:63-73.
Collins, M.D., et al., Enterococcus avium nom.rev., comb. nov .; E. casseliflavus nom. rev., comb. nov .; E. durans nom. rev., comb. nov .; E. gallinarum comb. nov .; and E. malodoratus sp. nov. (1984) Int JSyst Evol Microbiol. 34: 220-223. First Published: Apr. 1, 1984.irst Published: Apr. 1, 1984.
Darlington, G.J., Liver Cell Lines. (1987) Meth Enzymol. 151:19-38.
"Disease or Condition" ("Immunosenescence")Search List retrieved from Home—Clinical Trials.gov (https://clinicaltrials.gov/) on May 7, 2021.
"Immunosenescence" Search List retrieved from PubMed (https:// pubmed.ncbi.nlm.nih.gov/) on May 6, 2021.
International Search Report dated Jun. 18, 2019 for International Application Serial No. PCT/EP2019/056894, (5 pages).
Kailasapathy, K. Microencapsulation of Probiotic Bacteria: Technology and Potential Applications. Curr. Issues Intest. Microbiol. (2002) 3: 39-48.
Leslie, et al., Trehalose and sucrose protect both membranes and proteins in intact bacteria during drying. (1995) Appl. Environ. Microbiol. 61, 3592-3597.
Masco, L., et al., Identification of Bifidobacterium Species Using rep-PCR Fingerprinting. Systematic and Applied Microbiology 26(4):557-63 · Nov. 2003.

(56) References Cited

OTHER PUBLICATIONS

Mitropoulou, G et al. Immobilization Technologies in Probiotic Food Production. (2013) Journal Nutr Metab. (2013) 716861.
Miyamoto-Shinohara et al. Survival of freeze-dried bacteria. J Gen Appl Microbiol 54(1):9-24 (2008).
Official Journal of the European Union, Directive 2010/63/EU of the European Parliament and of the Council of Sep. 22, 2010 on the protection of animals used for scientific purposes, Oct. 20, 2010, i. 276/33, pp. 1-47.
Rockwell, S.C et al., Characteristics of a Serially Transplanted Mouse Mammary Tumor and Its Tissue-Culture-Adapted Derivative. (1972) J Natl Cancer Inst. 49:735-49.
Simpson-Herren, L. et al., Kinetic parameters and growth curves for experimental tumor systems. Cancer Chemother Rep. Jun. 1970;54(3):143-74.
Srutkova, D. et al., Efficiency of PCR-based methods in discriminating Bifidobacterium longum ssp. longum and Bifidobacterium longum ssp. infantis strains of human origin.J Microbiol Methods. Oct. 2011;87(1):10-6. doi: 10.1016/j.mimet.2011.06.014. Epub Jul. 2, 2011.
Strobel, H.J. Basic laboratory culture methods for anaerobic bacteria. Methods Mol Biol. 2009;581:247-61. doi: 10.1007/978-1-60761-214-8_16.
Van den Bogert, Bartholomeus et al. "Immunomodulatory Properties of *Streptococcus* and *Veillonella* Isolates from the Human Small Intestine Microbiota" PloS one, vol. 9, No. 12, p. e114277, Dec. 5, 2014, doi:10.1371/journal.pone.0114277.
Workman et al. Guidelines for the welfare and use of animals in cancer research (2010) Br. J. Cancer. 102:1555-77.
Olafsdottir, Thorunn et al., "Molecular signatures of vaccine adjuvants", Vaccine 33(40)5302-5307.
Sha, Ping. "Analysis on the distribution and drug resistance of Enterococcus nosocomial infection in 2011-2012." Journal of Chengde Medical College 30.6(2013):2.
Anonymous: "UPI00038B669E| UniParc|UniProt", Oct. 16, 2013, retrieved from the Internet: URL: https://www.uniprot.org/uniparc/UPI00038B669E/entry?facets=taxonIds:1316414 [retrieved on Feb. 10, 2023].
International Preliminary Report on Patentability dated Sep. 22, 2020 for International Application Serial No. PCT/EP2019/056894.
Jamet A. et al., "The Enterococcus faecalis virulence factor ElrA interacts with the human Four-and-a-Half LIM Domains Protein 2 ", Scientific Reports, 2017, vol. 7, No. 4581, pp. 1-13.
NCBI Reference Sequence: wp_005472956.1, Multispecies: flagellin [Enterococcus], Jun. 20, 2022 National Center for Biotechnology Information, NIH, 2 pages.
NCBI Reference Sequence: WP_081131820, flagellin [Enterococcus gallinarum], Jun. 20, 2022 National Center for Biotechnology Information, NIH, 2 pages.
Wang et al., "Infant intestinal Enterococcus faecalis down-regulates inflammatory responses in human intestinal cell lines", World J. Gastroentrol, 2008, vol. 14 No. 7, pp. 1067-1076.
Wang, X. et al., "Enterococcus faecalis Induces Aneuploidy and Tetraploidy in Colonic Epithelial Cells Through a Bystander Effect", Cancer Res., 2008, vol. 68, No. 23, pp. 9909-9917.
GenBank Accession No. WP 021148989.1 (2013-09-21) "Flagellin protein FlaA [Enterococcus sp. HSIEG1]", 1 page.
GenBank Accession No. WP 103300682 (2018-01-31) "flagellin [Enterococcus gallinarum]", 1 page.

\* cited by examiner

Cross-section view of the flagellar filament

Top view of the flagellar filament

FIG. 3B

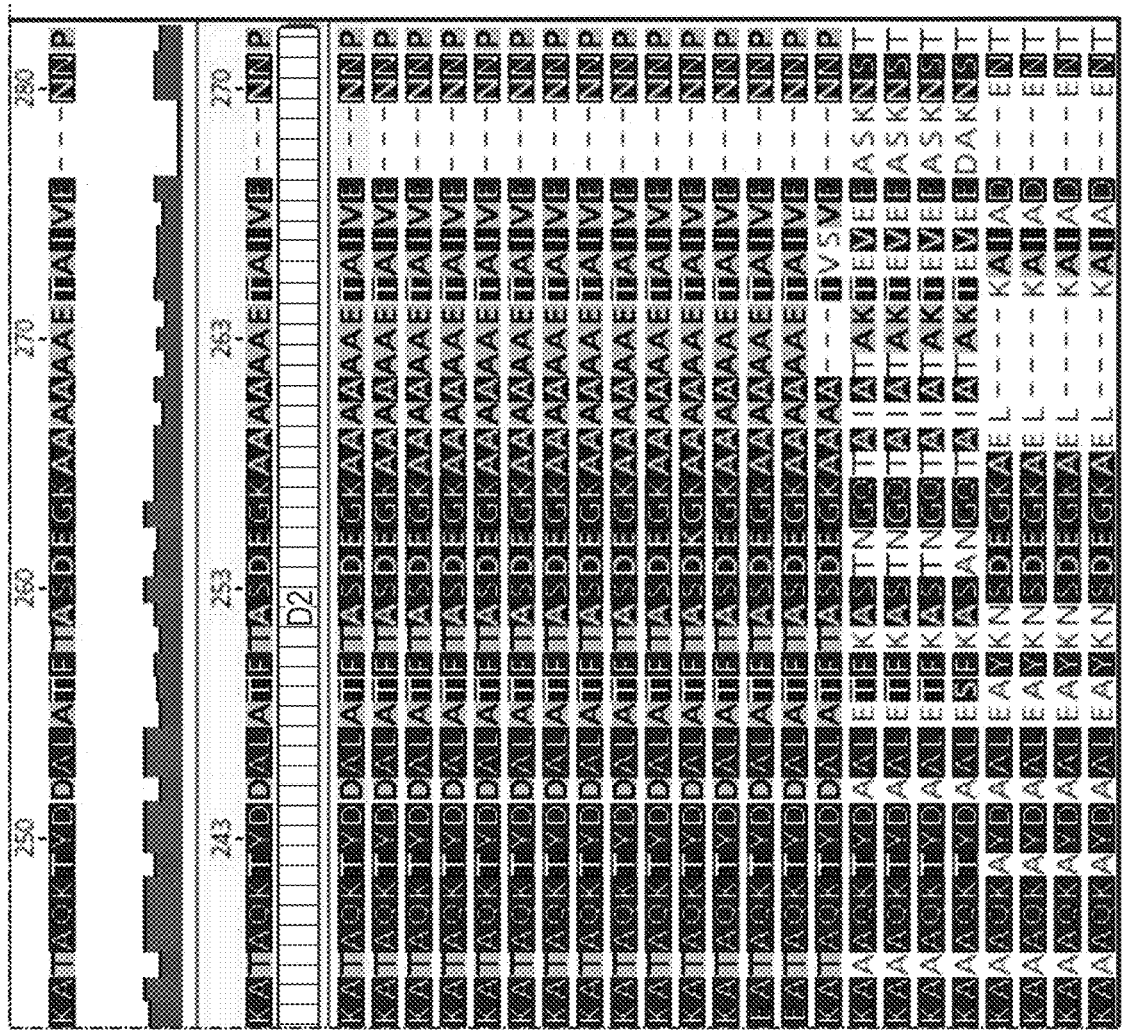

Flagellar assembly

MRx0518 flagellin (FliC$_{MRx0518}$) structure prediction

Salmonella typhimurium flagellin protein structure

FIG. 14
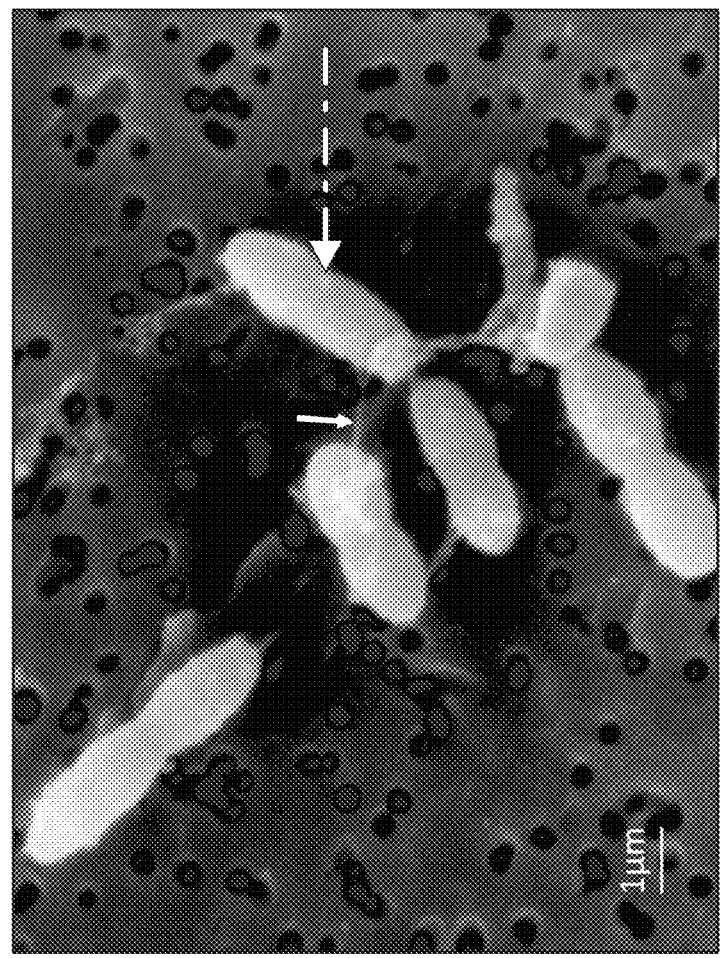
Scanning electron micrograph
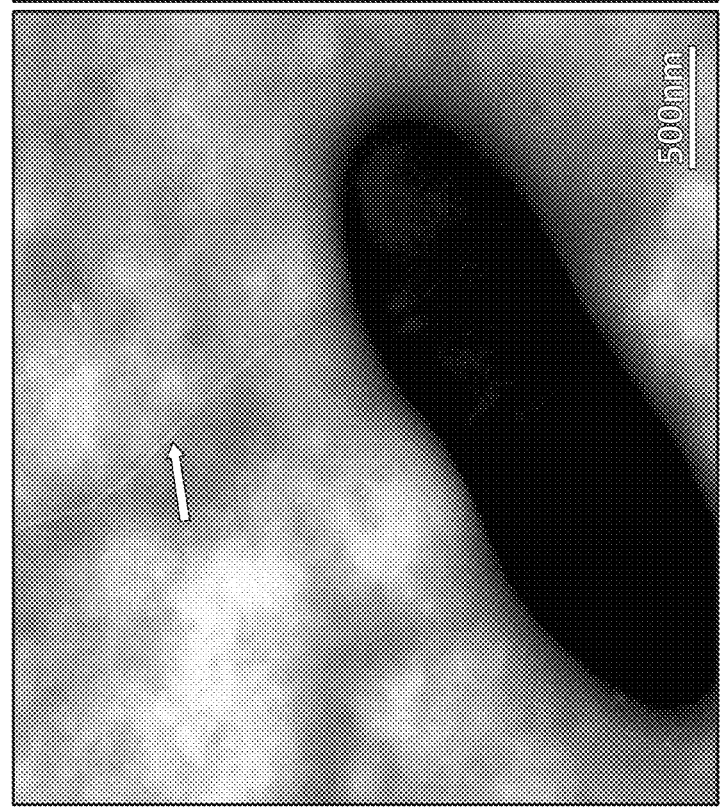
Transmission electron micrograph

```
MRx0518    MRINTNVSALNTYSRLTAANASKSNSLSKLSSGLRINKAGDDAAGLAISEKMKGQIGGLS  60
DSM100110  MRINTNVSALNTYSRLTAANASKSNSLSKLSSGMRINKAGDDAAGLAISEKMKGQIGGLS  60
           ********************************:***************************

MRx0518    QAKSNAQDGISLIQTAEGALNETHSILGRMRDLAVQSSNGTLSDDDRSAINKEYTALSDE  120
DSM100110  QAKSNAQDGISLIQTAEGALNETHSILGRMRDLAVQSSNGTLSDDREAISKEFSALSDE  120
           *********************************************:.**:**:;*****

MRx0518    IDRIRDTTEFNTKSLLTG-EGDDAKSFTFQIGANANQTMSVSITNMSSTALKVKGLDLTQ  179
DSM100110  IDRISTTEFNTKSLLKGGESGEKASFFQIGANANQTMSVKIGDMGAKALGVDALKLEE   180
           ****  ********* *  *. *:** ***********.*  .*.*  . * . :  :

MRx0518    AFATSDIAAAKDKAVAAAFKADTTTKYAADGKVDAAAAGKTVADLQTAIDTAADDAAKATA  239
DSM100110  AKDAESEIAK--KVETAFLDAANSDKYDADGKIDASAGKTAAELKDAIENAADDTAKAAA  238
           *  :: : *   * *:**: **.:.*:*****:**:****.*:*:.***:****.**.*

MRx0518    QKTYDDALATFTASDEGKAAAAAETAIVENNP---ITKIDKAIKAVSAQRADLGAAQNR  296
DSM100110  QKTYDAALETFKASTNGQTAIATAKTEVEEASKNSTVSKIDEAIKTVSAQRADLGAAQNR  298
           *****.**:**.**::*: *:*:*:* :*:.    : **** **:**************

MRx0518    LEHTINNLGTTQENLSEANSRIRDVQMAQEMMSFTKSNILSQAATSMLAQANSMPNSVLS  356
DSM100110  LEHTINNLGTTQENLSEANSRIRDVQMAQEMMSFTKSNILSQAATSMLAQANSMPNSVLS  358
           ************************************************************

MRx0518    LLQG  360
DSM100110  LLQ-  361
           ***
```

FIG. 16

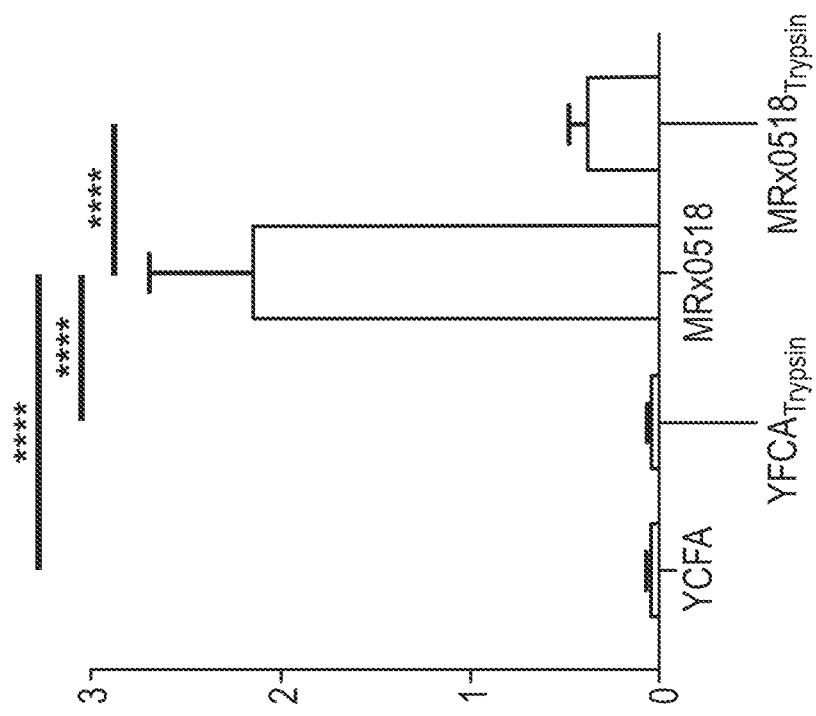
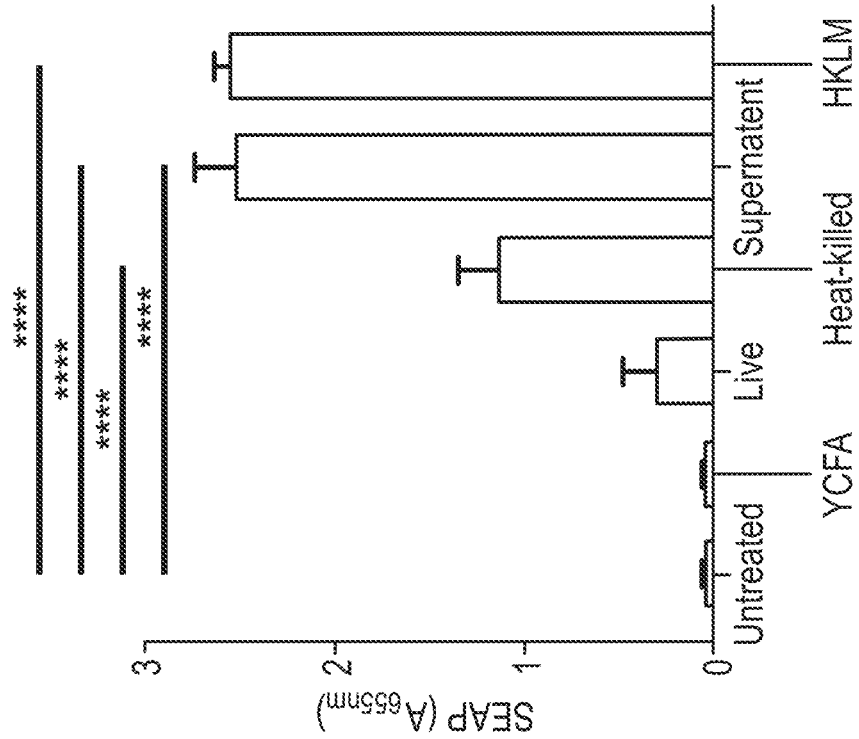
FIG. 18
NF-kB

ENTEROCOCCUS GALLINARUM FLAGELLIN POLYPEPTIDES

CROSS-REFERENCE

This application is a continuation of International Application No. PCT/EP2019/056809, filed Mar. 19, 2019, which claims the benefit of Great Britain Application No. 1804384.4, filed Mar. 19, 2018, Great Britain Application No. 1809953.1, filed Jun. 18, 2018; Great Britain Application No. 1811900.8, filed Jul. 20, 2018; Great Britain Application No. 1812378.6, filed Jul. 30, 2018; Great Britain Application No. 1813423.9, filed Aug. 17, 2018; Great Britain Application No. 1813444.5, filed Aug. 17, 2018; Great Britain Application No. 1816834.4, filed Oct. 16, 2018; Great Britain Application No. 1817641.2, filed Oct. 29, 2018; European Application No. 18178350.7, filed Jun. 18, 2018; Great Britain Application No. 1901199.8, filed Jan. 29, 2019; Great Britain Application No. 1901218.6, filed Jan. 29, 2019; Great Britain Application No. 1901992.6, filed Feb. 13, 2019; Great Britain Application No. 1901993.4, filed Feb. 13, 2019, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 5, 2020, is named 56708_739_301_Sequence_Listing.txt and is 139,859 bytes in size.

TECHNICAL FIELD

This invention is in the field of compositions comprising flagellin polypeptides from bacterial strains and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 500-1000 different phylotypes belonging essentially to two major bacterial divisions, the Bacteroidetes and the Firmicutes [2]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host. Similarly, the immunological importance of the gut microbiota is well-recognized and is exemplified in germfree animals which have an impaired immune system that is functionally reconstituted following the introduction of commensal bacteria [3-5].

In sharp contrast to the production of secretory intestinal IgA, which is influenced by microbial colonization per se [6-7], T cell development and differentiation seem to require colonization by specific commensal micro-organisms. *Clostridium* species, and in particular the spore-forming segmented filamentous bacteria (SFB), appear to be a potent stimulus for the differentiation and maturation of intestinal and colonic Th1, Th17 and Tregs [8-9]. More recent studies have demonstrated that other gut bacteria, including those of *Clostridium* clusters IV and XIVa and the Altered Schaedler Flora (ASF), can induce de novo generation of Tregs while mono-colonization with *Bacteroides fragilis* can correct the Th1/Th2 imbalance in germfree mice by promoting the expansion of Tregs [5][10-11]. These data infer important immune-regulatory effects of other resident gut bacteria. Clearly, the effects of commensal bacteria on T cell differentiation pathways is variable and as postulated previously may be influenced by the array of TLR ligands found associated with specific bacteria [12]. For example, the mechanism by which SFB influences T cell responses is currently unknown, but recent genome studies confirming the presence of flagellin genes suggest that innate responses mediated through TLR5-flagellin interactions may play a role [13-14].

Flagellin is one of the principal components of the bacterial flagellum. The flagellum is a lash-like appendage that provides the bacterium with motility and can act as a sensory organelle. The structure and composition of bacterial flagellin has been comprehensively studied in model organisms, such as *Salmonella typhimurium* and *E. coli*. Flagellin of *Salmonella typhimurium* and *E. coli* activate the immune system via the TLR5 receptor, which leads the activation of a variety of proinflammatory and immune response genes [15]. It has been suggested that TLR5 agonists, such as *Salmonella typhimurium* flagellin can act as anti-cancer agents [16]. *Salmonella typhimurium* engineered to express *Vibrio vulnifificus* flagellin has also been proposed to act as an anti-cancer agent [17]. Additionally, it has been suggested that flagellin peptides from *Salmonella typhimurium, Vibrio cholera* and *Shigella dysenteriae* can be used to produce vaccines against infectious disease such as typhoid, cholera and dysentery when expressed by intestinal bacteria which have been genetically modified [18]. However, flagellin from other species of bacteria remain poorly characterised and such other flagellin may have different effects or uses.

Dramatic changes in microbiota composition have been documented in gastrointestinal disorders such as inflammatory bowel disease (IBD). For example, the levels of *Clostridium* cluster XIVa bacteria are reduced in IBD patients whilst numbers of *E. coli* are increased, suggesting a shift in the balance of symbionts and pathobionts within the gut [19-22]. Interestingly, this microbial dysbiosis is also associated with imbalances in T effector cell populations.

In recognition of the potential positive effect that certain bacterial strains may have on the animal gut, various strains have been proposed for use in the treatment of various diseases (see, for example, [23-26]). Also, certain strains, including mostly *Lactobacillus* and *Bifidobacterium* strains, have been proposed for use in treating various inflammatory and autoimmune diseases that are not directly linked to the intestines (see [27] and [28] for reviews). However, the relationship between different diseases and different bacterial strains, and the precise effects of particular bacterial strains on the gut and at a systemic level and on any particular types of diseases, are poorly characterised. For example, certain *Enterococcus* species have been implicated in causing cancer [29].

Certain *Streptococcus* and *Veillonella* strains, and to a lesser extent, *Enterococcus* and *Lactobacillus* strains have been suggested to have immunomodulatory effects, with varying effects on different cytokines in vitro. However, the relationship between different diseases and different bacterial strains, and the precise effects of particular bacterial strains on the gut and at a systemic level and on any particular types of diseases, are poorly characterised.

There is a requirement in the art for new methods of treating diseases. There is also a requirement for the potential effects of gut bacteria to be characterised so that new therapies can be developed.

SUMMARY OF THE INVENTION

The inventors have developed new therapies for treating and preventing diseases. In particular, the inventors have identified that flagellin polypeptides from the genus *Enterococcus* are useful in therapy. As demonstrated in the examples, flagellin polypeptides from the genus *Enterococcus* can strongly activate TLR5 responses at levels significantly higher than the well-known TLR5 agonist *Salmonella. typhimurium* flagellin.

In preferred embodiments, the invention provides flagellin polypeptides from the species *Enterococcus gallinarum* for use in therapy. In further preferred embodiments, the flagellin polypeptide is from the strain deposited at NCIMB under accession number NCIMB 42488. In preferred embodiments, the flagellin polypeptide is SEQ ID NO:1. The examples show that flagellin polypeptides from the strain MRx0518 (the strain deposited under accession number NCIMB 42488) can more strongly activate a TLR5 response compared to flagellin polypeptides from other strains of *Enterococcus gallinarum*. Thus, flagellin polypeptides from the strain NCIMB 42488 are particularly effective for use in therapy.

In preferred embodiments, the flagellin polypeptide of the invention is in a monomeric form, which allows the polypeptide to more effectively bind with a TLR5 receptor.

The examples show that flagellin polypeptides from the strain NCIMB 42488 are particularly effective at activating a TLR5 response. Flagellin polypeptides from the strain NCIMB 42488 may not contain a D3 domain and the inventors have noted that the majority of the sequence variation between different flagellin polypeptides is observed in the D2-D3 region. In preferred embodiments, the invention provides flagellin polypeptides from the genus *Enterococcus* or species *Enterococcus gallinarum* that do not contain a D3 domain.

In certain embodiments, the flagellin polypeptide of the invention is part of a bacterial flagellar assembly. In certain embodiments, the invention provides a bacterial flagellar assembly comprising a flagellin polypeptide of the invention. In preferred embodiments the bacterial flagellar assembly contains the proteins FliL and FlaG. FliL and FlaG proteins are present in the bacterial flagellar assembly of MRx0518. The examples show that flagellin polypeptide from MRx0518 are particularly effective at activating a TLR5 response.

The invention also provides a polynucleotide sequence that encodes a flagellin polypeptide from the genus *Enterococcus* for use in therapy. In certain embodiments, the polynucleotide sequence encodes a flagellin polypeptide from the species *Enterococcus gallinarum* for use in therapy. In preferred embodiments, the polynucleotide sequence encodes a flagellin polypeptide from the strain MRx0518 for use in therapy.

In other embodiments, the invention provides a host cell expressing a recombinant flagellin polypeptide from the genus *Enterococcus*, for use in therapy. In other embodiments, the invention also provides a host cell comprising a recombinant polynucleotide sequence that encodes a flagellin polypeptide from the genus *Enterococcus*, for use in therapy.

The invention provides compositions comprising flagellin polypeptides of the invention. The invention also provides compositions comprising a polynucleotide sequence encoding a flagellin polypeptide of the invention. The invention also provides a host cell that expresses a flagellin polypeptide of the invention.

In addition, the invention also provides compositions comprising a host cell, wherein the host cell comprises a polynucleotide sequence that encodes a flagellin polypeptide of the invention.

Activation of TLR5 by *S. typhimurium* flagellin is known to suppress cell proliferation and tumour growth [48]. Compositions comprising *Enterococcus gallinarum* strains are effective at treating and preventing cancer [50]. The inventors have surprisingly shown that flagellin polypeptides from the species *Enterococcus gallinarum* are able to stimulate a strong TLR5 response, which may contribute to the anti-cancer activity of *Enterococcus* strains. Thus, the inventors have shown that flagellin polypeptides from the genus *Enterococcus*, and in particular the species *Enterococcus gallinarum* are useful in therapy, and particularly effective in treating and preventing cancer.

In preferred embodiments, compositions comprising flagellin polypeptides from the genus *Enterococcus* are for use in treating immunogenic tumours and/or solid tumours. In certain embodiments, compositions comprising flagellin polypeptides from the genus *Enterococcus* are for use in a method of treating or preventing lung cancer, breast cancer, liver cancer or colon cancer. Compositions comprising flagellin polypeptides from the genus *Enterococcus* may be particularly effective for reducing tumour size or preventing tumour growth in the treatment of cancer.

In preferred embodiments, the composition of the invention is administered by injection, preferably subcutaneously or alternatively intravenously, or intraperitoneally.

In certain embodiments, for example when the composition comprises a host cell of the invention, the composition of the invention is for oral administration. In certain embodiments, the composition of the invention comprises one or more pharmaceutically acceptable excipients or carriers.

Additionally, the invention provides a method of treating a disease, comprising administering a composition comprising a flagellin polypeptide from the genus *Enterococcus* bacterial strain to a patient in need thereof. In preferred embodiments, the invention provides a method of treating or preventing cancer, comprising administering a composition comprising a flagellin polypeptide from the genus *Enterococcus* bacterial strain to a patient in need thereof.

The inventors have developed new compositions comprising a flagellin polypeptide from the genus *Enterococcus*, preferably from the species *Enterococcus gallinarum* that can be used in stimulating the immune system and treating and preventing disease. The inventors have identified that such compositions can potently activate the immune system and can treat cancer, which indicates that they may able to also treat other diseases where activation of the immune system may be useful.

The invention therefore provides a composition comprising a flagellin polypeptide from the genus *Enterococcus*, for use in stimulating the immune system in subject.

In further aspects, the invention provides a composition comprising a flagellin polypeptide from the genus *Enterococcus*, for use in treating, preventing or delaying immunosenescence.

In further aspects, the invention provides a composition comprising a flagellin polypeptide from the genus *Enterococcus*, for use as a vaccine adjuvant.

In further aspects, the invention provides a composition comprising a flagellin polypeptide from the genus *Enterococcus*, for use in enhancing a cell therapy, such as CAR-T.

BRIEF DESCRIPTION OF DRAWINGS

FIGS. 3A-3J: Protein sequence alignment of flagellin polypeptides from strain MRx0518 with 23 flagellin polypeptides from the species *E. gallinarum*. The D0, D1 and D2 domains and the predicted TLR5 binding sites for the flagellin polypeptide from strain MRx0518 are highlighted. FIG. 3A: table depicting FIGS. 3B-3J. FIG. 3B: top row, left column of FIG. 3A; FIG. 3C: top row, middle column of FIG. 3A; FIG. 3D: top row, right column of FIG. 3A; FIG. 3E: second row, left column of FIG. 3A; FIG. 3F: second row, middle column of FIG. 3A; FIG. 3G: second row, right column of FIG. 3A; FIG. 3H: third row, left column of FIG. 3A; FIG. 3I: second row, right column of FIG. 3A; FIG. 3J: bottom row of FIG. 3A. FIGS. 3B-3I disclose SEQ ID NOS 53, 1, 3-16, 33, 36-37, 2, and 38-42, all respectively, in order of appearance.

FIG. 14: Electron microscopy of MRx0518.

FIG. 16: A sequence alignment of flagellin proteins from MRx0518 and DSM 100110 performed using CLUTAL OMEGA v2.1 multiple sequence alignment software. Figure discloses SEQ ID NOS 1-2, respectively, in order of appearance.

FIG. 18: Activation of NF-κB by MRx0518.

DISCLOSURE OF THE INVENTION

Flagellin

Flagellin, a principal component of bacterial flagella, stimulates host defence in a variety of organisms, including mammals, insects, and plants. The structure and composition of bacterial flagellin has been comprehensively studied in model organisms such as *S. typhimurium* and *E. coli*. However, there is very limited data available describing flagellin from the genus *Enterococcus* and in particular the species *Enterococcus gallinarum*.

Flagellin can exist either as a monomeric protein or can be polymerised to form a flagellum filament. Bacterial flagellum filaments in *Salmonella* are composed of approximately 20,000 flagellin protein units. Flagellum filaments form part of a fully assembled bacterial flagellum.

Figure 1:
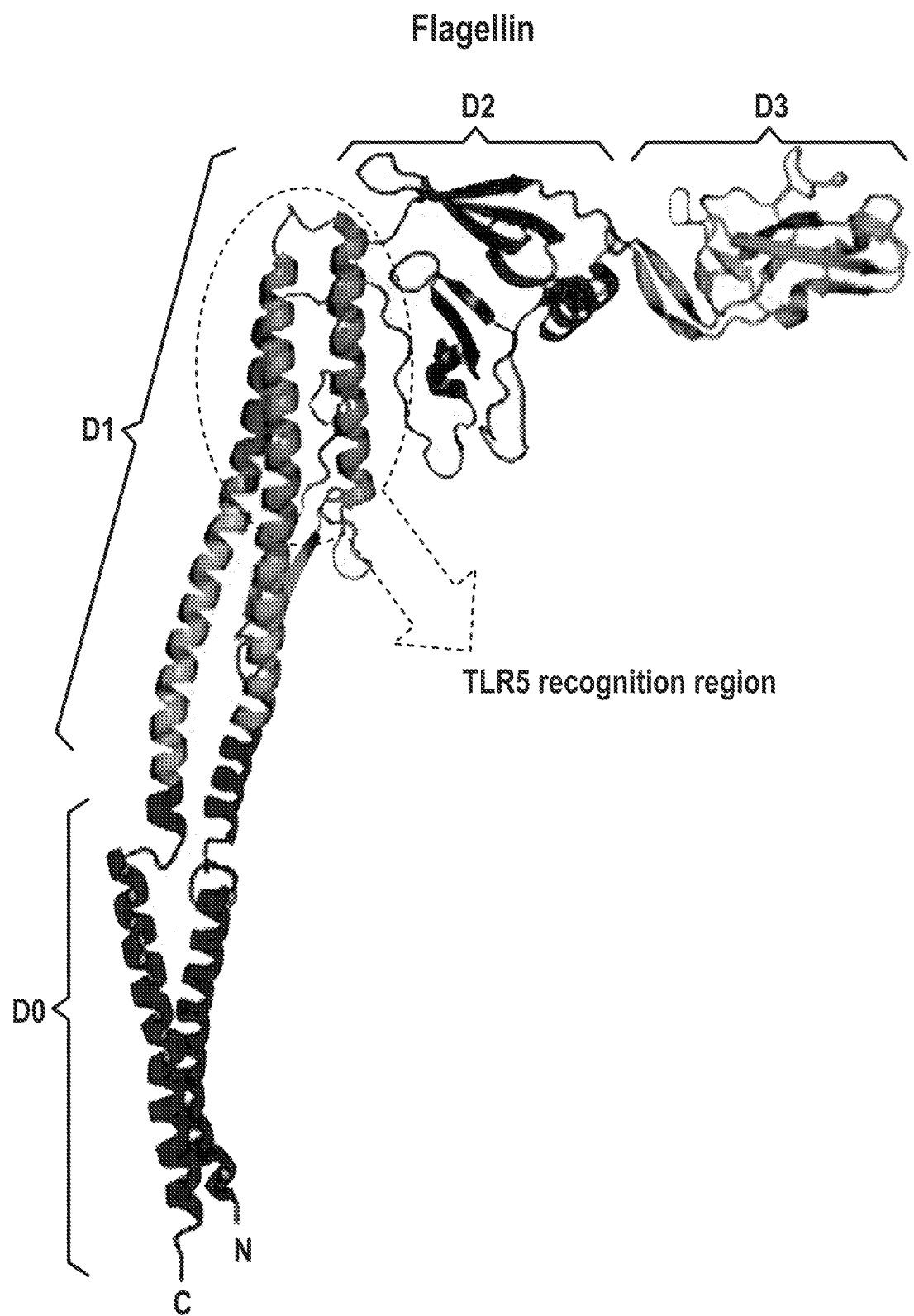
FIG. 1: The structure of flagellin and the cross-sectional and top views of the flagellar filament. The flagellar filament is composed of a single protein, flagellin. The TLR5 recognition region is in the D1 domain and is not accessible when flagellin is polymerised in the flagellar filament. Image is from reference [30].
Figure 1:
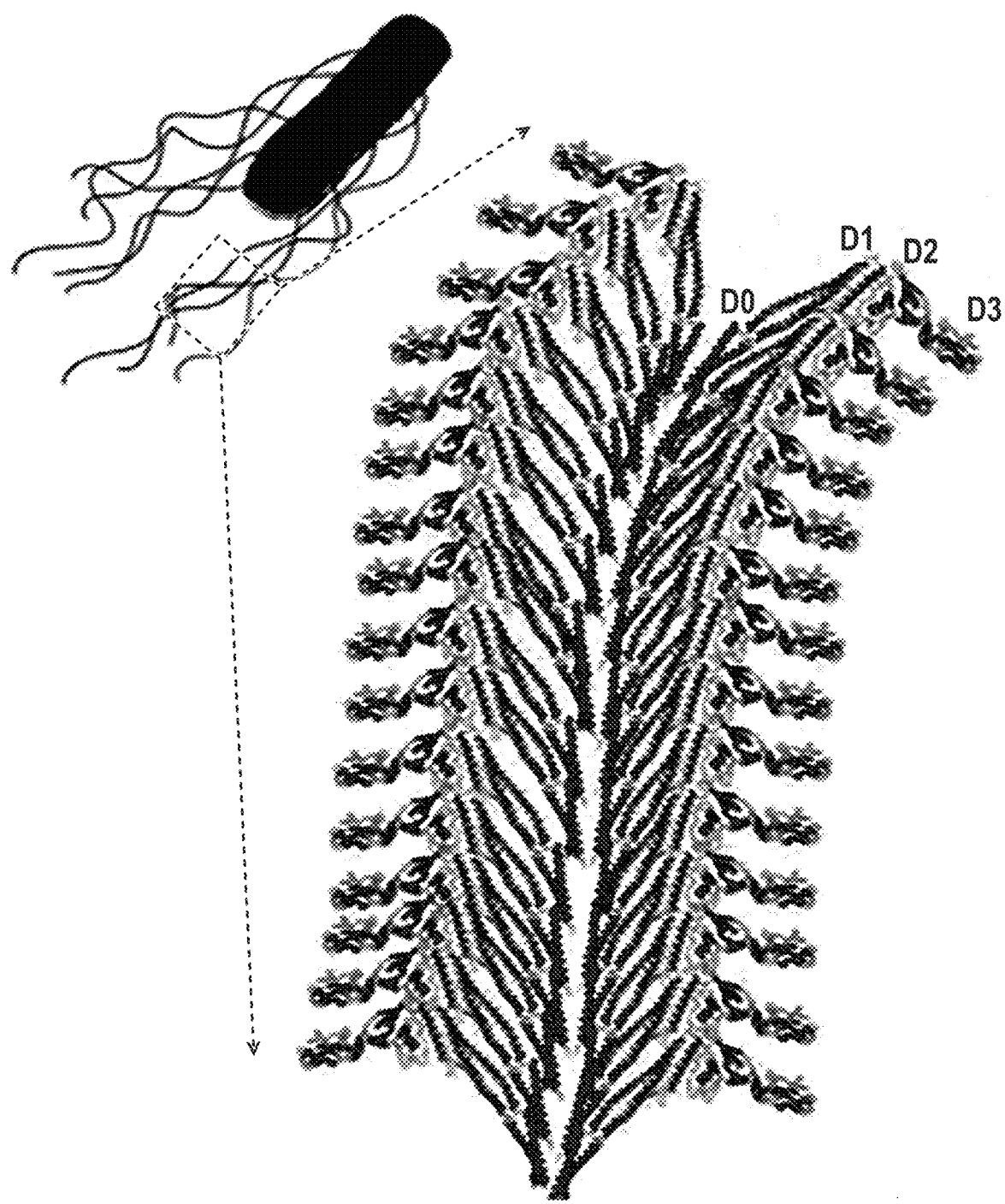
Figure 1:
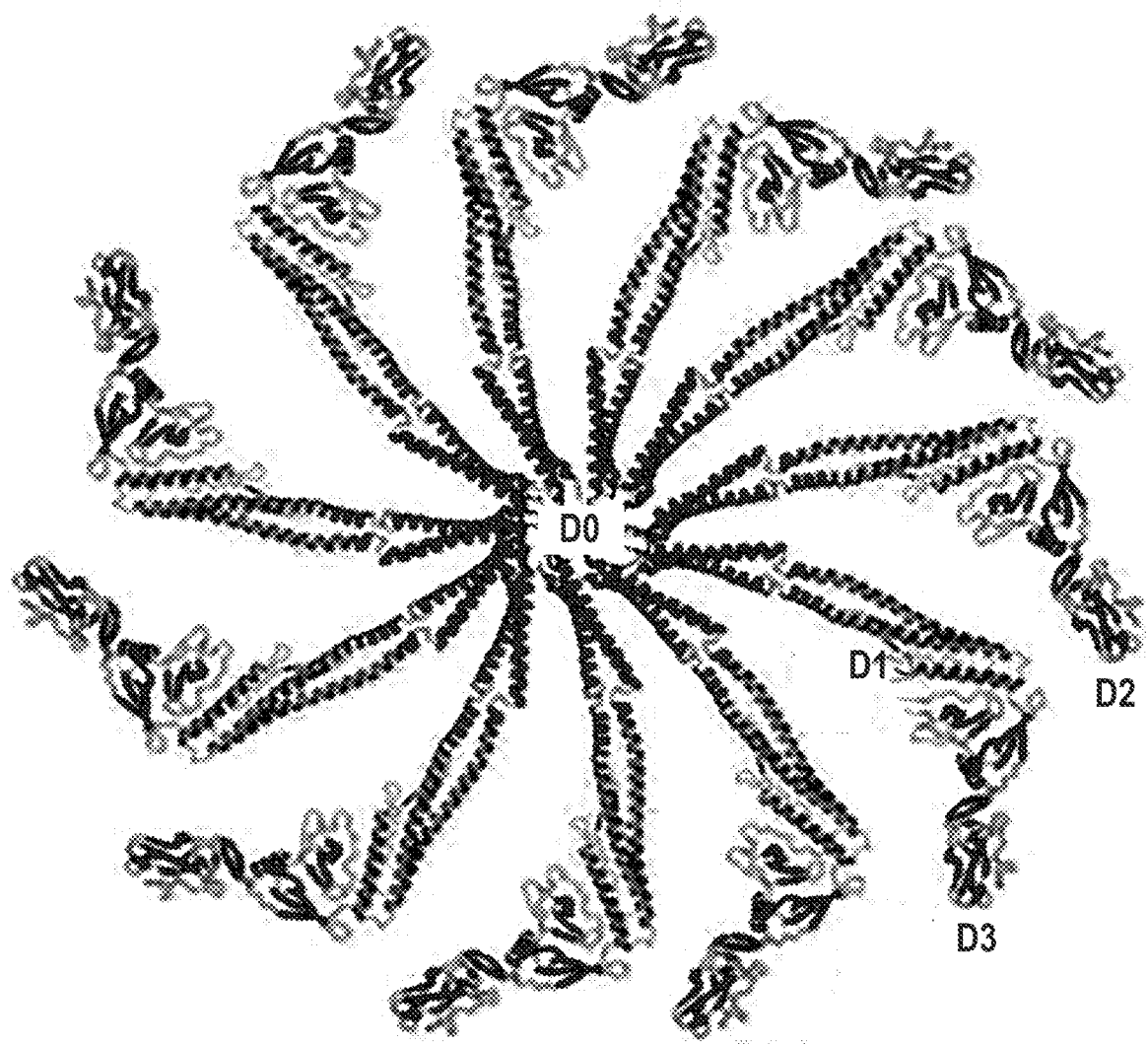

Flagellin proteins generally contain 3-4 domains (D0, D1, D2 and D3), with the D0 and D1 domains consisting of a fold over from the N- and C-termini [31]. During flagellum filament assembly, the D0 and D1 domains are buried within the flagellum filament with the D2 and/or D3 domains facing outwards (FIG. 1).

Amino acid motifs within the conserved domain D1 have been shown to be required for TLR5 recognition and interaction [32-33]. The D0 domain has also been shown to affect TLR5 signalling [34]. The TLR5 recognition site is generally not accessible in the flagellar filament. Flagellin interacts more effectively with TLR5 in its monomeric form, as the TLR5 binding sites are not accessible when assembled in a filament [30]. The central region of the flagellin protein displays sequence variability and has not been studied extensively but is considered to be an antigenic and immunogenic region of the protein.

Figure 2:
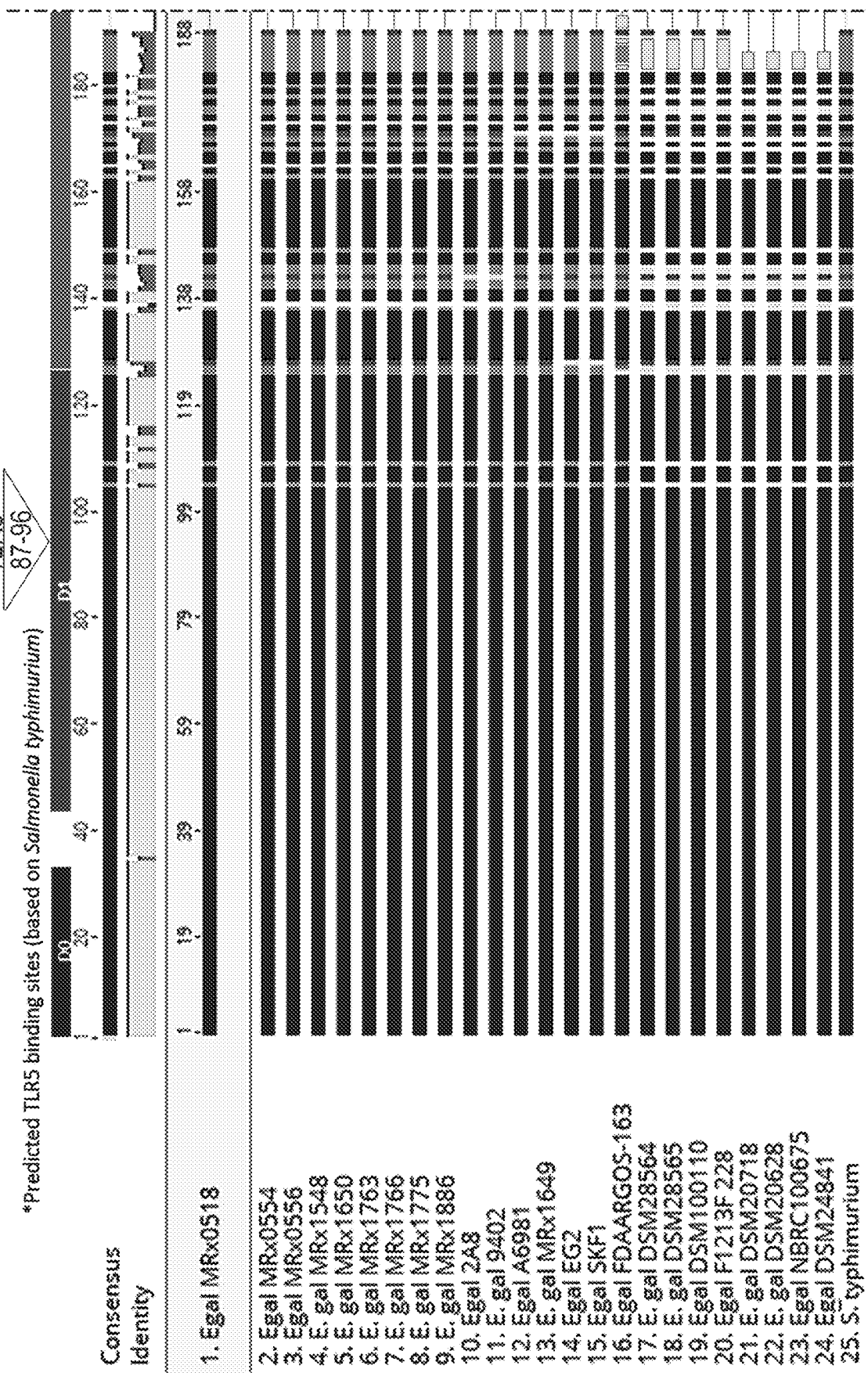
FIG. 2: Protein sequence alignment of 24 flagellin polypeptides from the species *Enterococcus gallinarum* and the model organism *S. typhimurium*. The D0, D1 and D2 domains and the predicted TLR5 binding sites for the flagellin polypeptide from strain MRx0518 are highlighted.
Figure 2:
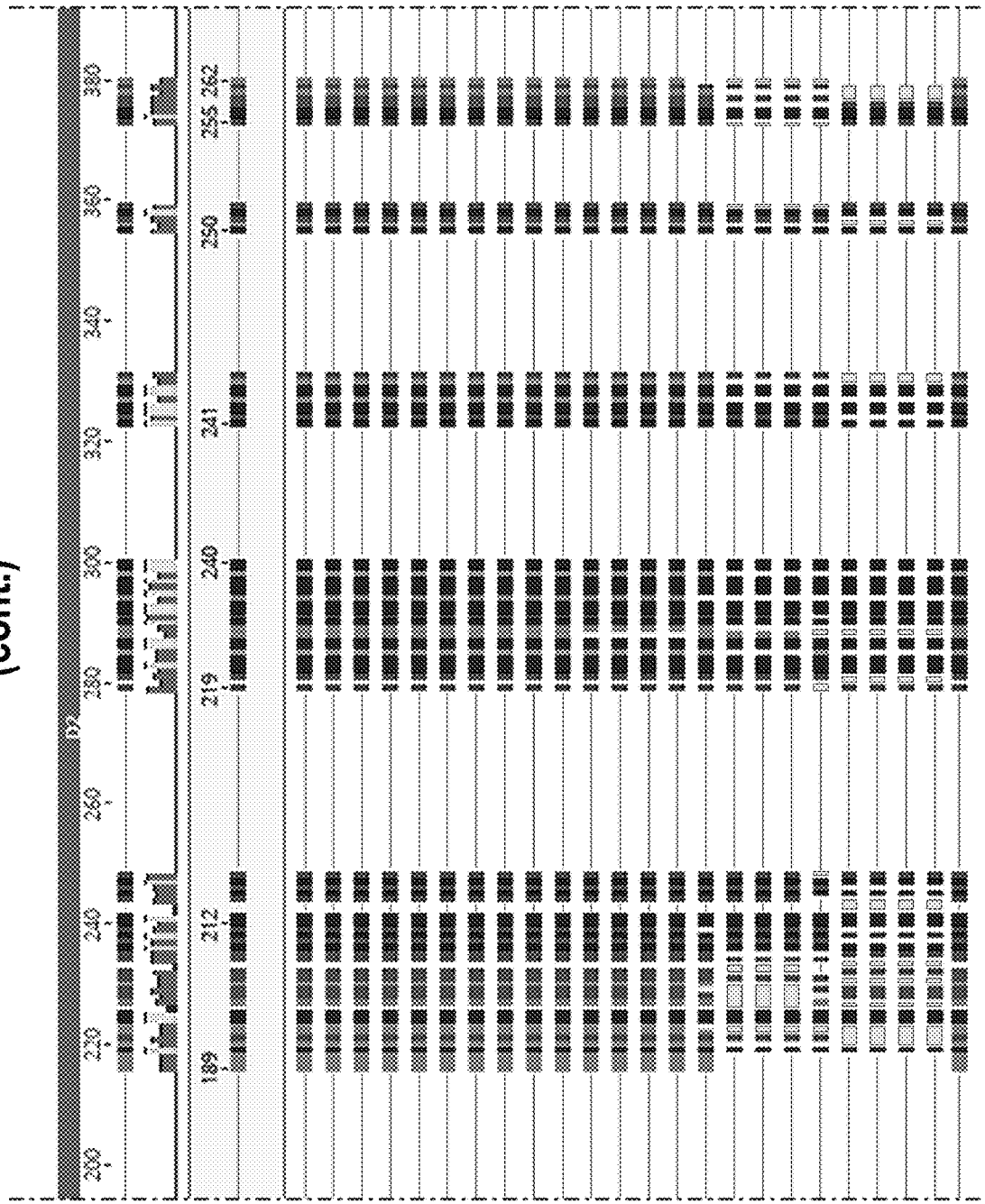
Figure 2:
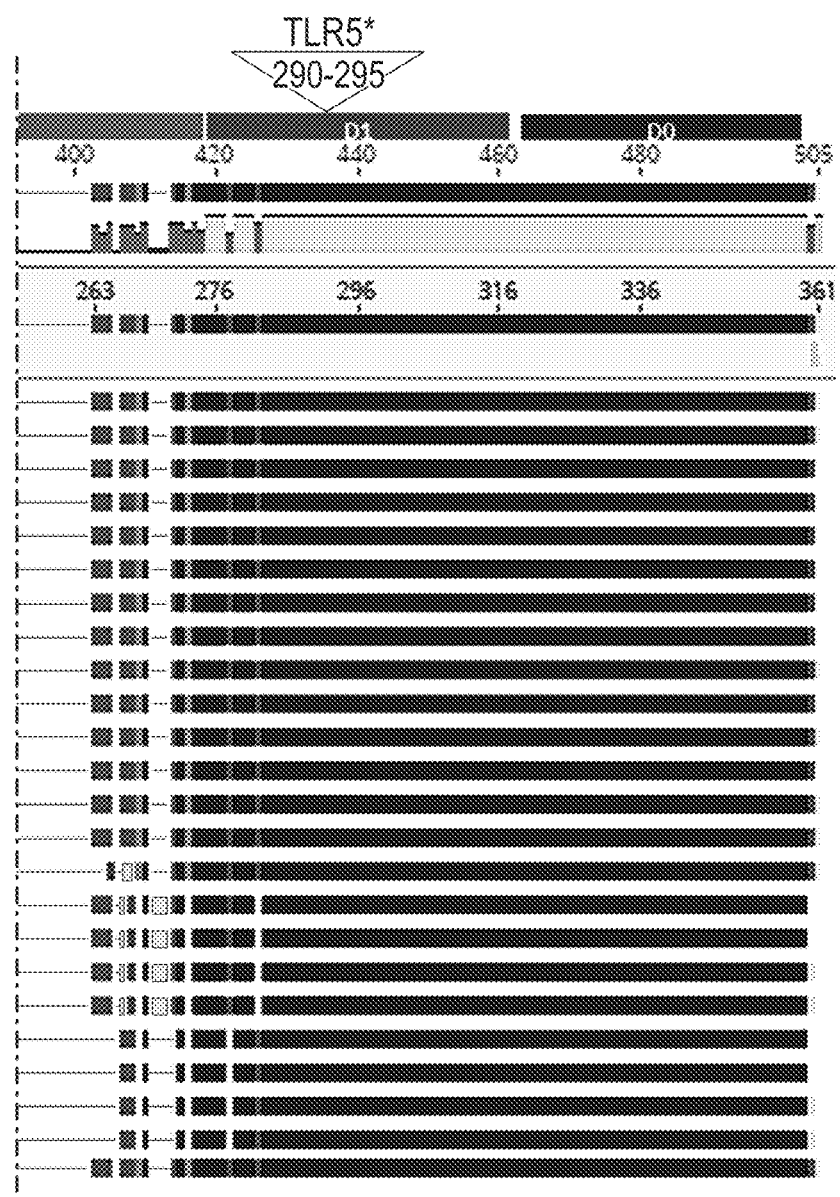
Figure 3A:
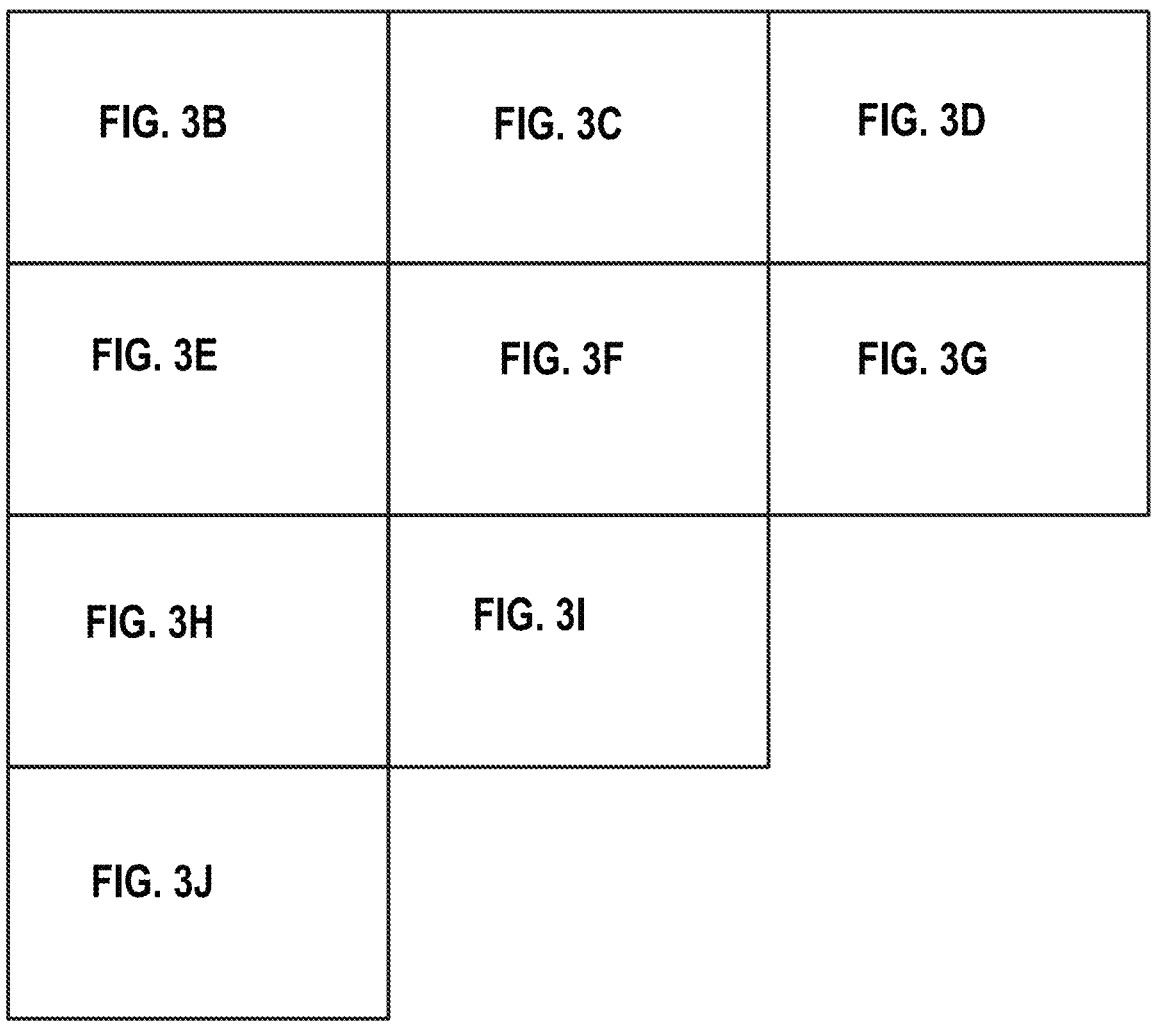
Figure 3B:
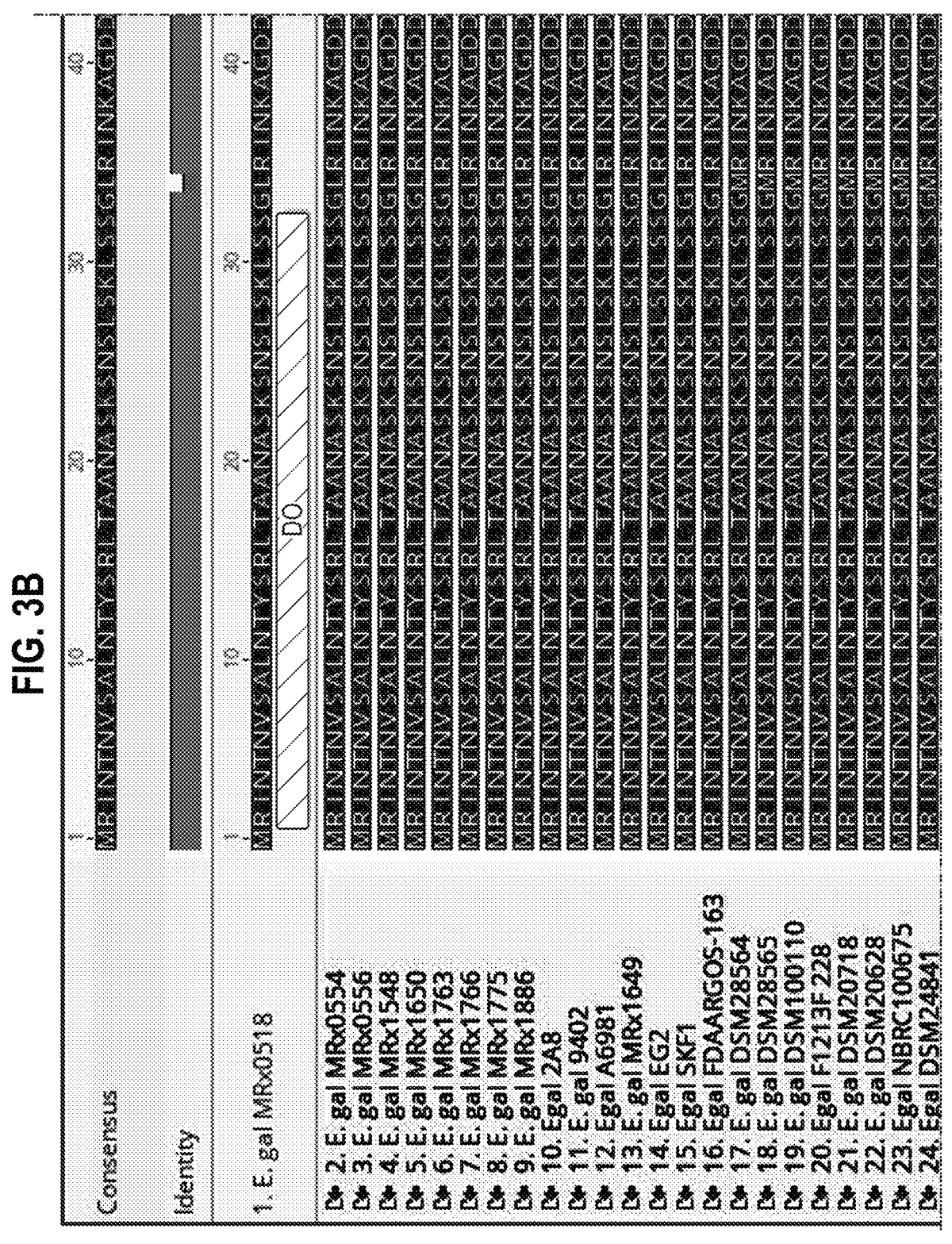
Figure 3C:
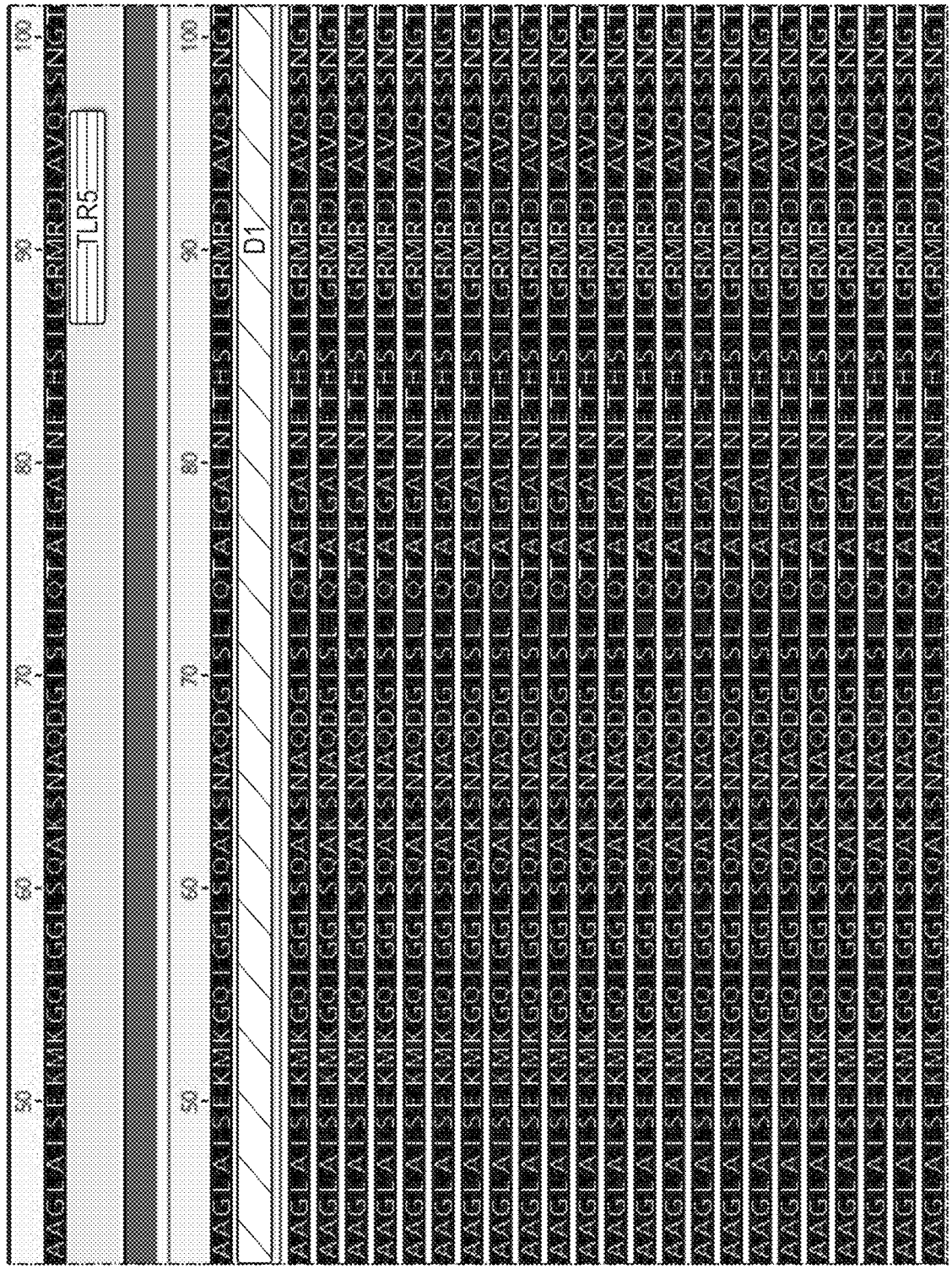
Figure 3D:
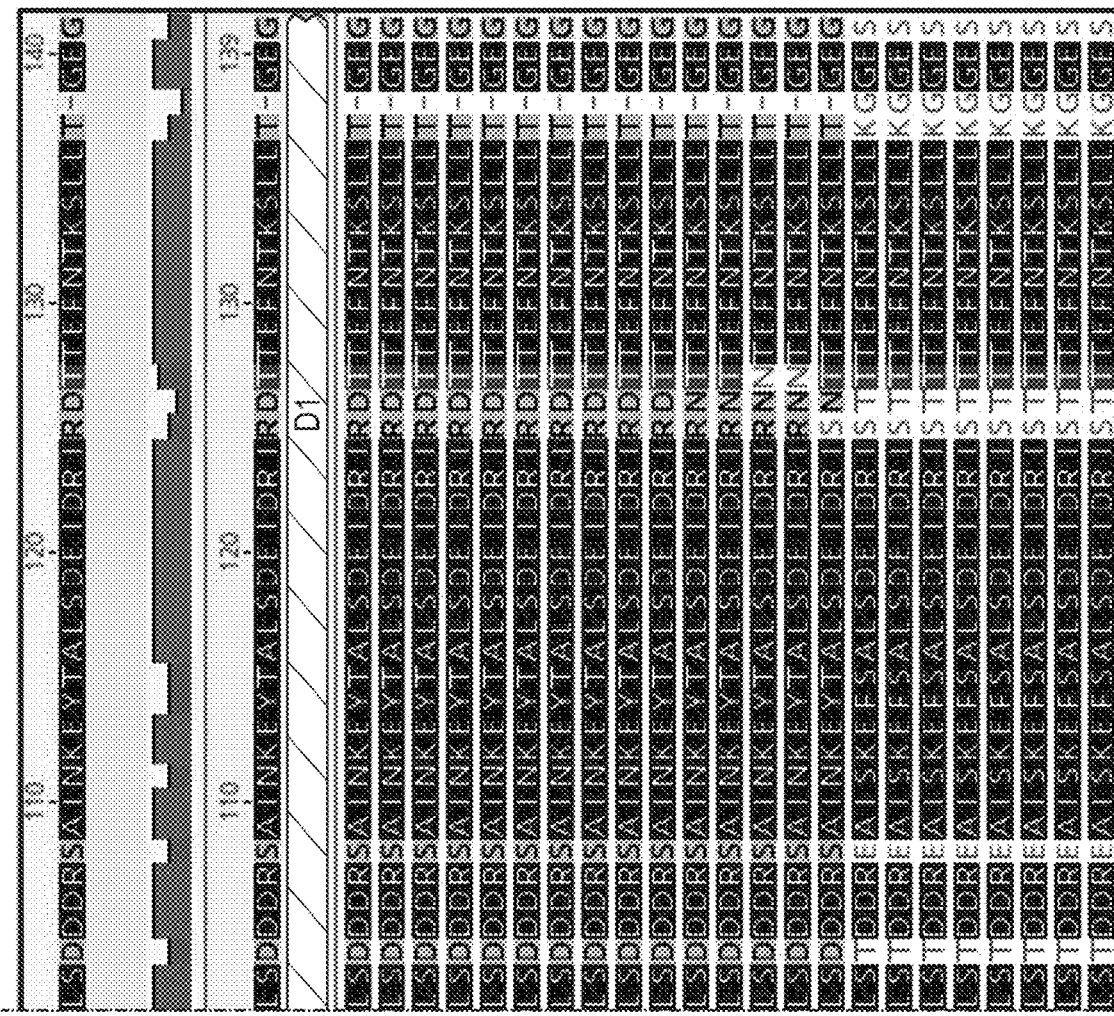
Figure 3E:
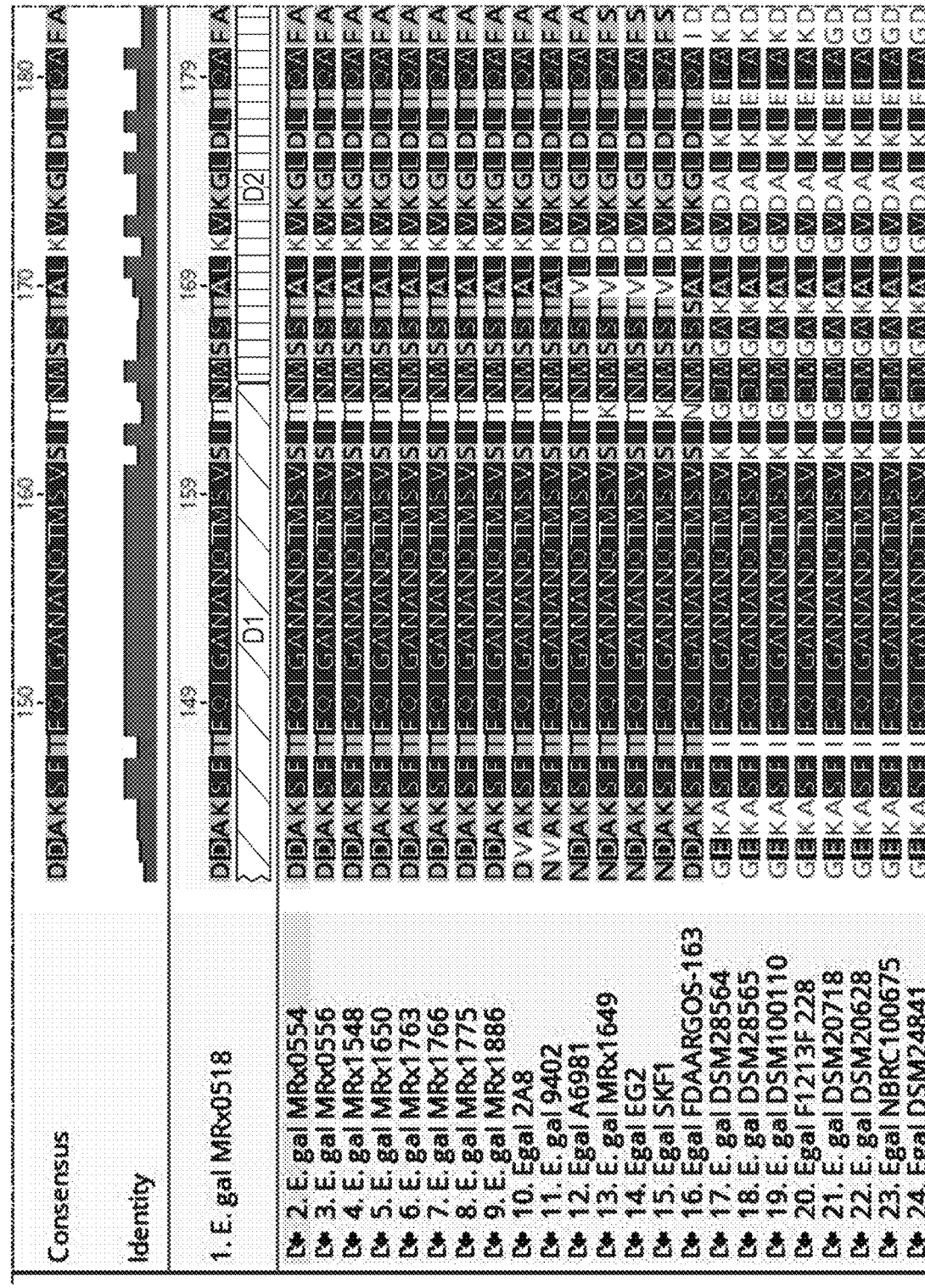
Figure 3F:
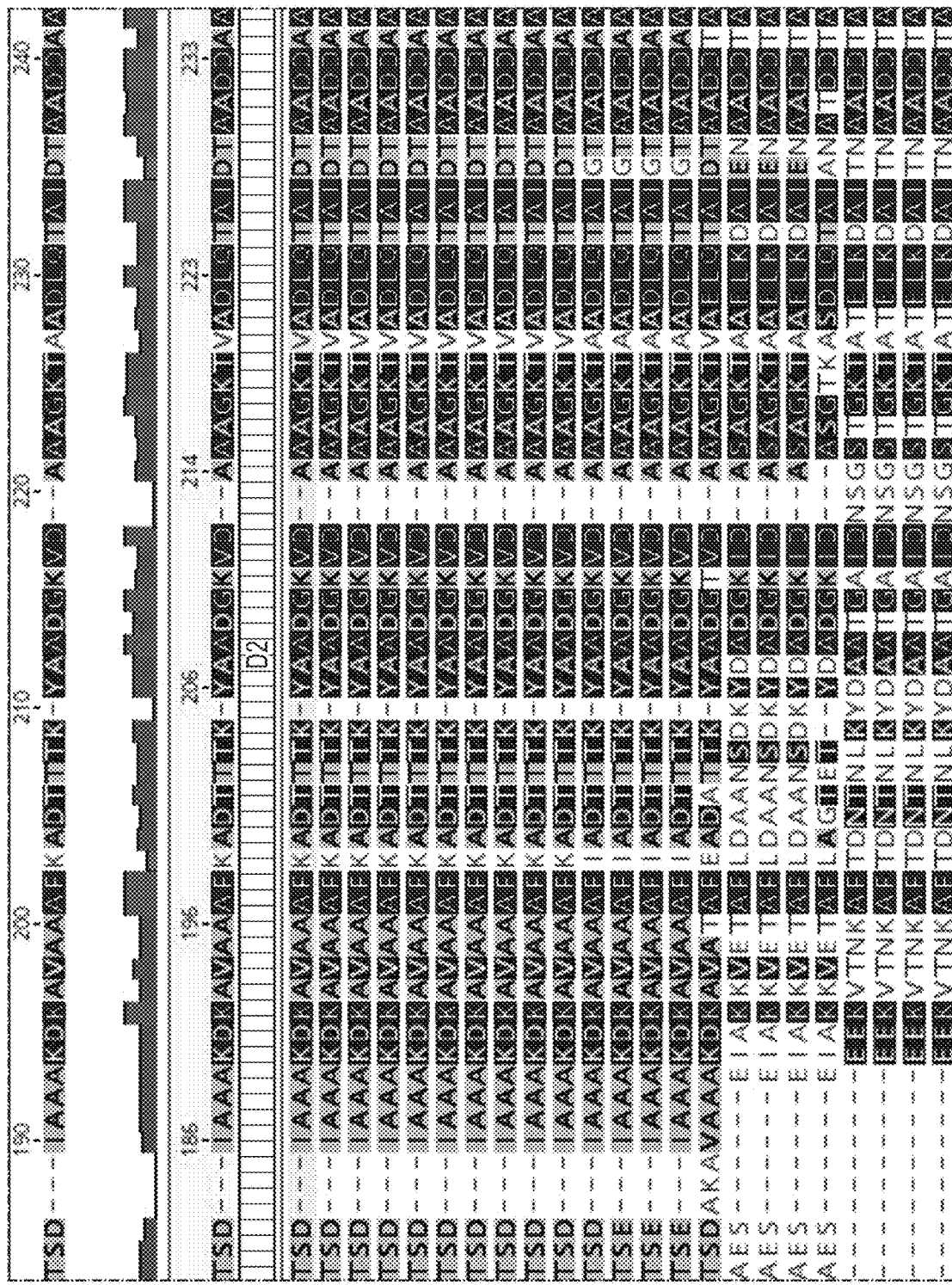
Figure 3H:
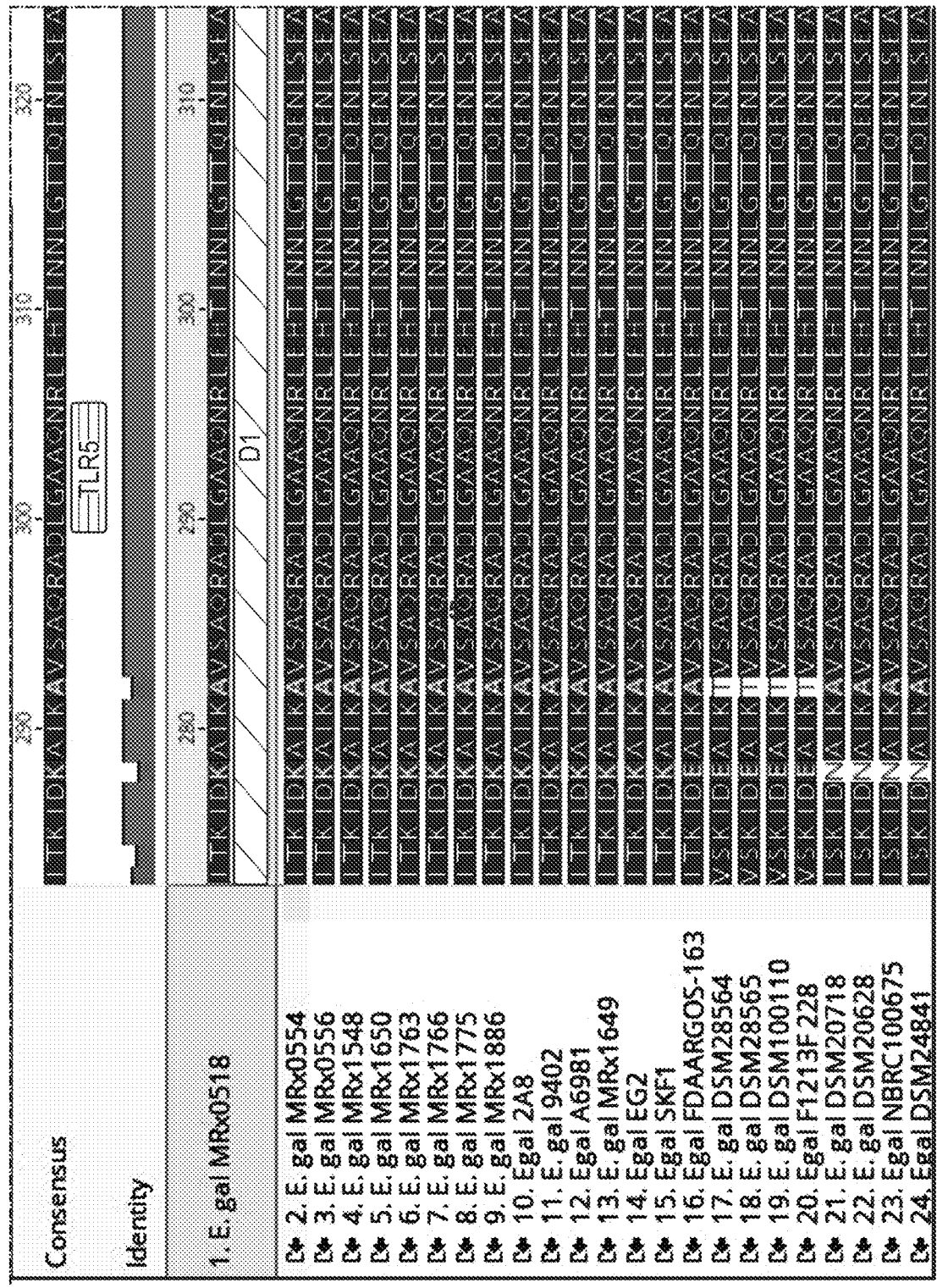
Figure 3I:
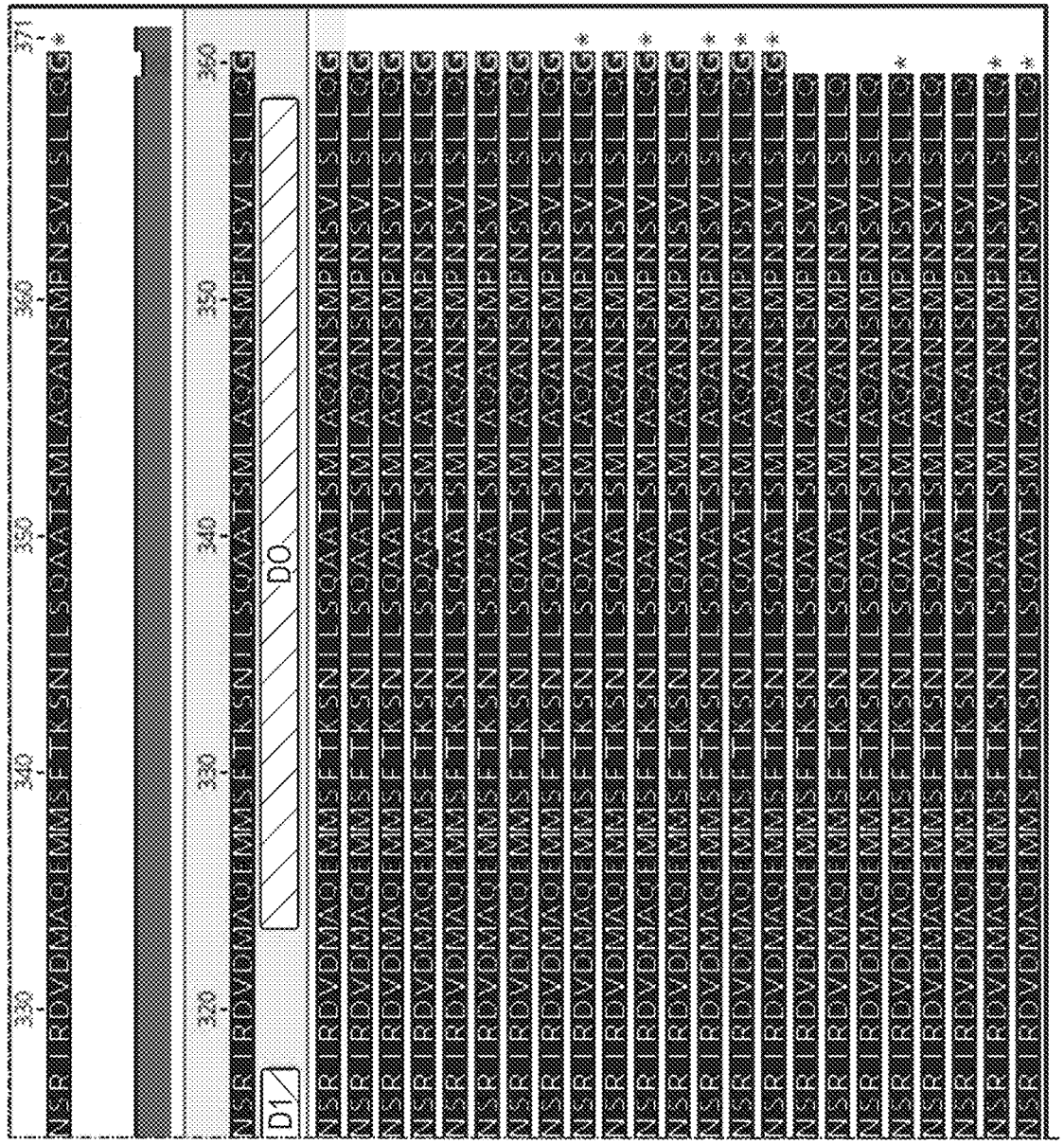
Figure 3J:
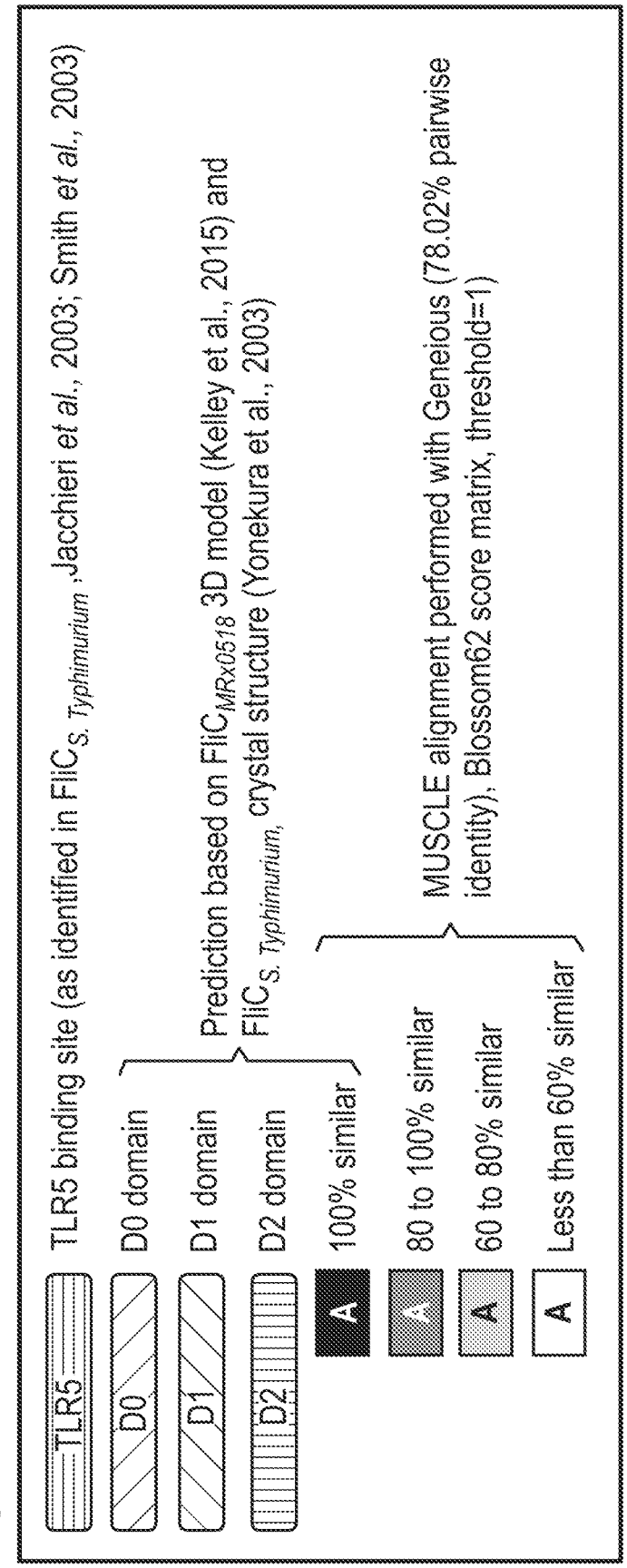

The D0 and D1 domains are highly conserved, while the D2 and D3 domains are more variable [35]. FIG. 2 is a sequence alignment of flagellin proteins from the genus *Enterococcus* with the extensively studied flagella protein from *S. typhimurium*. The majority of the sequence variation between the flagellin protein from *S. typhimurium* and the flagellin proteins from the genus *Enterococcus* lies within the central region (D2-D3 domain). The majority of the sequence variation between different *Enterococcus gallinarum* strains is also observed in this region, for example between flagellin proteins from the strains MRx0518 and DSM100110 (FIG. 3).

Figure 4:
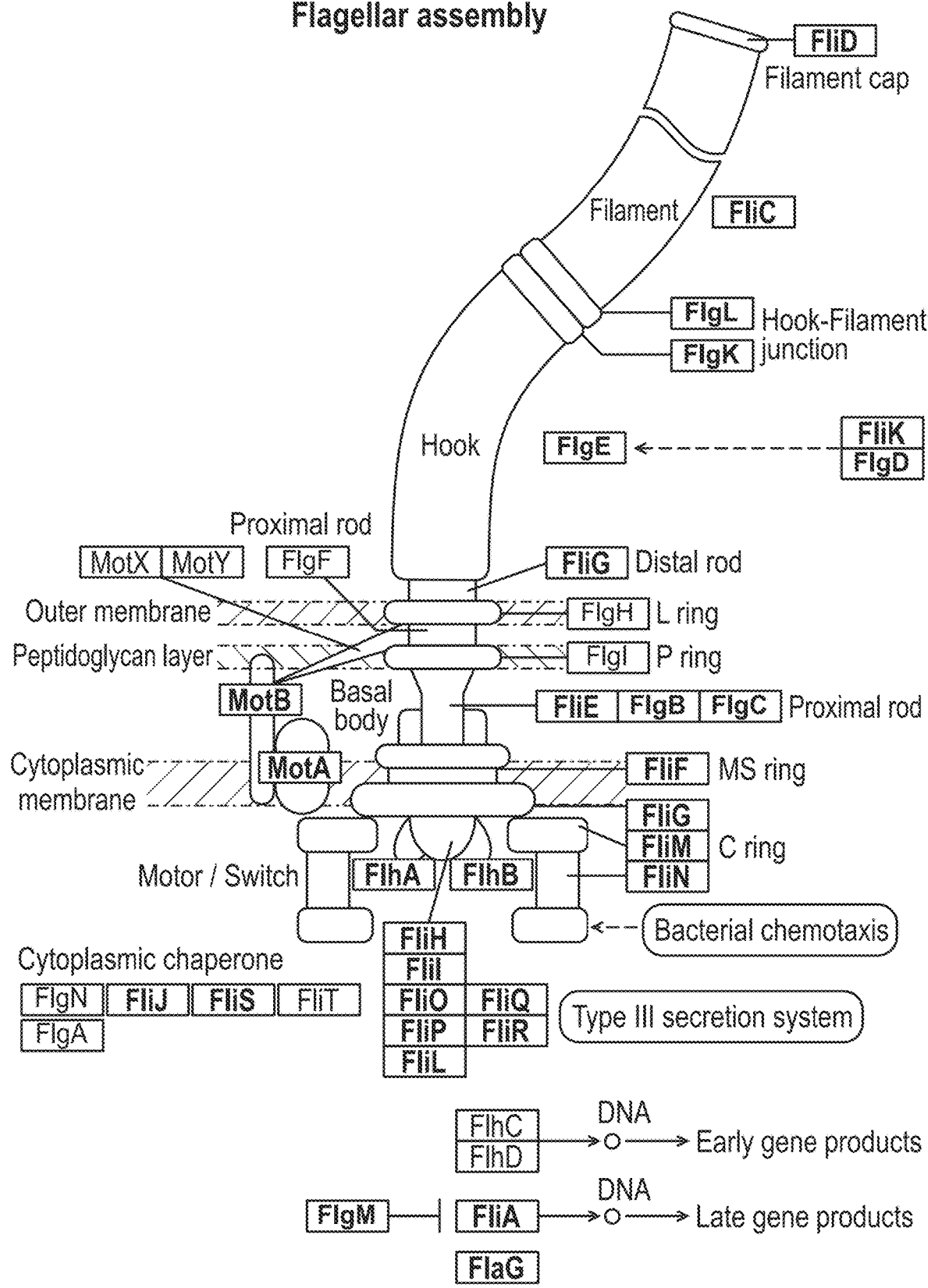
FIG. 4: KEGG Pathway diagram of flagellar assembly. Genes highlighted in grey are present in the species.

The flagellum filament is a component of the bacterial flagellum. The genes known to be involved in bacterial flagellar assembly are summarised in FIG. 4. Those shaded in grey are present in *Enterococcus gallinarum*. The flagellin proteins are encoded by FliC, which is also interchangeably referred to herein as FlaA.

The invention provides a flagellin polypeptide from the genus *Enterococcus* for use in therapy. In certain embodiments, the invention provides a flagellin polypeptide from the species *Enterococcus gallinarum* for use in therapy. In preferred embodiments, the invention provides a flagellin polypeptide from the strain MRx0518 for use in therapy. The examples demonstrate that flagellin polypeptides from the genus *Enterococcus* can activate a strong TLR5 response, which shows flagellin polypeptides may be useful in therapy, and in particular useful in treating cancer.

The invention provides a flagellin polypeptide from the genus *Enterococcus* for use in a method of treating or preventing cancer. In certain embodiments, the invention provides a flagellin polypeptide from the species *Enterococcus gallinarum* for use in a method of treating or preventing cancer. In preferred embodiments, the invention provides a flagellin polypeptide from the strain MRx0518 for use in a method of treating or preventing cancer. The examples demonstrate that flagellin polypeptides from the genus *Enterococcus* are able to induce strong TLR5 responses, which is useful in treating and preventing cancer. In particular, the examples show that flagellin polypeptides from the species *Enterococcus gallinarum* and especially strain MRx0518 produce a very high TLR5 response.

In preferred embodiments, the invention provides a flagellin polypeptide from the species *Enterococcus gallinarum* or the species *Enterococcus casseliflavus*, for use in therapy, in particular for treating or preventing cancer. In certain embodiments, the flagellin polypeptide is from the species *Enterococcus casseliflavus*. In the most preferred embodiments, the flagellin polypeptide is from the species *Enterococcus gallinarum*.

Flagellin polypeptides from the strain MRx0518 were tested in the examples. MRx0518 is a strain of *Enterococcus gallinarum* bacterium deposited under accession number NCIMB 42488. Strain MRx0518 was deposited with the international depositary authority NCIMB, Ltd. (Ferguson Building, Aberdeen, AB21 9YA, Scotland) by 4D Pharma Research Ltd. (Life Sciences Innovation Building, Aberdeen, AB25 2ZS, Scotland) on 16 Nov. 2015 as "*Enterococcus* sp" and was assigned accession number NCIMB 42488.

All microorganism deposits were made under the terms of the Budapest Treaty and thus viability of the deposit is assured. Maintenance of a viable culture is assured for 30 years from the date of deposit. During the pendency of the application, access to the deposit will be afforded to one determined by the Commissioner of the United States Patent and Trademark Office to be entitled thereto. All restrictions on the availability to the public of the deposited microorganisms will be irrevocably removed upon the granting of a patent for this application. The deposit will be maintained for a term of at least thirty (30) years from the date of the deposit or for the enforceable life of the patent or for a period of at least five (5) years after the most recent request for the furnishing of a sample of the deposited material, whichever is longest. The deposit will be replaced should it become necessary due to inviability, contamination or loss of capability to function in the manner described in the specification.

In certain embodiments, the invention provides a flagellin polypeptide with at least 75% sequence identity to the flagellin polypeptide from the strain MRx0518, and use of such polypeptides in therapy, and in particular in treating or preventing cancer. The examples show that such flagellin polypeptides are especially effective. In particular, the invention provides a flagellin polypeptide having a sequence with at least 75%, 80%, 85%, 90%, 95%, 96%, 97%, 98%, 99%, 99.5% or 99.9% sequence identity to SEQ ID NO:1. Preferably, the flagellin polypeptide of the invention comprises or consists of SEQ ID NO:1. In other embodiments, the flagellin polypeptide has a sequence with at least 75%, 80%, 85%, 90%, 95%, 96%, 97%, 98%, 99%, 99.5% or 99.9% sequence identity to SEQ ID NO:2. The flagellin polypeptide of the invention may comprise or consist of SEQ ID NO:2. The examples also demonstrate that such polypeptides are useful.

In certain embodiments, the invention provides a flagellin polypeptide with at least 75%, 80%, 85%, 90%, 95%, 96%, 97%, 98%, 99%, 99.5% or 99.9% sequence identity to one of SEQ ID NO:3-42. In preferred embodiments, the flagellin polypeptide has a sequence with at least 95%, 96%, 97%, 98%, 99%, 99.5% or 99.9% sequence identity to one of SEQ ID NO:3-16. In preferred embodiments, the flagellin polypeptide is from the species *Enterococcus gallinarum*.

In preferred embodiments, the flagellin of the invention binds TLR5, for example with a $K_D$ value of at least $10^{-2}$, at least $10^{-3}$, at least $10^{-4}$, at least $10^{-5}$, at least $10^{-6}$, at least $10^{-7}$, at least $10^{-8}$, at least $10^{-9}$, at least $10^{-10}$, or at least $10^{-11}$. Binding to TLR5 may be measured by any appropriate method known in the art, including electrochemical impedance spectroscopy (EIS), scanning electrochemical microscopy (SECM) [36], or native PAGE and gel-filtration chromatography analyses using a recombinant TLR5 protein [37].

Figure 5:
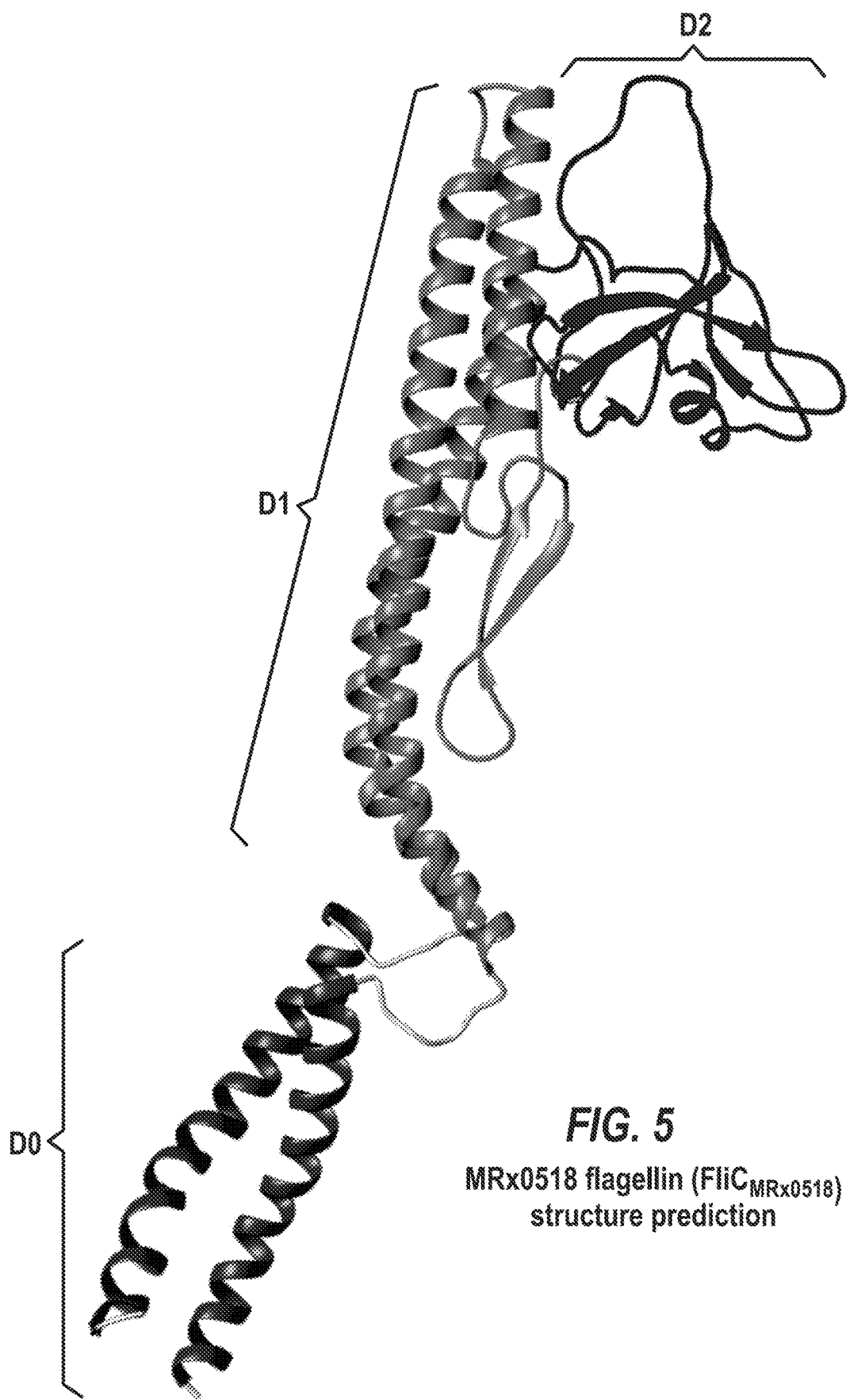
FIG. 5: Comparison of the predicted MRx0518 flagellin (FliC$_{MRx0518}$) protein structure with the known *S. typhimurium* flagellin protein structure. The *S. typhimurium* flagellin protein structure is from reference [30].
Figure 5:
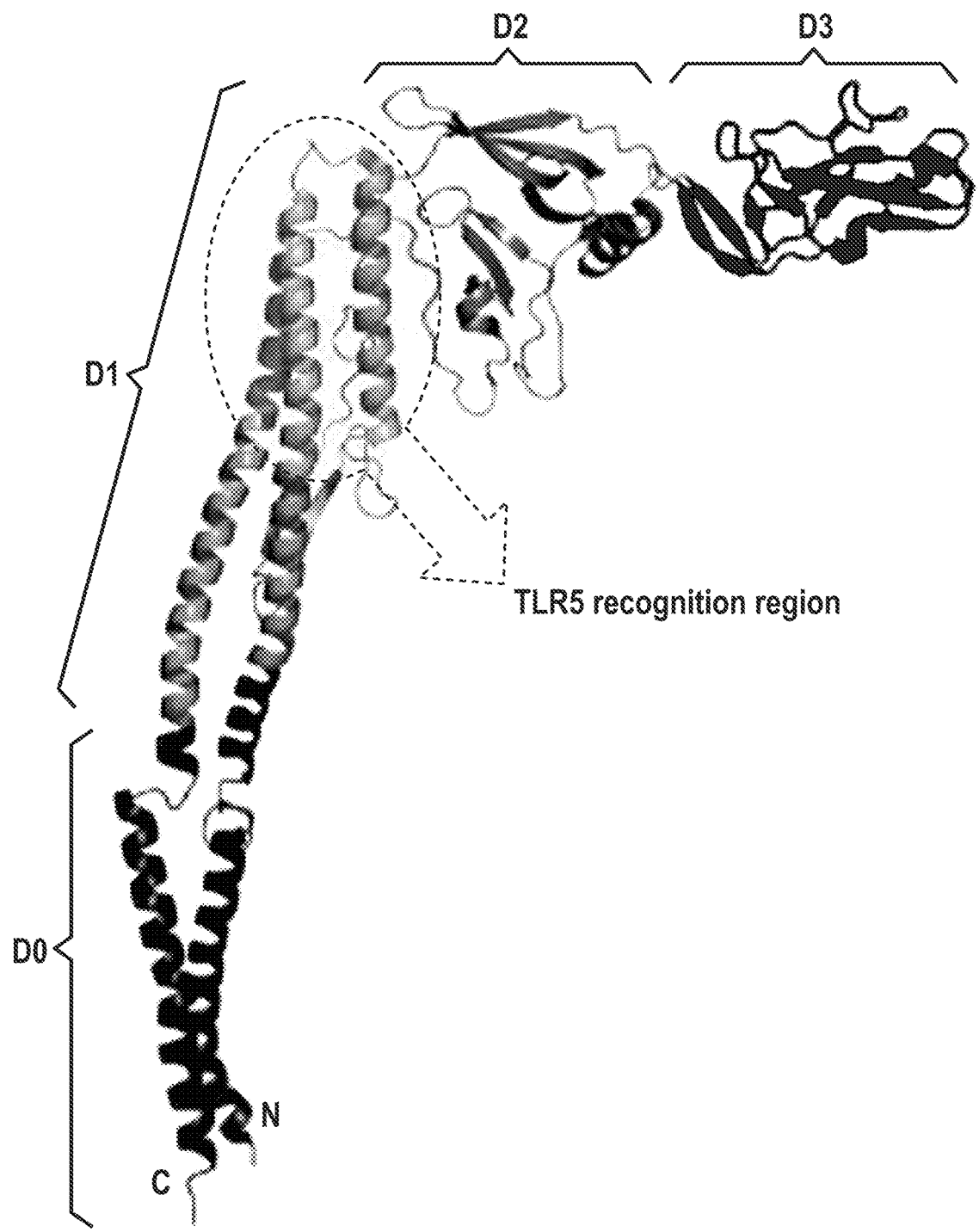

The flagellin polypeptides of the invention can contain four domains, D0, D1, D2 and D3. In preferred embodiments, the flagellin polypeptide does not comprise a D3 domain. In certain embodiments the flagellin polypeptide of the invention consists of three domains, D0, D1, D2. The location of the D0, D1 and D2 domains in *E. gallinarum* flagellin polypeptide are shown in FIG. 3. The predicted shape of the flagellin polypeptide from the strain MRx0518 (FliC$_{MRx0518}$) is shown in FIG. 5. The predicted structure of FliC$_{MRx0518}$ was generated using the Phyre2 tool which predicts protein structure based on homology with publicly available structures [38] and the graphic was generated with the UCSF Chimera package [39]. The predicted lack of D3 domain leads to a conformation change in the protein structure compared to flagellin polypeptide from *S. typhimurium* SL1344 (GenBank Accession No. CBW17983). The predicted lack of a D3 domain may lead to the TLR5 recognition site being more exposed, which leads to an increase in the ability of the flagellin polypeptide to activate a TLR5 response. The predicted lack of a D3 domain may also affect the ability of flagellin polypeptide polymerise into a flagellum filament. Flagellin polypeptide activates TLR5 responses more effectively in the monomeric form, therefore preventing or reducing the polymerisation of flagellin polypeptides is beneficial.

The flagellin polypeptides of the invention may contain a D1 domain, which may be required for TLR5 recognition and interaction. In certain embodiments, the invention provides a flagellin polypeptide with a D1 domain that has at least 95%, 96%, 97%, 98%, 99%, 99.5% or 99.9% sequence identity to residues 43-164 and 273-317 in SEQ ID NO:1. In certain embodiments, the invention provides a flagellin polypeptide with a TLR5 recognition site in the D1 domain. The TLR recognition site in flagellin polypeptides from the species *Enterococcus gallinarum* is located at position 87-96 and 290-295 in SEQ ID NO:1. In preferred embodiments, the TLR5 recognition site of the flagellin polypeptide has at least 99%, 99.5% or 99.9% identity to residues 87-96 and 290-295 in SEQ ID NO:1. In further preferred embodiments, the flagellin polypeptide comprises the TLR5 recognition site of residues 87-96 and 290-295 in SEQ ID NO:1.

The flagellin polypeptide of the invention may also contains a D0 domain, which can affect TLR5 signalling. In certain embodiments, the invention provides a flagellin polypeptide with at D0 domain that has at least 95%, 96%, 97%, 98%, 99%, 99.5% or 99.9% identity to residues 2-32 and 234-358 in SEQ ID NO:1.

The flagellin polypeptide of the invention may also contain a D2 domain. The majority of the sequence variation between the flagella polypeptides from *S. typhimurium* and the genus *Enterococcus* lie within the central region (D2-D3 domain). The examples show that flagellin polypeptides from the species *Enterococcus gallinarum* are able to produce stronger TLR5 response at a lower dosage compared to flagellin polypeptide from *S. typhimurium*. The sequence variation in the D2 or D3 domain may contribute to the increased ability of flagellin polypeptides from the species *Enterococcus gallinarum* to activate a TLR5 response. The flagellin polypeptide of the invention also contains a D0 domain, which can affect TLR5 signalling. In certain embodiments, the invention provides a flagellin polypeptide with at D2 domain that has at least 75%, 80%, 85%, 90%, 95%, 96%, 97%, 98%, 99%, 99.5% or 99.9% identity to residues 165-272 in SEQ ID NO:1.

Flagellin polypeptide can exist as a monomer or in a polymerised form as a flagellum filament. This filament is part of the bacterial flagellum. In certain embodiments, the flagellin polypeptide of the invention is arranged in flagellum filament. The invention also relates to flagellin polypeptides not arranged in flagellum filament. In preferred embodiments, the flagellin polypeptide is in its monomeric form. The monomeric form of the flagellin polypeptide is advantageous as it can interact more strongly with TLR5. In embodiments, the flagellin of the invention is not glycosylated, to aid its shedding and disaggregation into the monomeric form.

In certain embodiments, the flagellin polypeptide is part of a bacterial flagellum. In certain embodiments, the flagellin polypeptide is part of a bacterial flagellum that contains one or more proteins selected from FliD, FlgL, FlgK, FlgE, FliK, FlgD, FlgG, MotB, MotA, FliF, FliG, FliM, FliN, FlhA FlhB, FliH, FliI, FliO, FliP, FliQ, FliR, FliL, FliJ and FliS. In preferred embodiments, the bacterial flagellar assembly contains FliD, FlgL, FlgK, FlgE, FliK, FlgD, FlgG, MotB, MotA, FliF, FliG, FliM, FliN, FlhA FlhB, FliH, FliI, FliO, FliP, FliQ, FliR, FliL, FliJ and FliS. In certain embodiments, the bacterial flagellar assembly contains the proteins FliL and FlaG. FliL is flagellar basal body-associated protein, which controls the rotational direction of the flagella during chemotaxis and FlaG regulates flagellin assembly along with FlaF. FliL and FlaG proteins are present in MRx0518. The examples show that flagellin polypeptide from MRx0518 can activate a stronger TLR5 response compared to flagellin polypeptide from another *Enterococcus gallinarum* species.

The flagellin polypeptides of the invention may be recombinantly expressed, or they may be isolated from *Enterococcus* cells. In certain embodiments, the flagellin polypeptide of the invention is not attached to an *Enterococcus* cell. In certain embodiments, the flagellin polypeptide of the invention is in a composition that is substantially free of bacterial cells.

In certain embodiments, the flagellin polypeptides of the invention have been heat treated, and optionally denatured. The examples demonstrate that such flagellin polypeptides are still potently effective. In certain embodiments, the flagellin polypeptides of the invention are heat-stable to 80° C., for example can maintain activity following heating to 80° C. for, for example, 40 mins. In certain embodiments, the flagellin polypeptides are digested by trypsin. In other words, in certain embodiments, the flagellin polypeptides contain trypsin cleavage sites. The MRX518 flagellin is predicted to contain 36 trypsin cleavage sites.

A flagellin polypeptide according to the invention does not have to function as a normal flagellin polypeptide in order to be considered a flagellin polypeptide. A flagellin polypeptide according to the invention may contain mutations or deletions that ablate certain activities. Generally, a flagellin polypeptide of the invention is a TLR5 agonist. In certain embodiments, the flagellin polypeptides of the invention are not able to polymerise into a flagellum filament. In other embodiments, the flagellin polypeptides of the invention are not able to form part of the bacterial flagellar assembly.

In certain embodiments, the polypeptides of the invention are not flagellin polypeptides. In preferred embodiments, the polypeptides have sequence identity to SEQ ID NO:1, as set out above, or comprise or consist of SEQ ID NO:1.

The invention also provides compositions comprising a flagellin polypeptide from the genus *Enterococcus* for use in therapy. In certain embodiments, the composition comprises a flagellin polypeptide from the species *Enterococcus gallinarum* for use in therapy. In preferred embodiments, the composition comprises a flagellin polypeptide from the strain MRx0518 for use in therapy.

In alternative aspects of every embodiment of the invention, the flagellin polypeptide of the invention is of the species *Enterococcus caselliflavus*. *Enterococcus caselliflavus* is highly similar to *Enterococcus gallinarum* and is also flagellated.

Fragments

Flagellin polypeptides with sequence identity to those tested in the examples are expected to also be useful in therapy and are encompassed by the invention, as set out in the preceding section. In addition, fragments of flagellin polypeptides of the invention are also expected to be useful.

Preferably, any fragment is at least 7, 10, 20, 30, 40, 50, 60, 70, 80, 90, 100, 150, 200, 250, 300 or 350 amino acids in length.

Preferred fragments comprise one or more of the following stretches of amino acids of SEQ ID NO:1: 2-32, 87-96, 165-272, 234-358, 290-295, or comprise a sequence with at least 90%, 92%, 95%, 98% or 99% sequence identity to one of said fragments.

Preferred fragments comprise a sequence with at least 90%, 92%, 95%, 98% or 99% sequence identity to amino acids 165-272 of SEQ ID NO:1. Further preferred fragments comprise a sequence with at least 90%, 92%, 95%, 98% or 99% sequence identity to amino acids 87-96, 165-272 or 290-295 of SEQ ID NO:1, or preferably to amino acids 87-96, 165-272 and 290-295 of SEQ ID NO:1.

A fragment for use according to the invention will usually (i) have at least w % sequence identity to SEQ ID NO: 1 and/or (ii) comprise of a fragment of at least x contiguous amino acids from SEQ ID NO: 1. The value of w is at least 85 (e.g. 86, 87, 88, 89, 90, 91, 92, 93, 94, 95, 96, 97, 98, 99 or more). The value of x is at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 250, 300) and the fragment will usually include an epitope from SEQ ID NO: 1. The fragment will usually be able to bind to TLR5.

Other fragments for use according to the invention will usually (i) have at least w % sequence identity to SEQ ID NO: 2 and/or (ii) comprise of a fragment of at least x contiguous amino acids from SEQ ID NO: 2. The value of w is at least 85 (e.g. 86, 87, 88, 89, 90, 91, 92, 93, 94, 95, 96, 97, 98, 99 or more). The value of x is at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 250, 300) and the fragment will usually include an epitope from SEQ ID NO: 2. The fragment will usually be able to bind to TLR5.

Other fragments for use according to the invention will usually (i) have at least w % sequence identity to one of SEQ ID NO: 3-42 and/or (ii) comprise of a fragment of at least x contiguous amino acids from one of SEQ ID NO: 3-42. The value of w is at least 85 (e.g. 86, 87, 88, 89, 90, 91, 92, 93, 94, 95, 96, 97, 98, 99 or more). The value of x is at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 250, 300) and the fragment will usually include an epitope from one of SEQ ID NO: 3-42. The fragment will usually be able to bind to TLR5.

Fusions

Fusions comprising the flagellin polypeptides of the invention are also expected to be useful in therapy. Therefore, in certain embodiments, the invention provides a fusion polypeptide comprising a flagellin polypeptide as described above, optionally for use in therapy, and in particular for use in treating cancer. Preferred fusion partners include targeting moieties and moieties intended to prolong half-life. In certain embodiments the invention provides a fusion polypeptide comprising a flagellin polypeptide as described above and a polypeptide selected from the group consisting of an Fc region, transferrin, albumin, recombinant PEG, a homoamino acid polymer, a proline-alanine-serine polymer, an elastin-like peptide, or carboxy-terminal peptide [CTP; of chorionic gonadotropin(CG) b-chain].

The flagellin polypeptides of the invention may also be fused or conjugated to non-polypeptide moieties in order to improve their characteristics and therapeutic utility. For example, in certain embodiments, the invention provides a flagellin polypeptide as described above covalently linked to PEG or hyaluronic acid.

The flagellin polypeptides of the invention may be fused or conjugated to an antigen, for example, for use as a vaccine. Presenting an antigen in close proximity to the flagellin of the invention may maximise their immunostimulatory activities and further enhance the protective immune response generated against the antigen. In addition, manufacturing and delivering therapeutics comprising an antigen and a flagellin of the invention may be more efficient and effective when they are fused or conjugated. Therefore, in certain embodiments, the invention provides a fusion polypeptide comprising a flagellin polypeptide as described above and an antigen. In further embodiments, the invention provides a flagellin polypeptide as described above conjugated to an antigen.

Preferred antigens for including in the fusions and conjugates of the invention are pathogen antigens and tumour antigens. An antigen will elicit an immune response specific for the antigen that will be effective for protecting against infection with the pathogen or attacking the tumour. Antigens may be, for example, peptides or polysaccharides. Exemplary antigens for use with the fusions and conjugates of the invention include: viral antigens, such as viral surface proteins; bacterial antigens, such as protein and/or saccharide antigens; fungal antigens; parasite antigens; and tumor antigens. Further antigens for use with the fusions and conjugates of the invention include glycoprotein and lipoglycan antigens, archaea antigens, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 and habit forming substances, for example nicotine, alcohol or opiates.

Fusion polypeptides of the invention may include a linker sequence between the flagellin and the antigen. Preferred linker sequences include peptides that comprise (Gly4)n motif(s) (SEQ ID NO: 50), a (Gly4Ser)n motif(s) (SEQ ID NO: 51), and Ser(Gly4Ser)n motif(s) SEQ ID NO: 52). Linker sequences may be 1-50, 1-30, 1-20, 5-20, 5-10 or 10-20 amino acids in length. Linker sequences will allow the flagellin and the fusion partner, for example the antigen, to perform their roles and, for example, be accessed by the immune system. Therefore, in certain embodiments, the invention provides a fusion polypeptide comprising a flagellin polypeptide as described above, a linker sequence, and an antigen, such as an antigen derived from a pathogen, or a tumour antigen.

Flagellin polypeptides of the invention may be particularly useful when conjugated to non-polypeptide moieties such as polysaccharide antigens. Suitable conjugation methods include using carbodiimides, hydrazides, active esters, norborane, p-nitrobenzoic acid, N-hydroxysuccinimide, S—NHS, EDC, CDAP or TSTU.

Polynucleotides

The invention also provides a polynucleotide sequence that encodes a flagellin polypeptide from the genus *Enterococcus* for use in therapy. In certain embodiments, the polynucleotide sequence encodes a flagellin polypeptide from the species *Enterococcus gallinarum* for use in therapy. In preferred embodiments, the polynucleotide sequence encodes a flagellin polypeptide from the strain MRx0518 for use in therapy. The examples demonstrate that flagellin polypeptides from the genus *Enterococcus* can activate a strong TLR5 response, so polynucleotides encoding such flagellin polypeptides may be useful in therapy, and in particular useful in treating cancer.

The invention also provides a polynucleotide sequence that encodes a flagellin polypeptide from the genus *Enterococcus* for use in a method of treating or preventing cancer. In certain embodiments, the invention provides a polynucleotide sequence that encodes a flagellin polypeptide from the species *Enterococcus gallinarum* for use in a method of treating or preventing cancer. In preferred embodiments, the invention provides a polynucleotide sequence that encodes a flagellin polypeptide from the strain MRx0518 for use in a method of treating or preventing cancer. The examples demonstrate that flagellin polypeptide from the genus *Enterococcus* are able to induce strong TLR5 responses, which is useful in treating and preventing cancer. In particular, the examples show that flagellin polypeptides from the species *Enterococcus gallinarum* and especially strain MRx0518 produce a very high TLR5 response.

In preferred embodiments, the polynucleotide of the invention for use in therapy encodes SEQ ID NO:1, or a polypeptide sequence with 75%, 80%, 85%, 90%, 95%, 96%, 97%, 98%, 99%, 99.5% or 99.9% sequence identity to SEQ ID NO:1. In further preferred embodiments, the polynucleotide of the invention encodes a flagellin with the particular D0, D1 and/or D2 sequences set out above, which are shown in the examples to be useful.

In other embodiments, the polynucleotide of the invention for use in therapy encodes SEQ ID NO:2, or a polypeptide sequence with 75%, 80%, 85%, 90%, 95%, 96%, 97%, 98%, 99%, 99.5% or 99.9% sequence identity to SEQ ID NO:2. In further preferred embodiments, the polynucleotide of the invention encodes a flagellin with the particular D0, D1 and/or D2 sequences set out above, which are shown in the examples to be useful.

In other embodiments, the polynucleotide of the invention for use in therapy encodes one of SEQ ID NO: 3-42, or a polypeptide sequence with 75%, 80%, 85%, 90%, 95%, 96%, 97%, 98%, 99%, 99.5% or 99.9% sequence identity to one of SEQ ID NO: 3-42. In further preferred embodiments, the polynucleotide of the invention encodes a flagellin with the particular D0, D1 and/or D2 sequences set out above, which are shown in the examples to be useful.

Nucleic acid according to the invention can take various forms (e.g. single stranded, double stranded, vectors etc.). Nucleic acids of the invention may be circular or branched, but will generally be linear.

The term "polynucleotide" or "nucleic acid" includes both single-stranded and double-stranded nucleotide polymers. The nucleotides comprising the nucleic acid can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

Nucleic acids may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

The nucleic acids of the invention comprise a sequence which encodes at least one polypeptide of the invention, such as a flagellin polypeptide of the invention. Typically, the nucleic acids of the invention will be in recombinant form, i.e. a form which does not occur in nature. For example, the nucleic acid may comprise one or more heterologous nucleic acid sequences (e.g. a sequence encoding another antigen and/or a control sequence such as a promoter or an internal ribosome entry site) in addition to the sequence encoding at least flagellin polypeptide. In such embodiments, the nucleic acid of the invention encodes a flagellin polypeptide as discussed above and an antigen, such as a pathogen antigen or a tumour antigen. Optionally, the nucleic acid also encodes a linker sequence.

Host Cells

The invention also provides host cells expressing a flagellin polypeptide of the invention, for use in therapy. The examples demonstrate that *Enterococcus* strains such as MRx0518, which express *Enterococcus* flagellin of the invention, can activate TLR5 and therefore may have potent therapeutic effects. Host cells expressing flagellin polypeptides of the invention may be useful for producing flagellin polypeptide for inclusion in a therapeutic composition, or such host cells may be useful for administering to a patient, wherein they express the flagellin polypeptide to exert a direct therapeutic effect.

In preferred embodiments, the host cell of the invention expresses the flagellin polypeptide of the invention recombinantly. In other words, the host cell of the invention comprises a heterologous polynucleotide sequence that encodes the flagellin polypeptide of the invention. In certain embodiments, the host cell is not of the genus *Enterococcus*, is not of the species *Enterococcus gallinarum*, or is not of the strain MRx0518. In preferred embodiments, the host cell for expressing recombinant *Enterococcus* flagellin polypeptides is *E. coli*.

In alternative embodiments, wherein for example the host cell is for administration to a patient, the host cell is a probiotic strain, such as a *Lactobacillus* or *Bifidobacterium* strain.

In certain embodiments, the host cell comprises a polynucleotide sequence that encodes a flagellin polypeptide from the genus *Enterococcus*. In certain embodiments, the host cell comprises a polynucleotide sequence that encodes a flagellin polypeptide from the species *Enterococcus gallinarum*. In preferred embodiments, the host cell comprises a polynucleotide sequence that encodes a flagellin polypeptide from the strain MRx0518. In certain embodiments, the host cell comprises a vector, wherein the vector comprises a polynucleotide sequence that encodes a flagellin polypeptide from the genus *Enterococcus*.

In certain embodiments, the host cell comprises a polynucleotide sequence that encodes one or more of, preferably all of, the bacterial flagellar assembly genes FliD, FlgL, FlgK, FlgE, FliK, FlgD, FlgG, MotB, MotA, FliF, FliG, FliM, FliN, FlhA FlhB, FliH, FliI, FliO, FliP, FliQ, FliR, FliL, FliJ and FliS. In certain embodiments, the host cell of the invention expresses one or more of, preferably all of, the polypeptides FliD, FlgL, FlgK, FlgE, FliK, FlgD, FlgG, MotB, MotA, FliF, FliG, FliM, FliN, FlhA FlhB, FliH, FliI, FliO, FliP, FliQ, FliR, FliL, FliJ and FliS. In preferred embodiments, the host cell comprises a polynucleotide sequence that encodes a bacterial flagellar assembly comprising FliL and FlaG. In preferred embodiments, the host cell of the invention expresses the polypeptides FliL and FlaG.

Preferably, any cell expressing a flagellin polypeptide of the invention, and in particular any cell for administration to a patient, is effective at shedding flagellin polypeptide. The examples demonstrate that such cells induce a stronger TLR5 response. Flagellin can be "actively" shed during flagellum assembly, through leakage of its monomeric units. However, in most cases monomeric flagellin arise from the passive degradation of detached flagella. Flagellar detachment can occur following mechanical strain or as a voluntary process. In some bacterial species flagellin is glycosylated to enhance filament stability and prevent uncontrolled shedding, for example in *Shewanella oneidensis* [40]. In preferred embodiments, the flagellin expressed by the host cell is not glycosylated, to aid its shedding and disaggregation into the monomeric form.

In certain embodiments, the flagellin polypeptide and/or the bacterial flagellar assembly of the invention is easily shed from a host cell.

The ease of shedding of flagellin polypeptides and/or flagellar assemblies can be determined by separately growing i) cells expressing the flagellin of the invention and ii) one or more cells (e.g. 1, 2, 3, 4, 5, 10 or more than 10) expressing reference flagellins derived from the same or different strains belonging to the same bacterial species as the flagellin of the invention a) in a stationary phase for 18 hours using a 1% inoculum of the respective cells, then b) a late-log phase in which 10% inoculum of cells from the stationary phase are grown for 3 hours. 10 ml cultures of the cells expressing the flagellin of the invention and of the cells expressing reference flagellins can then be centrifuged at 5000×g for 5 minutes at room temperature to remove the bacterial pellet. The resulting supernatants can then be filtered (0.22 um) under sterile conditions. In embodiments in which the flagellin polypeptide and/or the bacterial flagellar assembly of the invention is a good shedder, the concentration of the flagellin protein in the supernatant derived from cells expressing the flagellin of the invention will be higher (e.g. 1.5× or higher, 2× or higher, 3× or higher, 4× or higher, 5× or higher, 7× or higher or 10× or higher) than the concentration of flagellin protein in the supernatants derived from the cells expressing reference flagellins.

In preferred embodiments, the host cell of the invention releases flagellin polypeptides and/or flagellar assemblies into its environment with requiring chemical or physical disruption. In preferred embodiments, culturing a host cell of the invention under conditions suitable for expression of the flagellin polypeptide results in flagellin polypeptide being released from the cell into its environment. The examples demonstrate that cells expressing flagellin polypeptides of the invention induce a stronger TLR5 response. In other embodiments, the host cells of the invention are good shedders of the bacterial flagellar assembly. In certain embodiments, the host cells of the invention are good shedders of bacterial flagellum filaments and in particular good shedders of flagellin polypeptides. In certain embodiments, the bacterial flagellar assembly of the invention actively sheds monomeric flagellin. In certain embodiments, the flagellum filament of the invention actively sheds monomeric flagellin. Monomeric flagellin is more effective at inducing TLR5 responses.

In certain embodiments, the invention provides a method for obtaining a flagellin polypeptide or flagellar assembly of the invention comprising culturing a cell expressing a flagellin polypeptide or flagellar assembly of the invention and culturing said flagellin polypeptide or flagellar assembly, without performing any step to remove separate flagellin polypeptide or flagellar assembly from the cell surface.

The process of flagellum (or flagellin) shedding is not currently associated with the expression of a specific subset genes and is likely to be heavily influenced by environmental conditions. However, a number of genes have been shown to be involved in flagellum rigidity and stability. For example in *Salmonella*, fliF and fliL mutants have been shown to shed flagella more easily when grown in viscous media [41,42]. In both cases, flagella broke near the distal rod [43]. Therefore, in preferred embodiments, the host cell does not express fliF and/or fliL. In other embodiments, the host cell does express fliL.

In certain embodiments, the host cells of the invention have been heat treated. The examples demonstrate that cells expressing flagellin polypeptides of the invention are still potently effective after heat treatment. In certain embodiments, the host cells of the invention are heat-stable to 80° C., for example can maintain activity following heating to 80° C. for, for example, 40 mins.

The invention further provides methods of producing the flagellin polypeptides of the invention by culturing the host cells under conditions permitting production of the flagellin polypeptides, and recovering the flagellin polypeptides so produced.

In certain embodiments, the host cell of the invention additionally expresses one or more antigens. Generally the antigen will be expressed recombinantly and will be heterologous to the host cell. The antigen may be part of a fusion polypeptide expressed with the flagellin polypeptide of the invention, or the host cell may separately express the flagellin and the antigen from different open reading frames. Therefore, the invention provides a host cell that expresses a flagellin polypeptide of the invention and a heterologous antigen. Exemplary antigens for use with the invention include: viral antigens, such as viral surface proteins; bacterial antigens, such as protein and/or saccharide antigens; fungal antigens; parasite antigens; and tumor antigens. Further antigens for expressing in a host cell with a flagellin of the invention include glycoprotein and lipoglycan antigens, archaea antigens, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 and habit forming substances, for example nicotine, alcohol or opiates.

Vectors, Plasmids and Other Nucleic Acids

The nucleic acid of the invention may be part of a vector i.e. part of a nucleic acid construct designed for transduction/transfection of one or more cell types. Vectors may be, for example, "expression vectors" which are designed for expression of a nucleotide sequence in a host cell, or "viral vectors" which are designed to result in the production of a recombinant virus or virus-like particle.

Alternatively, or in addition, the sequence or chemical structure of the nucleic acid may be modified compared to a naturally-occurring sequence which encodes a flagellin polypeptide. The sequence of the nucleic acid molecule may be modified, e.g. to increase the efficacy of expression or replication of the nucleic acid, or to provide additional stability or resistance to degradation. For example, the sequence of the nucleic acid molecule may be codon optimized for expression in a desired host, such as a mammalian (e.g. human) cell. Such modification with respect to codon usage may increase translation efficacy and half-life of the nucleic acid. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O]N), which may further increases translation efficacy.

The nucleic acids may comprise one or more nucleotide analogs or modified nucleotides. As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate. The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642, and many modified nucleosides and modified nucleotides are commercially available.

The invention further provides recombinant expression vectors capable of expressing a flagellin polypeptide. For example, the invention provides recombinant expression vectors comprising any of the nucleic acid molecules mentioned above.

The invention further provides host cells into which any of the vectors mentioned above have been introduced. The invention further provides methods of producing the flagellin polypeptides of the invention by culturing the host cells under conditions permitting production of the flagellin polypeptides, and recovering the flagellin polypeptides so produced.

A composition as disclosed herein comprising a nucleic acid sequence which encodes a flagellin polypeptides may be a nucleic acid-based therapeutic.

The nucleic acid may, for example, be RNA (i.e. an RNA-based therapeutic) or DNA (i.e. a DNA-based therapeutic, such as a plasmid DNA therapeutic). In certain embodiments, the nucleic acid-based therapeutic is an RNA-based therapeutic. In certain embodiments, the RNA-based therapeutic comprises a self-replicating RNA molecule. The self-replicating RNA molecule may be an alphavirus-derived RNA replicon.

Self-replicating RNA molecules are well known in the art and can be produced by using replication elements derived from, e.g., alphaviruses, and substituting the structural viral proteins with a nucleotide sequence encoding a protein of interest. A self-replicating RNA molecule is typically a + strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen (i.e. a flagellin polypeptide), or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are + stranded RNAs which lead to translation of a replicase (or replicase-transcriptase) after delivery to a cell. The replicase is translated as a polyprotein which auto cleaves to provide a replication complex which creates genomic − strand copies of the + strand delivered RNA. These − strand transcripts can themselves be transcribed to give further copies of the + stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons.

In certain embodiments, the self-replicating RNA molecule described herein encodes (i) a RNA-dependent RNA polymerase which can transcribe RNA from the self-replicating RNA molecule and (ii) a flagellin polypeptide. The polymerase can be an alphavirus replicase e.g. comprising one or more of alphavirus proteins nsP1, nsP2, nsP3 and nsP4.

The nucleic acid-based therapeutic may comprise a viral or a non-viral delivery system. The delivery system (also referred to herein as a delivery vehicle) may have adjuvant effects which enhance the immunogenicity of the encoded flagellin polypeptide. For example, the nucleic acid molecule may be encapsulated in liposomes, non-toxic biodegradable polymeric microparticles or viral replicon particles (VRPs), or complexed with particles of a cationic oil-in-water emulsion. In some embodiments, the nucleic acid-based therapeutic comprises a cationic nano-emulsion (CNE) delivery system or a lipid nanoparticle (LNP) delivery system. Alternatively, the nucleic acid-based therapeutic may comprise viral replicon particles. In other embodiments, the nucleic acid-based therapeutic may comprise a naked nucleic acid, such as naked RNA (e.g. mRNA), but delivery via LNPs is preferred.

In certain embodiments, the nucleic acid-based therapeutic comprises a cationic nano-emulsion (CNE) delivery system. CNE delivery systems and methods for their preparation are described in the art. In a CNE delivery system, the nucleic acid molecule (e.g. RNA) which encodes the antigen is complexed with a particle of a cationic oil-in-water emulsion. Cationic oil-in-water emulsions can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. Further details of useful CNEs can be found in the art.

Thus, in a nucleic acid-based therapeutic of the invention, an RNA molecule encoding a flagellin polypeptide may be complexed with a particle of a cationic oil-in-water emulsion. The particles typically comprise an oil core (e.g. a plant oil or squalene) that is in liquid phase at 25 C, a cationic lipid (e.g. phospholipid) and, optionally, a surfactant (e.g. sorbitan trioleate, polysorbate 80); polyethylene glycol can also be included. In some embodiments, the CNE comprises squalene and a cationic lipid, such as 1,2-dioleoyloxy-3-(trimethylammonio)propane (DOTAP). In some preferred embodiments, the delivery system is a non-viral delivery system, such as CNE, and the nucleic acid-based therapeutic comprises a self-replicating RNA (mRNA). This may be particularly effective in eliciting humoral and cellular immune responses. Advantages also include the absence of a limiting anti-vector immune response and a lack of risk of genomic integration.

LNP delivery systems and non-toxic biodegradable polymeric microparticles, and methods for their preparation are described in the art. LNPs are non virion liposome particles in which a nucleic acid molecule (e.g. RNA) can be encapsulated. The particles can include some external RNA (e.g. on the surface of the particles), but at least half of the RNA (and ideally all of it) is encapsulated. Liposomal particles can, for example, be formed of a mixture of zwitterionic, cationic and anionic lipids which can be saturated or unsaturated, for example; DSPC (zwitterionic, saturated), DlinDMA (cationic, unsaturated), and/or DMG (anionic, saturated). Preferred LNPs for use with the invention include an amphiphilic lipid which can form liposomes, optionally in combination with at least one cationic lipid (such as DOTAP, DSDMA, DODMA, DLinDMA, DLenDMA, etc.). A mixture of DSPC, DlinDMA, PEG- DMG and cholesterol is particularly effective. Other useful LNPs are disclosed in the art. In some embodiments, the LNPs are RV01 liposomes.

NF-κB

TLR signalling pathways culminate in the activation of the transcription factor nuclear factor-kappaB (NF-kB). NF-kB controls the expression of an array of inflammatory cytokine genes, including TNF-α. Flagellin induces the dimerization of TLR5, which subsequently recruits MyD88 and activates protein kinases, including IRAK1, IRAK2, IRAK4 and IRAK-M. The activation of these kinases leads to the nuclear localization of NF-kB, which is a proinflammatory cytokine [44].

As demonstrated in the examples (FIG. 18), compositions of the invention lead to an increase in expression of NF-κB. Since administration of the compositions of the invention increase the expression of the proinflammatory cytokine NF-κB, compositions of the invention may be useful in stimulating the immune response. In addition, compositions of the invention may be useful in the treatment of disease, in particular diseases characterised by reduced immune activation and/or diseases treatable by an increased immune response. In one embodiment, the compositions of the invention are for use as an immune stimulant by increasing the level and/or activity of NF-κB. In one embodiment, the compositions of the invention are for use in treating diseases characterised by reduced immune activation by increasing the level and/or activity of NF-κB. In one embodiment, the compositions of the invention are for use in treating diseases treatable by an increased immune response by increasing the level and/or activity of NF-κB.

In particular, compositions of the invention may be useful in the treatment of diseases characterised by a decrease in expression and/or activation of NF-κB. In one embodiment, the compositions of the invention are for use in treating diseases characterised by a decrease in expression and/or activation of NF-κB The activation of NF-kB is important for eliciting innate immune responses and the subsequent development of adaptive immune responses. Thus, agonists of TLRs, such as a flagellin, are likely to be useful as adjuvants to treat infectious diseases, allergies and tumours by promoting both innate and adaptive immune responses [44]. In one embodiment, the compositions of the invention are for use in treating infectious diseases, allergies and/or tumours. In one embodiment, the compositions of the invention are for use in treating infectious diseases, allergies and/or tumours by increasing the level and/or activity of NF-κB.

Treating Cancer

Toll-like receptors (TLRs) are membrane-bound receptors primarily expressed on innate immune cells that play key roles in both the innate and adaptive immune systems. TLRs respond to specific microbial pathogen-associated molecular patterns (PAMPs). TLRs sense bacterial cell wall components and TLR5 is known to recognise bacterial flagellin. Flagellin is the only known ligand for TLR5, a receptor protein expressed on the surface of a range of human cells, including epithelial cells, endothelial cells, macrophages, dendritic cells (DCs) and T cells [45-47]. Activation of TLR5 by bacterial flagellin leads to the activation of a variety of proinflammatory and immune response genes [15].

Activation of TLR5 by *S. typhimurium* flagellin is known to suppress cell proliferation and tumour growth [48]. A *S. typhimurium* strain engineered to secrete *Vibrio vulnificus* flagellin B (FlaB) has been shown to effectively suppress tumour growth and metastasis in mouse models and prolonged survival, through a two-step activation of the TLR4 and TLR5 signalling pathways [49]. The efficacy of flagellin polypeptides from other species to treat cancer is unknown. Assaying the ability of a compound to activate a TLR5 response shows that the compound may be effective at treating cancer.

Compositions comprising *Enterococcus gallinarum* strains, and in particular the strain MRx0518, are effective at treating and preventing cancer [50]. The inventors have surprisingly shown that flagellin polypeptides from the species *Enterococcus gallinarum* are able to stimulate a strong TLR5 response, which may contribute to the anti-cancer activity of *Enterococcus* strains. Flagellin polypeptides from *Enterococcus gallinarum* have large sequence dissimilarity with flagellin polypeptides from *S. typhimurium*. The examples show that flagellin polypeptides from the species *Enterococcus gallinarum* are able to produce a stronger TLR5 response than flagellin polypeptides from *S. typhimurium*. Thus, the inventors have shown that flagellin polypeptides from the genus *Enterococcus*, and in particular the species *Enterococcus gallinarum* are useful in therapy, and particularly effective in treating and preventing cancer.

TLR5 has been shown to be expressed by a number of different cancers, including breast, colorectal and gastric cancer. The examples show that flagellin polypeptides from the genus *Enterococcus* are able to produce a strong TLR5 response. Therefore, in certain embodiments the invention provides flagellin polypeptides from the genus *Enterococcus* for use in treating or preventing breast cancer, colorectal cancer or gastric cancer. In certain embodiments, the invention provides compositions comprising flagellin polypeptides from the genus *Enterococcus* for use in treating or preventing breast, colorectal or gastric cancer. In certain embodiments, the compositions of the invention are for use in reducing tumour size, reducing tumour growth, or reducing angiogenesis in breast, colorectal or gastric cancer. In a preferred embodiment, the invention provides a composition comprising flagellin polypeptides from the species *Enterococcus gallinarum*, for use in treating breast cancer. In a preferred embodiment, the invention provides a composition comprising flagellin polypeptides from the species *Enterococcus gallinarum*, for use in treating colorectal cancer. In a preferred embodiment, the invention provides a composition comprising flagellin polypeptides from the species *Enterococcus gallinarum*, for use in treating gastric cancer.

In certain embodiments, the invention provides compositions comprising flagellin polypeptides from the genus *Enterococcus* for use in treating or preventing TLR5 associated cancers.

The invention provides flagellin polypeptides from the genus *Enterococcus* for use in treating or preventing cancer. The invention also provides flagellin polypeptides the species *Enterococcus gallinarum* for use in treating or preventing cancer. More preferably, the invention provides flagellin polypeptide from the strain MRx0518, in particular with the sequence SEQ ID NO:1, for use in treating or preventing cancer.

The invention also provides compositions comprising the flagellin polypeptides of the invention. The invention also provides compositions comprising a polynucleotide sequence encoding a flagellin polypeptide of the invention. The invention also provides a host cell that expresses a flagellin polypeptide of the invention. In addition, the invention also provides compositions comprising a host cell, wherein the host cell comprises a polynucleotide sequence that encodes a flagellin polypeptide of the invention.

In certain embodiments, treatment with the compositions of the invention results in a reduction in tumour size or a reduction in tumour growth. In certain embodiments, the compositions of the invention are for use in reducing tumour size or reducing tumour growth. The compositions of the invention may be effective for reducing tumour size or growth. In certain embodiments, the compositions of the invention are for use in treating patients with solid tumours. In certain embodiments, the compositions of the invention are for use in reducing or preventing angiogenesis in the treatment of cancer. The compositions of the invention may have an effect on the immune or inflammatory systems, which have central roles in angiogenesis. In certain embodiments, the compositions of the invention are for use in preventing metastasis.

In certain embodiments, the compositions of the invention are for use in treating or preventing breast cancer. Reference [50] demonstrates that *Enterococcus* strains have a potent effect against breast cancer, so following the data in the present application, flagellin polypeptides of the invention may be particularly effective against breast cancer. In certain embodiments, the compositions of the invention are for use in reducing tumour size, reducing tumour growth, or reducing angiogenesis in the treatment of breast cancer. In preferred embodiments the cancer is mammary carcinoma. In preferred embodiments the cancer is stage IV breast cancer.

In certain embodiments, the compositions of the invention are for use in treating or preventing lung cancer. Reference [50] demonstrates that *Enterococcus* strains have a potent effect against lung cancer, so following the data in the present application, flagellin polypeptides of the invention may be particularly effective against lung cancer. In certain embodiments, the compositions of the invention are for use in reducing tumour size, reducing tumour growth, or reducing angiogenesis in the treatment of lung cancer. In preferred embodiments the cancer is lung carcinoma.

In certain embodiments, the compositions of the invention are for use in treating or preventing liver cancer. Reference [50] demonstrates that *Enterococcus* strains have a potent effect against liver cancer, so following the data in the present application, flagellin polypeptides of the invention may be particularly effective against liver cancer. In certain embodiments, the compositions of the invention are for use in reducing tumour size, reducing tumour growth, or reducing angiogenesis in the treatment of liver cancer. In preferred embodiments the cancer is hepatoma (hepatocellular carcinoma).

In certain embodiments, the compositions of the invention are for use in treating or preventing colorectal cancer. Reference [50] demonstrates that *Enterococcus* strains have a potent effect against colorectal cancer, so following the data in the present application, flagellin polypeptides of the invention may be particularly effective against colorectal cancer. In certain embodiments, the compositions of the invention are for use in reducing tumour size, reducing tumour growth, or reducing angiogenesis in the treatment of colorectal cancer. In preferred embodiments the cancer is colorectal adenocarcinoma.

In certain embodiments, the compositions of the invention are for use in treating or preventing colon cancer. Reference [50] demonstrates that *Enterococcus* strains have a potent effect against colon cancer, so following the data in the present application, flagellin polypeptides of the invention may be particularly effective against colon cancer. In certain embodiments, the compositions of the invention are for use in reducing tumour size, reducing tumour growth, or reducing angiogenesis in the treatment of colon cancer. In preferred embodiments the cancer is colon adenocarcinoma.

In certain embodiments, the compositions of the invention are for use in treating or preventing rectal cancer. Reference [50] demonstrates that *Enterococcus* strains have a potent effect against rectal cancer, so following the data in the present application, flagellin polypeptides of the invention may be particularly effective against rectal cancer. In certain embodiments, the compositions of the invention are for use in reducing tumour size, reducing tumour growth, or reducing angiogenesis in the treatment of rectal cancer. In preferred embodiments the cancer is rectal adenocarcinoma. In a preferred embodiment, the invention provides a composition comprising flagellin polypeptides from the species *Enterococcus gallinarum*, for use in treating rectal cancer.

In certain embodiments, the compositions of the invention are for use in treating or preventing gastric cancer. Gastric carcinomas have been show to express high levels of TLR5 and that treatment with flagellin elicits a potent anti-tumour activity [51]. The examples show that the flagellin polypeptides of the invention are able to produce a strong TLR5 response, therefore flagellin polypeptides of the invention may be particularly effective against gastric cancer. In certain embodiments, the compositions of the invention are for use in reducing tumour size, reducing tumour growth, or reducing angiogenesis in the treatment of gastric cancer. In preferred embodiments the cancer is gastric adenocarcinoma. In a preferred embodiment, the invention provides a composition comprising flagellin polypeptides from the species *Enterococcus gallinarum*, for use in treating gastric cancer.

In certain embodiments, the compositions of the invention are for use in treating or preventing melanoma. Flagellin from *S. typhimurium*, in combination with the major histocompatibility complex class II-restricted P10 peptide, has been shown to reduce the number of lung metastasis in a murine melanoma model [52]. The examples show that the flagellin polypeptides of the invention are able to produce a stronger TLR5 response than *S. typhimurium*, therefore flagellin polypeptides of the invention may be particularly effective against melanoma. In certain embodiments, the compositions of the invention are for use in reducing tumour size, reducing tumour growth, or reducing angiogenesis in the treatment of melanoma. In a preferred embodiment, the invention provides a composition comprising flagellin polypeptides from the species *Enterococcus gallinarum*, for use in treating melanoma.

In certain embodiments, the compositions of the invention are for use in treating or preventing neuroblastoma. Activation of TLR5 by *S. typhimurium* flagellin is known to suppress cell proliferation and tumour growth [53]. The examples show that the flagellin polypeptides of the invention are able to produce a stronger TLR5 response than *S. typhimurium*, therefore flagellin polypeptides of the invention may be particularly effective against neuroblastoma. In certain embodiments, the compositions of the invention are for use in reducing tumour size, reducing tumour growth, or reducing angiogenesis in the treatment of neuroblastoma. In a preferred embodiment, the invention provides a composition comprising flagellin polypeptides from the species *Enterococcus gallinarum*, for use in treating neuroblastoma.

In some embodiments, the cancer is of the intestine. In some embodiments, the cancer is of a part of the body which is not the intestine. In some embodiments, the cancer is not cancer of the intestine. In some embodiments, the cancer is not colorectal cancer. In some embodiments, the cancer is not cancer of the small intestine. In some embodiments, the treating or preventing occurs at a site other than at the intestine. In some embodiments, the treating or preventing occurs at the intestine and also at a site other than at the intestine.

Expression of TLR5 has been detected in haematological cancer cell lines, including multiple myeloma [54] and acute myeloid leukaemia [55]. The inventors have demonstrated in the examples that flagellin polypeptides from the genus *Enterococcus* are particularly effective at activating a strong TLR5 response. Flagellin polypeptides from the genus *Enterococcus* may therefore be useful at treating or preventing haematological cancers, such as multiple myeloma and acute myeloid leukaemia, which express TLR5. Therefore, in certain embodiments the invention provides compositions comprising flagellin polypeptides from the genus *Enterococcus* for use in treating or preventing haematological malignancies, such as multiple myeloma, acute and chronic leukemias such as acute myeloid leukaemia, acute lymphoblastic leukemia, acute myelogenous leukemia, chronic lymphocytic leukemia, chronic myelogenous leukemia and acute monocytic leukemia, lymphomas, such as Hodgkin's lymphomas and Non-Hodgkin's lymphomas, and myelodysplastic syndromes. In a preferred embodiment, the invention provides a composition comprising flagellin polypeptides from the species *Enterococcus gallinarum*, for use in treating acute myeloid leukaemia.

In certain embodiments the invention provides compositions comprising flagellin polypeptides from the genus *Enterococcus* for use in treating or preventing multiple myeloma. In certain embodiments, the invention provides compositions comprising flagellin polypeptides from the genus *Enterococcus* for use in treating or preventing acute myeloid leukaemia. In a preferred embodiment, the invention provides a composition comprising flagellin polypeptides from the species *Enterococcus gallinarum*, for use in treating multiple myeloma.

Various TLR agonists have been tested in a wide array of tumour models and clinical trials [56]. For example, the TLR5 agonist CBLB502 has been shown to promote tumour clearance in mice models of T and B cell lymphomas [57]. Systemic administration of the TLR5 agonist entolimod (a pharmacologically optimized flagellin derivative) suppressed liver metastasis of colorectal cells in mice models. The liver shows the strongest TLR5 activation response following the administration of the TLR5 agonist entolimod [58]. The inventors have demonstrated in the examples that flagellin polypeptides from the genus *Enterococcus* act as strong TLR5 agonists. Therefore, flagellin polypeptides from the genus *Enterococcus* may be particularly effective at treating or preventing T and B cell lymphomas, colorectal and liver cancer. In certain embodiments, the compositions of the invention are for use in treating or preventing T and B cell lymphomas. In a preferred embodiment, the invention provides a composition comprising flagellin polypeptides from the species *Enterococcus gallinarum*, for use in treating T and B cell lymphomas.

In other embodiments, the compositions of the invention may be useful in treating or preventing metastasis. In other embodiments, the compositions of the invention may be useful in treating metastatic cancer. In other embodiments, the compositions of the invention may be useful in treating advanced cancer. In certain embodiments, the invention provides compositions comprising flagellin polypeptides from the genus *Enterococcus* for use in treating, reducing or preventing metastasis. In certain embodiments, the compositions of the invention may decrease or prevent metastatic growth. In a preferred embodiment, the invention provides a composition comprising flagellin polypeptides from the species *Enterococcus gallinarum*, for use in treating or preventing metastasis. In a preferred embodiment, the invention provides a composition comprising flagellin polypeptides from the species *Enterococcus gallinarum*, for use in treating or preventing metastatic cancer. In a preferred embodiment, the invention provides a composition comprising flagellin polypeptides from the species *Enterococcus gallinarum*, for use in treating or preventing advanced cancer.

In certain embodiments, the compositions of the invention are for use in treating or preventing carcinoma.

*Vibrio vulnificus* flagellin B (FlaB) has been shown to effectively suppress tumour growth through a two-step activation of the TLR4 and TLR5 signalling pathways. In certain embodiments, the flagellin polypeptides of the invention can activate the TLR4 and TLR5 signalling pathways. In other embodiments the flagellin polypeptides of the invention only activate the TLR5 signalling pathway.

In certain embodiments, the flagellin polypeptides of the invention can activate NFκB signalling pathways. In certain embodiments, host cells of the invention can activate the TLR9 signalling pathways. Reference [59] shows that synergy between flagellin and the TLR9 agonist CpG-containing oligodeoxynucleotides leads to tumour suppression. In certain embodiments, the host cells of the invention of the invention can activate the TLR5 and TLR9 signalling pathways. In certain such embodiments, the composition of the invention comprises CpG-containing oligodeoxynucleotides or is administered in combination with CpG-containing oligodeoxynucleotides.

The therapeutic effects of the compositions of the invention on cancer may be mediated by a pro-inflammatory mechanism. Activation of TLR5 by flagellin initiates a proinflammatory signal cascade. Reference [59] shows that the interaction of *S. typhimurium* flagellin with highly immunogenic tumours induces a Th1 response and suppression of Tregs, resulting in the inhibition of tumour growth. In contrast, the growth rate of weakly immunogenic tumours was not affected by flagellin administration. Therefore, in certain embodiments, the flagellin polypeptides and compositions of the invention are for use in treating immunogenic tumours, in particular highly immunogenic tumours. In certain embodiments, the compositions of the invention are for use in promoting inflammation in the treatment of cancer. In preferred embodiments, the compositions of the invention are for use in promoting Th1 inflammation in the treatment of cancer. Th1 cells produce IFNγ and have potent anti-cancer effects [60]. In certain embodiments, the compositions of the invention are for use in treating an early-stage cancer, such as a cancer that has not metastasized, or a stage 0 or stage 1 cancer. Promoting inflammation may be more effective against early-stage cancers [60].

Reference [59] shows that administration of flagellin after tumour transplantation significantly inhibited growth of antigenic tumours. The differing effects of flagellin on tumour growth are correlated with the immune response that is induced. Flagellin administration after transplantation was associated with an increased IFN-γ:IL-4 ratio and the decreased frequency of CD4+CD25+T regulatory cells. Therefore, in certain embodiments, the flagellin polypeptides and compositions of the invention increase the IFN-γ: IL-4 ratio. In certain embodiments, the flagellin polypeptides and compositions of the invention decrease the frequency of CD4+CD25+T regulatory cells. In other embodiments, the flagellin polypeptides and compositions of the invention do not decrease the IFN-γ:IL-4 ratio and increase CD4+CD25+ T cell frequency. Inflammation can have a cancer-suppressive effect [60] and pro-inflammatory cytokines such as TNFα are being investigated as cancer therapies [61]. The up-regulation of genes such as TNF may indicate that the compositions of the invention may be useful for treating cancer via a similar mechanism. The up-regulation of CXCR3 ligands (CXCL9, CXCL10) and IFNγ-inducible genes (IL-32) may indicate that the compositions of the invention elicit an IFNγ-type response. IFNγ is a potent macrophage-activating factor that can stimulate tumirocidal activity [62], and CXCL9 and CXCL10, for example, also have anti-cancer effects [63-65].

In certain embodiments, the compositions of the invention are for use in promoting inflammation to enhance the effect of a second anti-cancer agent. In certain embodiments, the treatment or prevention of cancer comprises increasing the level of expression of one or more cytokines. For example, in certain embodiments, the treatment or prevention of cancer comprises increasing the level of expression of one or more of IL-1β, IL-6 and TNF-α, for example, IL-1β and IL-6, IL-1β and TNF-α, IL-6 and TNF-α or all three of IL-1β, IL-6 and TNF-α. Increases in levels of expression of any of IL-1β, IL-6 and TNF-α are known to be indicative of efficacy in treatment of cancer.

In certain embodiments, the compositions of the invention are for use in treating a patient that has previously received chemotherapy. In certain embodiments, the compositions of the invention are for use in treating a patient that has not tolerated a chemotherapy treatment. The compositions of the invention may be particularly suitable for such patients.

In certain embodiments, the compositions of the invention are for preventing relapse. The compositions of the invention may be suitable for long-term administration. In certain embodiments, the compositions of the invention are for use in preventing progression of cancer.

In certain embodiments, the compositions of the invention are for use in treating non-small-cell lung carcinoma. In certain embodiments, the compositions of the invention are for use in treating small-cell lung carcinoma. In certain embodiments, the compositions of the invention are for use in treating squamous-cell carcinoma. In certain embodiments, the compositions of the invention are for use in treating adenocarcinoma. In certain embodiments, the compositions of the invention are for use in treating glandular tumors, carcinoid tumors, or undifferentiated carcinomas.

In certain embodiments, the compositions of the invention are for use in treating hepatoblastoma, cholangiocarcinoma, cholangiocellular cystadenocarcinoma or liver cancer resulting from a viral infection.

In certain embodiments, the compositions of the invention are for use in treating invasive ductal carcinoma, ductal carcinoma in situ or invasive lobular carcinoma.

In further embodiments, the compositions of the invention are for use in treating or preventing acute lymphoblastic leukemia (ALL), acute myeloid leukemia, adrenocortical carcinoma, basal-cell carcinoma, bile duct cancer, bladder cancer, bone tumor, osteosarcoma/malignant fibrous histiocytoma, brainstem glioma, brain tumor, cerebellar astrocytoma, cerebral astrocytoma/malignant glioma, ependymoma, medulloblastoma, supratentorial primitive neuroectodermal tumors, breast cancer, bronchial adenomas/carcinoids, Burkitt's lymphoma, carcinoid tumor, cervical cancer, chronic lymphocytic leukemia, chronic myelogenous leukemia, chronic myeloproliferative disorders, colon cancer, cutaneous T-cell lymphoma, endometrial cancer, ependymoma, esophageal cancer, Ewing's sarcoma, intraocular melanoma, retinoblastoma, gallbladder cancer, gastric cancer, gastrointestinal carcinoid tumor, gastrointestinal stromal tumor (GIST), germ cell tumor, glioma, childhood visual pathway and hypothalamic, Hodgkin lymphoma, melanoma, islet cell carcinoma, Kaposi sarcoma, renal cell cancer, laryngeal cancer, leukaemias, lymphomas, mesothelioma, neuroblastoma, non-Hodgkin lymphoma, oropharyngeal cancer, osteosarcoma, ovarian cancer, pancreatic cancer, parathyroid cancer, pharyngeal cancer, pituitary adenoma, plasma cell neoplasia, prostate cancer, renal cell carcinoma, retinoblastoma, sarcoma, testicular cancer, thyroid cancer, or uterine cancer.

The compositions of the invention may be particularly effective when used in combination with further therapeutic agents. The immune-modulatory effects of the compositions of the invention may be effective when combined with more direct anti-cancer agents. Therefore, in certain embodiments, the invention provides a composition comprising a flagellin polypeptide from the genus *Enterococcus* (or encoding polynucleotide or expressing host cell) and an anticancer agent. In preferred embodiments the anticancer agent is an immune checkpoint inhibitor, a targeted antibody immunotherapy, a CAR-T cell therapy, an oncolytic virus, or a cytostatic drug. Preferably the anti-cancer agent is Keytruda (pembrolizumab, Merck). In further preferred embodiments, the composition comprises an anti-cancer agent selected from the group consisting of: Yervoy (ipilimumab, BMS); Opdivo (nivolumab, BMS); MEDI4736 (AZ/MedImmune); MPDL3280A (Roche/Genentech); Tremelimumab (AZ/MedImmune); CT-011 (pidilizumab, CureTech); BMS-986015 (lirilumab, BMS); MEDI0680 (AZ/MedImmune); MSB-0010718C (Merck); PF-05082566 (Pfizer); MEDI6469 (AZ/MedImmune); BMS-986016 (BMS); BMS-663513 (urelumab, BMS); IMP321 (Prima Biomed); LAG525 (Novartis); ARGX-110 (arGEN-X); PF-05082466 (Pfizer); CDX-1127 (varlilumab; CellDex Therapeutics); TRX-518 (GITR Inc.); MK-4166 (Merck); JTX-2011 (Jounce Therapeutics); ARGX-115 (arGEN-X); NLG-9189 (indoximod, NewLink Genetics); INCB024360 (Incyte); IPH2201 (Innate Immotherapeutics/AZ); NLG-919 (NewLink Genetics); anti-VISTA (JnJ); Epacadostat (INCB24360, Incyte); F001287 (Flexus/BMS); CP 870893 (University of Pennsylvania); MGA271 (Macrogenix); Emactuzumab (Roche/Genentech); Galunisertib (Eli Lilly); Ulocuplumab (BMS); BKT140/BL8040 (Biokine Therapeutics); Bavituximab (Peregrine Pharmaceuticals); CC 90002 (Celgene); 852A (Pfizer); VTX-2337 (VentiRx Pharmaceuticals); IMO-2055 (Hybridon, Idera Pharmaceuticals); LY2157299 (Eli Lilly); EW-7197 (Ewha Women's University, Korea); Vemurafenib (Plexxikon); Dabrafenib (Genentech/GSK); BMS-777607 (BMS); BLZ945 (Memorial Sloan-Kettering Cancer Centre); Unituxin (dinutuximab, United Therapeutics Corporation); Blincyto (blinatumomab, Amgen); Cyramza (ramucirumab, Eli Lilly); Gazyva (obinutuzumab, Roche/Biogen); Kadcyla (ado-trastuzumab emtansine, Roche/Genentech); Perjeta (pertuzumab, Roche/Genentech); Adcetris (brentuximab vedotin, Takeda/Millennium); Arzerra (ofatumumab, GSK); Vectibix (panitumumab, Amgen); Avastin (bevacizumab, Roche/Genentech); Erbitux (cetuximab, BMS/Merck); Bexxar (tositumomab-I131, GSK); Zevalin (ibritumomab tiuxetan, Biogen); Campath (alemtuzumab, Bayer); Mylotarg (gemtuzumab ozogamicin, Pfizer); Herceptin (trastuzumab, Roche/Genentech); Rituxan (rituximab, Genentech/Biogen); volociximab (Abbvie); Enavatuzumab (Abbvie); ABT-414 (Abbvie); Elotuzumab (Abbvie/BMS); ALX-0141 (Ablynx); Ozaralizumab (Ablynx); Actimab-C (Actinium); Actimab-P (Actinium); Milatuzumab-dox (Actinium);

Emab-SN-38 (Actinium); Naptumonmab estafenatox (Active Biotech); AFM13 (Affimed); AFM11 (Affimed); AGS-16C3F (Agensys); AGS-16M8F (Agensys); AGS-22ME (Agensys); AGS-15ME (Agensys); GS-67E (Agensys); ALXN6000 (samalizumab, Alexion); ALT-836 (Altor Bioscience); ALT-801 (Altor Bioscience); ALT-803 (Altor Bioscience); AMG780 (Amgen); AMG 228 (Amgen); AMG820 (Amgen); AMG172 (Amgen); AMG595 (Amgen); AMG110 (Amgen); AMG232 (adecatumumab, Amgen); AMG211 (Amgen/MedImmune); BAY20-10112 (Amgen/Bayer); Rilotumumab (Amgen); Denosumab (Amgen); AMP-514 (Amgen); MEDI575 (AZ/MedImmune); MEDI3617 (AZ/MedImmune); MEDI6383 (AZ/MedImmune); MEDI551 (AZ/MedImmune); Moxetumomab pasudotox (AZ/MedImmune); MEDI565 (AZ/MedImmune); MEDI0639 (AZ/MedImmune); MEDI0680 (AZ/MedImmune); MEDI562 (AZ/MedImmune); AV-380 (AVEO); AV203 (AVEO); AV299 (AVEO); BAY79-4620 (Bayer); Anetumab ravtansine (Bayer); vantictumab (Bayer); BAY94-9343 (Bayer); Sibrotuzumab (Boehringer Ingleheim); BI-836845 (Boehringer Ingleheim); B-701 (BioClin); BIIB015 (Biogen); Obinutuzumab (Biogen/Genentech); BI-505 (Bioinvent); BI-1206 (Bioinvent); TB-403 (Bioinvent); BT-062 (Biotest) BIL-010t (Biosceptre); MDX-1203 (BMS); MDX-1204 (BMS); Necitumumab (BMS); CAN-4 (Cantargia AB); CDX-011 (Celldex); CDX1401 (Celldex); CDX301 (Celldex); U3-1565 (Daiichi Sankyo); patritumab (Daiichi Sankyo); tigatuzumab (Daiichi Sankyo); nimotuzumab (Daiichi Sankyo); DS-8895 (Daiichi Sankyo); DS-8873 (Daiichi Sankyo); DS-5573 (Daiichi Sankyo); MORab-004 (Eisai); MORab-009 (Eisai); MORab-003 (Eisai); MORab-066 (Eisai); LY3012207 (Eli Lilly); LY2875358 (Eli Lilly); LY2812176 (Eli Lilly); LY3012217 (Eli Lilly); LY2495655 (Eli Lilly); LY3012212 (Eli Lilly); LY3012211 (Eli Lilly); LY3009806 (Eli Lilly); cixutumumab (Eli Lilly); Flanvotumab (Eli Lilly); IMC-TR1 (Eli Lilly); Ramucirumab (Eli Lilly); Tabalumab (Eli Lilly); Zanolimumab (Emergent Biosolution); FG-3019 (FibroGen); FPA008 (Five Prime Therapeutics); FP-1039 (Five Prime Therapeutics); FPA144 (Five Prime Therapeutics); catumaxomab (Fresenius Biotech); IMAB362 (Ganymed); IMAB027 (Ganymed); HuMax-CD74 (Genmab); HuMax-TFADC (Genmab); GS-5745 (Gilead); GS-6624 (Gilead); OMP-21M18 (demcizumab, GSK); mapatumumab (GSK); IMGN289 (ImmunoGen); IMGN901 (ImmunoGen); IMGN853 (ImmunoGen); IMGN529 (ImmunoGen); IMMU-130 (Immunomedics); milatuzumab-dox (Immunomedics); IMMU-115 (Immunomedics); IMMU-132 (Immunomedics); IMMU-106 (Immunomedics); IMMU-102 (Immunomedics); Epratuzumab (Immunomedics); Clivatuzumab (Immunomedics); IPH41 (Innate Immunotherapeutics); Daratumumab (Janssen/Genmab); CNTO-95 (Intetumumab, Janssen); CNTO-328 (siltuximab, Janssen); KB004 (KaloBios); mogamulizumab (Kyowa Hakko Kirrin); KW-2871 (ecromeximab, Life Science); Sonepcizumab (Lpath); Margetuximab (Macrogenics); Enoblituzumab (Macrogenics); MGD006 (Macrogenics); MGF007 (Macrogenics); MK-0646 (dalotuzumab, Merck); MK-3475 (Merck); Sym004 (Symphogen/Merck Serono); DI17E6 (Merck Serono); MOR208 (Morphosys); MOR202 (Morphosys); Xmab5574 (Morphosys); BPC-1C (ensituximab, Precision Biologics); TAS266 (Novartis); LFA102 (Novartis); BHQ880 (Novartis/Morphosys); QGE031 (Novartis); HCD122 (lucatumumab, Novartis); LJM716 (Novartis); AT355 (Novartis); OMP-21M18 (Demcizumab, OncoMed); OMP52M51 (Oncomed/GSK); OMP-59R5 (Oncomed/GSK); vanticumab (Oncomed/Bayer); CMC-544 (inotuzumab ozogamicin, Pfizer); PF-03446962 (Pfizer); PF-04856884 (Pfizer); PSMA-ADC (Progenics); REGN1400 (Regeneron); REGN910 (nesvacumab, Regeneron/Sanofi); REGN421 (enoticumab, Regeneron/Sanofi); RG7221, RG7356, RG7155, RG7444, RG7116, RG7458, RG7598, RG7599, RG7600, RG7636, RG7450, RG7593, RG7596, DCDS3410A, RG7414 (parsatuzumab), RG7160 (imgatuzumab), RG7159 (obinutuzumab), RG7686, RG3638 (onartuzumab), RG7597 (Roche/Genentech); SAR307746 (Sanofi); SAR566658 (Sanofi); SAR650984 (Sanofi); SAR153192 (Sanofi); SAR3419 (Sanofi); SAR256212 (Sanofi), SGN-LIV1A (lintuzumab, Seattle Genetics); SGN-CD33A (Seattle Genetics); SGN-75 (vorsetuzumab mafodotin, Seattle Genetics); SGN-19A (Seattle Genetics) SGN-CD70A (Seattle Genetics); SEA-CD40 (Seattle Genetics); ibritumomab tiuxetan (Spectrum); MLN0264 (Takeda); ganitumab (Takeda/Amgen); CEP-37250 (Teva); TB-403 (Thrombogenic); VB4-845 (Viventia); Xmab2512 (Xencor); Xmab5574 (Xencor); nimotuzumab (YM Biosciences); Carlumab (Janssen); NY-ESO TCR (Adaptimmune); MAGE-A-10 TCR (Adaptimmune); CTL019 (Novartis); JCAR015 (Juno Therapeutics); KTE-C19 CAR (Kite Pharma); UCART19 (Cellectis); BPX-401 (Bellicum Pharmaceuticals); BPX-601 (Bellicum Pharmaceuticals); ATTCK20 (Unum Therapeutics); CAR-NKG2D (Celyad); Onyx-015 (Onyx Pharmaceuticals); H101 (Shanghai Sunwaybio); DNX-2401 (DNAtrix); VCN-01 (VCN Biosciences); Colo-Adl (PsiOxus Therapeutics); ProstAtak (Advantagene); Oncos-102 (Oncos Therapeutics); CG0070 (Cold Genesys); Pexa-vac (JX-594, Jennerex Biotherapeutics); GL-ONC1 (Genelux); T-VEC (Amgen); G207 (Medigene); HF10 (Takara Bio); SEPREHVIR (HSV1716, Virttu Biologics); OrienX010 (OrienGene Biotechnology); Reolysin (Oncolytics Biotech); SVV-001 (Neotropix); Cacatak (CVA21, Viralytics); Alimta (Eli Lilly), cisplatin, oxaliplatin, irinotecan, folinic acid, methotrexate, cyclophosphamide, 5-fluorouracil, Zykadia (Novartis), Tafinlar (GSK), Xalkori (Pfizer), Iressa (AZ), Gilotrif (Boehringer Ingelheim), Tarceva (Astellas Pharma), Halaven (Eisai Pharma), Veliparib (Abbvie), AZD9291 (AZ), Alectinib (Chugai), LDK378 (Novartis), Genetespib (Synta Pharma), Tergenpumatucel-L (NewLink Genetics), GV1001 (Kael-GemVax), Tivantinib (ArQule); Cytoxan (BMS); Oncovin (Eli Lilly); Adriamycin (Pfizer); Gemzar (Eli Lilly); Xeloda (Roche); Ixempra (BMS); Abraxane (Celgene); Trelstar (Debiopharm); Taxotere (Sanofi); Nexavar (Bayer); IMIVIU-132 (Immunomedics); E7449 (Eisai); Thermodox (Celsion); Cometriq (Exellxis); Lonsurf (Taiho Pharmaceuticals); Camptosar (Pfizer); UFT (Taiho Pharmaceuticals); and TS-1 (Taiho Pharmaceuticals).

In further preferred embodiments, flagellin polypeptides are administered in combination (contemporaneously or sequentially) with CpG-containing oligodeoxynucleotides, which have shown useful effects with other flagellins [59].

In some embodiments, a flagellin polypeptide from the genus *Enterococcus* is the only therapeutically active agent(s) in a composition of the invention.

Protection Against Toxic Chemical, Pathogen or Radiation Exposure

In certain embodiments, the invention provides a flagellin polypeptide from the genus *Enterococcus*, preferably a flagellin polypeptide from the species *Enterococcus gallinarum*, preferably a flagellin polypeptide from the strain MRx0518, for use in preventing or treating symptoms associated with toxic chemical, pathogen or radiation exposure. The flagellin of the invention may be administered to subjects at risk of toxic chemical, pathogen or radiation exposure, or subjects recently exposed to toxic chemicals, pathogens or radiation, for example subjects exposed 1, 2, 3, 4, or 5 hours previously.

Sudden exposure of human populations to chemicals, pathogens, or radiation has the potential to result in substantial morbidity. One strategy to protect human populations is to activate innate host defence pathways, particularly those that rapidly induce cytoprotective and/or antimicrobial gene expression. A lot of work in this area has focused on the TLR4 agonist LPS/endotoxin, however LPS administration can lead to severe inflammatory pathologies, including sepsis or severe lung injury. In addition, LPS is a poor stimulator of epithelial cells, which are the first cells that interact with the pathogen or chemical challenge.

Flagellin stimulates host defence in a variety of organisms, including mammals, insects, and plants. In contrast to LPS, flagellin is a potent activator of innate immune signalling pathways in epithelial cells but has generally observed to be a poor activator of hemopoietic cells, such as macrophages and dendritic cells. *S. typhimurium* flagellin has been observed to not stimulate significant levels of "master" proinflammatory cytokines, such as TNF-α, that mediate the adverse effects associated with LPS. *S. typhimurium* flagellin has been observed to activate TLR5 mediated innate immunity in mice, protecting the mice against chemical, pathogen or radiation exposure [66].

Administration of *S. typhimurium* flagellin has been shown to protect against radiation exposure via a mechanism requiring TLR5 [66]. Optimal protection was observed when flagellin was administered prophylactically 2 hours before radiation, but a significant degree of protection was still observed if the flagellin was administered up to 4 h following irradiation. The examples show that flagellin polypeptides from the genus *Enterococcus* are able to stimulate a stronger TLR5 response than *S. typhimurium*. Thus, the inventors have shown that flagellin polypeptides from the genus *Enterococcus*, and in particular the species *Enterococcus gallinarum* may be useful as radioprotective agents.

The invention provides flagellin polypeptides from the genus *Enterococcus* for use as radioprotective agents. The invention also provides flagellin polypeptides the species *Enterococcus gallinarum* for use as radioprotective agents. More preferably, the invention provides flagellin polypeptide from the strain MRx0518, in particular with the sequence SEQ ID NO:1, for use as radioprotective agents.

Treatment with the TLR5 agonist Entolimod has also been shown to reduce radiation-induced damage in all three of the major types of radiosensitive tissues: hemato-poietic, gastrointestinal and skin. It has also been shown to mitigate radiation-induced epithelial damage in a mouse model of head and neck radiation [67]. The examples show that flagellin polypeptides from the genus *Enterococcus* act as a potent TLR5 agonist. Thus, the inventors have shown that flagellin polypeptides from the genus *Enterococcus*, and in particular the species *Enterococcus gallinarum* may be useful at reducing radiation-induced damage. In certain embodiments, compositions comprising flagellin polypeptides from the genus *Enterococcus* are for use in reducing radiation-induced damage in hemato-poietic, gastrointestinal or skin tissues. In certain embodiments, compositions comprising flagellin polypeptides from the genus *Enterococcus* are for use in reducing radiation-induced epithelial damage. In a preferred embodiment, the invention provides a composition comprising flagellin polypeptides from the species *Enterococcus gallinarum* for use in reducing radiation-induced damage.

In certain embodiments, the composition of the invention may be administered, preferably orally, prior to radiotherapy. In certain embodiments, the composition of the invention may be administered, preferably orally, shortly after radiotherapy. In certain embodiments, the compositions of the invention are to be administered to a patient that has recently undergone radiotherapy, or that is scheduled to undergo radiotherapy.

In preferred embodiments, the flagellin polypeptides from the genus *Enterococcus* are administered before the irradiation exposure. In other embodiments, the flagellin polypeptides from the genus *Enterococcus* are administered after the radiation exposure, preferably within 4 hours following exposure.

Treating Bacterial Infections

Administration of *S. typhimurium* flagellin has been shown stimulate immune responses to bacterial infection. Reference [68] shows that the prophylactic intranasal administration of *S. typhimurium* flagellin with an antibiotic protects mice against respiratory *Streptococcus pneumoniae* bacteria, while reference [66] shows that oral administration of *S. typhimurium* flagellin 2 hours prior to infection with *S. typhimurium* reduced mortality. Flagellin induced these responses by activating the TLR5 innate immune response. The examples show that flagellin polypeptides from the genus *Enterococcus* are able to stimulate a stronger TLR5 response than *S. typhimurium*. Thus, the inventors have shown that flagellin polypeptides from the genus *Enterococcus*, and in particular the species *Enterococcus gallinarum* can be useful in the treatment or prevention of bacterial infections.

The invention provides flagellin polypeptides from the genus *Enterococcus* for use in treating or preventing bacterial infections. The invention also provides flagellin polypeptides the species *Enterococcus gallinarum* for use in treating or preventing bacterial infections. More preferably, the invention provides flagellin polypeptide from the strain MRx0518, in particular with the sequence SEQ ID NO:1, for use in treating or preventing bacterial infections.

In certain embodiments, the flagellin polypeptides from the genus *Enterococcus* are used in combination with an antibiotic for use in treating bacterial infections. In certain embodiments, the flagellin polypeptides from the genus *Enterococcus* are used the only therapeutic agent in a composition for use in treating bacterial infections.

Vaccine Adjuvants

Microbial components can be used as adjuvants to enhance the immune responses of poorly immunogenic vaccines. Flagellin has been shown to act as adjuvants in vaccines for bacterial, viral and parasitic infections, however, most of these studies used flagellin from *S. typhimurium* and *Vibrio vulnificus* [15]. The efficacy of flagellin polypeptides from other species to act as vaccine adjuvants, and in particular *Enterococcus* spp., is unknown.

Flagellin acts as an adjuvant by stimulating the innate immune response through the TLR5 receptor. The inventors have surprisingly shown that flagellin polypeptides from the genus *Enterococcus* are able to stimulate a stronger TLR5 response than *S. typhimurium*. Thus, the inventors have shown that flagellin polypeptides from the genus *Enterococcus*, and in particular the species *Enterococcus gallinarum* can be useful as vaccine adjuvants. Use of a flagellin polypeptide as a vaccine adjuvant means that the flagellin polypeptide is used, for example, to provide protection against an infective agent or prevent infection by an infective agent, generally by enhancing the immune response to a separate antigen.

The invention provides flagellin polypeptides from the genus *Enterococcus* for use as vaccine adjuvants. The invention also provides flagellin polypeptides the species *Enterococcus gallinarum* for use as vaccine adjuvants. More preferably, the invention provides flagellin polypeptide from strain MRx0518, in particular with the sequence SEQ ID NO:1, for use as vaccine adjuvants.

The invention also provides vaccine compositions comprising flagellin polypeptides of the invention as an adjuvant. In certain embodiments, the vaccine compositions are for use in treating or preventing bacterial infections. In certain embodiments, the bacterial pathogen to be treated or prevented is *Y. pestis*, tetanus, *Streptococcus pneumoniae*, *Escherichia coli* or *M. tuberculosis*. In certain embodiments, the vaccine compositions are for use in treating or preventing viral infections. In certain embodiments, the viral pathogen to be treated or prevented is influenza, HIV, rabies or foot and mouth virus. In certain embodiments, the vaccine compositions are for use in treating or preventing parasitic infections. In certain embodiments, the parasite is *Plasmodium vivax*, *Plasmodium yoelii* or *Eimeria tenella*. In any such embodiments, the composition comprises at least one antigen from the relevant pathogen. In preferred such embodiments, the composition comprises the flagellin of the invention fused or conjugated to at least one antigen from the relevant pathogen. In such embodiments, the invention provides a fusion polypeptide comprising a flagellin of the invention, an optional linker, and an antigen from a pathogen or parasite.

Administration through a mucosal route is an attractive vaccine administration route. Flagellin is a potent activator of innate immune signalling pathways in epithelial cells, which are the first major cell type that encounter agents administered by a mucosal route. *S. typhimurium* and *Vibrio vulnificus* flagellin proteins have been shown to potent adjuvant activity in mucosal vaccines against influenza, West Nile virus, *Escherichia coli*, *Yersinia pestis*, *Clostridium tetani*, *C. jejuni*, *Streptococcus* spp. and *Plasmodium falciparum* [15]. The efficacy of flagellin polypeptides from other species to act as mucosal vaccines adjuvants is unknown.

Flagellin acts as an adjuvant by stimulating the innate immune response through the TLR5 receptor. The inventors have surprisingly shown that flagellin polypeptides from the genus *Enterococcus* are able to stimulate a stronger TLR5 response than *S. typhimurium*. Thus, the invention provides flagellin polypeptides from the genus *Enterococcus* for use as a mucosal vaccine adjuvant. In preferred embodiments the invention provides flagellin polypeptides from the species *Enterococcus gallinarum* for use as mucosal vaccine adjuvants. More preferably, the invention provides flagellin polypeptide from strain MRx0518, in particular with the sequence SEQ ID NO:1, for use mucosal as vaccine adjuvants.

In certain embodiments, flagellin polypeptides from the genus *Enterococcus* are for use in mucosal vaccine for use in treating or preventing bacterial infections. In preferred embodiments, the bacterial infection is *Escherichia coli*, *Yersinia pestis*, *Clostridium tetani*, *C. jejuni*, *Streptococcus* spp. or *Plasmodium falciparum*. In certain embodiments, flagellin polypeptides from the genus *Enterococcus* are for use in mucosal vaccines for use in treating or preventing viral infections. In preferred embodiments, the viral infection is influenza or the West Nile virus.

Administration of the compositions of the invention may lead to an increase in expression of Tumour Necrosis Factor alpha (TNF-α). TNF-α is known to be important for vaccine responses. For example, TNF-α has been shown to be required for an efficient vaccine response in a flu vaccination of the elderly population [69]. Since administration of the compositions of the invention may increase TNF-α expression, compositions of the invention may be useful as a vaccine adjuvant. In one embodiment, the compositions of the invention are for use as a vaccine adjuvant by increasing the level and/or activity of TNF-α. In one embodiment, the compositions of the invention are for use as a vaccine adjuvant. In one embodiment, the compositions of the invention are for use as a vaccine adjuvant in influenza therapy. In certain embodiments, the compositions of the invention are for use in enhancing an immune response against an antigen. In certain embodiments, the invention provides a composition to be administered in combination with an antigen. In such embodiments of the invention, the flagellin of the invention may be fused or conjugated to the antigen. In certain embodiments, the compositions of the invention are for administration to a patient shortly prior to or after vaccination.

*Enterococcus gallinarum* and in particular strain MRX518 is flagellated and flagellins can be TLR5 agonists. TLR agonists are in development as vaccine adjuvants across a range of antigen types, particularly in the elderly population [70]. Also, MRX518 is a TLR5 agonist. Therefore, the compositions of the invention may be useful as vaccine adjuvants, in particular for vaccine administered to elderly patients (e.g. over 40, 50, 60, 70 or 80 years of age), who may have reduced immune system activity. TLR5 signalling also plays a key role in age-associated innate immune responses [71]. In certain embodiments, the compositions are for use in enhancing an innate immune response. Although TLR5 agonists are in development as vaccine adjuvants, these are all from known pathogens and/or synthetic. In contrast, the compositions of the invention comprise commensal bacteria.

Administration of the compositions of the invention may lead to an increase in expression of IL-6. Increased 11-6 expression has been associated with vaccine responses for many diseases. For example, IL-6 was produced by CD14+ CD16-inflammatory monocytes after adults were administered an influenza vaccine [72], and higher levels of IL-6 were associated with achieving a vaccine response to an influenza vaccine [73]. Furthermore, 11-6 was produced after injection of the AS03 adjuvant system [74] and down-regulation of IL-6 in mice was shown to reduce the helper T cell response after administration of a tuberculosis vaccine [75]. Since administration of the compositions of the invention may increase IL-6 expression, compositions of the invention may be useful as a vaccine adjuvant. In one embodiment, the compositions of the invention are for use as a vaccine adjuvant by increasing the level and/or activity of IL-6. In one embodiment, the compositions of the invention are for use as a vaccine adjuvant. In one embodiment, the compositions of the invention are for use as a vaccine adjuvant in tuberculosis therapy.

Furthermore, IL-6 and TNF-α expression have been shown to be correlated with the efficacy of a therapeutic HIV vaccine [Huang et al] a tuberculosis vaccine and a *chlamydia* vaccine [76]. Su et al. [77] showed that co-inoculation of IL-6 or TNF-α with the FMDV DNA vaccine resulted in increased IFN-γ expression by CD4+ and CD8+ T cells, higher expression of IL-4 in CD4+ T cells and a higher antigen-specific cytotoxic response. Since administration of the compositions of the invention may increase IL-6 and TNF-α expression, compositions of the invention may be useful as a vaccine adjuvant. In one embodiment, the compositions of the invention may be useful as a vaccine adjuvant by increasing the level and/or activity of TNF-α. In one embodiment, the compositions of the invention may be useful as a vaccine adjuvant by increasing the level and/or activity of IL-6. In a particular embodiment, the compositions of the invention may be useful as a vaccine adjuvant by increasing the level and/or activity of TNF-α and IL-6. In one embodiment, the compositions of the invention are for use as a vaccine adjuvant in HIV therapy. In one embodiment, the compositions of the invention are for use as a vaccine adjuvant in *chlamydia* therapy.

Administration of the compositions of the invention may lead to an increase in expression of IL-1β. Li et al. [78] showed that the adjuvant aluminium hydroxide activated the secretion of IL-1β, and suggested that IL-β itself can act as an adjuvant. Since administration of the compositions of the invention may increase IL-1β expression, compositions of the invention may be useful as a vaccine adjuvant. The examples show that administration of the compositions of the invention can increase the ratio of CD8+ T cells to Tregs. Adjuvants have been shown to stimulate CD8+ T cells [79] and since administration of the compositions of the invention were shown to increase the ratio of CD8+ T cells to Tregs, compositions of the invention may be useful as a vaccine adjuvant. In one embodiment, compositions of the invention are for use as a vaccine adjuvant. In one embodiment, the compositions of the invention are for use as a vaccine adjuvant by increasing the ratio of CD8+ T cells to Tregs.

Administration of the compositions of the invention may lead to an increase in expression or levels of CXCR3 ligands CXCL9 and CXCL10. Known adjuvants such as ASO3, CpG, GLA-SE, αGalCer all increase CXCL9 and 10 [80, 81], which suggests the compositions of the invention will be effective as adjuvants. Also, CXCL9 and 10 are associated with IFNγ/Th1 responses and promote antibody responses [82]. In certain embodiments, the compositions of the invention are for use in promoting an antibody response against an antigen, in particular a pathogenic or cancer antigen. Also, CXCL9 is a more sensitive measure than IFN-γ of vaccine induced T-cell responses in volunteers receiving investigated malaria vaccines [83]. In certain embodiments, the compositions of the invention are for use in promoting an T-cell response against an antigen, in particular a pathogenic or cancer antigen. In one embodiment, the compositions of the invention are for use as a vaccine adjuvant by increasing the level and/or activity of CXCL9 and CXCL10. In certain embodiments, the compositions are for use in protecting against malaria.

Administration of the compositions of the invention can lead to an increase in expression or levels of IL-12p70. This effect has been associated with vaccine adjuvant efficiency and IL-12 has been proposed as an adjuvant itself [84], which suggests the compositions of the invention will be effective as adjuvants. In one embodiment, the compositions of the invention are for use as a vaccine adjuvant by increasing the level and/or activity of IL-12p70.

Generally, when used as a vaccine adjuvant, the compositions of the invention will be administered on their own to provide an adjuvant effect for an antigen that has been separately administered to the patient. In certain embodiments, the composition of the invention is administered orally, whilst the antigen is injected parenterally. In alternative embodiments, the flagellin of the invention may be fused or conjugated to the antigen.

The compositions of the invention may be used for enhancing an immune response to any useful antigen. Exemplary antigens for use with the invention include: viral antigens, such as viral surface proteins; bacterial antigens, such as protein and/or saccharide antigens; fungal antigens; parasite antigens; and tumor antigens. The invention is particularly useful for vaccines against influenza virus, HIV, hookworm, hepatitis B virus, herpes simplex virus, rabies, respiratory syncytial virus, cytomegalovirus, *Staphylococcus aureus, chlamydia*, SARS coronavirus, varicella zoster virus, *Streptococcus pneumoniae, Neisseria meningitidis, Mycobacterium tuberculosis, Bacillus anthracis*, Epstein Barr virus, human papillomavirus, etc. In certain embodiments, the flagellin of the invention is fused or conjugated to one or more of these antigens.

Further antigens for use with the flagellins of the invention include glycoprotein and lipoglycan antigens. In certain embodiments, the antigen is an archaea antigen. Exemplary tumour-associated antigens include melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens and oncoproteins.

Flagellins of the invention may also be useful for enhancing the response to vaccines against non-communicable diseases such as Alzheimer's Disease and other neurodegenerative disorders, in which case the antigen for use with the invention may be amyloid-beta or Tau. Other such antigens for non-communicable diseases include PCSK9 (for the treatment of elevated cholesterol). Flagellins of the invention may also be useful for enhancing the response to vaccines against habit forming substances, for example nicotine, alcohol or opiates.

The invention also provides the use of: (i) an aqueous preparation of an antigen; and (ii) a composition comprising a flagellin polypeptide from the species *Enterococcus gallinarum*, in the manufacture of a medicament for raising an immune response in a patient.

The immune response raised by these methods and uses will generally include an antibody response, preferably a protective antibody response.

Stimulating the Immune System

The compositions of the invention can lead to immune stimulation. Since administration of the compositions of the invention may have an immunostimulatory effect, compositions of the invention may be useful in the treatment of disease, in particular diseases characterised by reduced immune activation and diseases treatable by an increased immune response. In certain embodiments, the compositions of the invention are for use in stimulating the immune system. In certain embodiments, the compositions of the invention are for use in treating disease by stimulating the immune system. In certain embodiments, the compositions of the invention are for use in promoting an immune response.

Compositions of the invention may be useful in the treatment of diseases characterised by an increase in the percentage of Tregs in a cell population. In one embodiment, the compositions of the invention may be useful for treating or preventing diseases characterised by an increase in the percentage of Tregs in a cell population. In one embodiment, the compositions of the invention may be useful for treating or preventing diseases characterised by an increase in the percentage of CD4+CD25+CD127− cells in a cell population. In one embodiment, the compositions of the invention are for use in treating or preventing diseases by decreasing the percentage of Tregs in cell populations. In one embodiment, compositions of the invention are for use in reducing suppression of the immune response by Tregs. In one embodiment, compositions of the invention are for use in stimulating the immune response by the selective reduction of Tregs. In one embodiment, compositions of the invention are for use in immunostimulation, wherein the compositions of the invention reduce the number or percentage of Tregs.

Compositions of the invention may be useful in the treatment of diseases characterised by a decrease in the ratio of CD8/Treg and/or activated CD8/Treg cells. In one embodiment, the compositions of the invention are for use in treating or preventing diseases characterised by decrease in the ratio of CD8/Treg cells. In one embodiment, the compositions of the invention are for use in treating or preventing diseases characterised by decrease in the ratio of activated CD8/Treg cells. In one embodiment, compositions of the invention are for use in stimulating the immune response by increasing the ratio of CD8/Treg cells. In one embodiment, compositions of the invention are for use in stimulating the immune response by increasing the ratio of activated CD8/Treg cells.

Compositions of the invention may be useful in the treatment of diseases characterised by a decrease in the number or percentage of B cells. In one embodiment, the compositions of the invention are for use in treating or preventing diseases characterised by decrease in the number or percentage of B cells. In one embodiment, the compositions of the invention are for use in treating or preventing diseases characterised by decrease in the number or percentage of CD19+CD3− cells. In one embodiment, the compositions of the invention are for use in treating or preventing diseases by increasing the number or percentage of B cells in cell populations, wherein the increase in number or percentage of B cells results in immune stimulation. In one embodiment, compositions of the invention are for use in stimulating the immune response by increasing the number or percentage of B cells.

Compositions of the invention may be useful in the treatment of diseases characterised by a decrease in the number or percentage of CD8 T-cytotoxic cells. In one embodiment, the compositions of the invention are for use in treating or preventing diseases characterised by decrease in the number or percentage of CD8 T-cytotoxic cells. In one embodiment, the compositions of the invention are for use in treating or preventing diseases by increasing the number or percentage of CD8 T-cytotoxic cells in cell populations, wherein the increase in number or percentage of CD8 T-cytotoxic cells results in immune stimulation. In one embodiment, compositions of the invention are for use in stimulating the immune response by increasing the number or percentage of CD8 T-cytotoxic cells.

Compositions of the invention may be useful in the treatment of diseases characterised by a decrease in the number or percentage of CD8+ activated cells. In one embodiment, the compositions of the invention are for use in treating or preventing diseases characterised by decrease in the number or percentage of CD8+ activated cells. In one embodiment, the compositions of the invention are for use in treating or preventing diseases by increasing the number or percentage of CD8+ activated cells in cell populations, wherein the increase in number or percentage of CD8+ activated cells results in immune stimulation. In one embodiment, compositions of the invention are for use in stimulating the immune response by increasing the number or percentage of CD8+ activated cells.

Administration of the compositions of the invention may lead to an increase in expression of pro-inflammatory molecules, such as pro-inflammatory cytokines. Examples of pro-inflammatory molecules that may show an increase in expression levels upon administration of compositions of the invention include IL-8, IL-12p70, IL-23, TNF-α, IL-1β, and IL-6. Since administration of the compositions of the invention may increase the expression of pro-inflammatory molecules, compositions of the invention may be useful in the treatment of diseases characterised by a decrease in expression of pro-inflammatory molecules, such as pro-inflammatory cytokines. In one embodiment, the compositions of the invention are for use in treating or preventing diseases characterised by a decrease in the expression and/or activity of pro-inflammatory molecules, in particular diseases characterised by a decrease in the expression and/or activity of pro-inflammatory cytokines. In a particular embodiment, the compositions of the invention are for use in treating or preventing diseases characterised by a decrease in the expression and/or activity of IL-8, IL-12p70, IL-23, TNF-α, IL-1β, and/or IL-6. In one embodiment, the compositions of the invention are for use in treating or preventing diseases by increasing the expression and/or activity of IL-23, TNF-α, IL-1β, and/or IL-6. In one embodiment, compositions of the invention are for use in promoting the immune response by increasing the expression and/or activity of IL-8, IL-12p70, IL-23, TNF-α, IL-1β, and/or IL-6.

Administration of the compositions of the invention may lead to an increase in expression of IL-1β. IL-1β is a pro-inflammatory cytokine [85]. The production and secretion of IL-1β is regulated by the inflammasome, a protein complex which is associated with activation of the inflammatory response [86]. Since administration of the compositions of the invention may increase the expression of IL-1β, compositions of the invention may be useful in the treatment of diseases characterised by a decrease in expression of IL-1β. In a particular embodiment, the compositions of the invention are for use in treating or preventing diseases characterised by a decrease in the expression and/or activity of IL-1β. In one embodiment, the compositions of the invention are for use in treating or preventing diseases by increasing the expression and/or activity of IL-1β.

Administration of the compositions of the invention may lead to an increase in expression of IL-23. IL-23 has been linked to inflammation [87,88]. The proposed functions of IL-23 in the immune response include promoting the proliferation of CD4+ memory T cells and promoting the secretion of IFN-γ by dendritic cells (DCs) [89]. Since administration of the compositions of the invention may increase the expression of IL-23, compositions of the invention may be useful in the treatment of diseases characterised by a decrease in expression of IL-23. In a particular embodiment, the compositions of the invention are for use in treating or preventing diseases characterised by a decrease in the expression and/or activity of IL-23. In one embodiment, the compositions of the invention are for use in treating or preventing diseases by increasing the expression and/or activity of IL-23. In one embodiment, compositions of the invention are for use in promoting the immune response by increasing the expression and/or activity of IL-23.

Administration of the compositions of the invention may lead to an increase in expression of Tumour Necrosis Factor alpha (TNF-α). TNF-α is a pro-inflammatory cytokine which is known to be involved in various signalling pathways to promote cell death. TNF-α initiates apoptosis by binding to its cognate receptor, TNFR-1, which leads to a cascade of cleavage events in the apoptotic pathway [90]. TNF-α can also trigger necrosis via a RIP kinase-dependent mechanism [91]. Since administration of the compositions of the invention may increase TNF-α expression, compositions of the invention may be useful in the treatment of diseases, in particular for use in treating or preventing diseases characterised by a decrease in expression of by TNF-α. In one embodiment, the compositions of the invention are for use in treating diseases characterised by decreased TNF-α expression. In a particular embodiment, the compositions of the invention are for use in treating or preventing diseases characterised by a decrease in the expression and/or activity of TNF-α. In one embodiment, the compositions of the invention may be useful for treating or preventing diseases by increasing the expression and/or activity of TNF-α. In one embodiment, compositions of the invention are for use in promoting the immune response by increasing the expression and/or activity of TNF-α.

Administration of the compositions of the invention may lead to an increase in expression of IL-6. IL-6 a proinflammatory cytokine that is produced during inflammation, and promotes the differentiation of naïve CD4+ T cells and the differentiation of CD8+ T cells into cytotoxic T cells [92]. Since administration of the compositions of the invention may increase the expression of IL-6, compositions of the invention may be useful in the treatment of diseases characterised by a decrease in expression of IL-6. In a particular embodiment, the compositions of the invention are for use in treating or preventing diseases characterised by a decrease in the expression and/or activity of IL-6. In one embodiment, the compositions of the invention are for use in treating or preventing diseases by increasing the expression and/or activity of IL-6. In one embodiment, compositions of the invention are for use in promoting the immune response by increasing the expression and/or activity of IL-6.

Bettelli et al. [93] reported that IL-6 inhibits the production of Tregs. Compositions of the invention may increase the expression of IL-6, so compositions of the invention may selectively decrease the number or percentage of Tregs by increasing the expression of IL-6. In one embodiment, compositions of the invention are for use in immunostimulation by increasing the expression of IL-6. In another embodiment, compositions of the invention are for use in immunostimulation by decreasing the number or percentage of Tregs.

The examples also demonstrate that the compositions of the invention promote the differentiation of T-helper cells and cytotoxic T lymphocytes. Therefore, in certain embodiments, the compositions of the invention are for use in stimulating the differentiation of T-helper cells and/or cytotoxic T lymphocytes.

Cell Therapies
Chimeric Antigen Receptor T Cell (CAR-T) Therapy

Administration of the compositions of the invention may lead to an increase in expression of IL-6. Increased 11-6 expression has been correlated with response to CD19 CAR-T therapy of chronic lymphocyte leukaemia. An increase in serum IL-6 was associated with CAR-T cell expansion, whereas inhibition of IL-6 was associated with inhibition of CAR-T cell proliferation [94]. Since administration of the compositions of the invention may increase IL-6 expression, compositions of the invention may be useful in cell therapy, in particular CAR-T cell therapy. In one embodiment, the compositions of the invention are for use in cell therapy. In one embodiment, compositions of the invention are for use in CAR-T cell therapy. In one embodiment, compositions of the invention are for use in the treatment of chronic lymphocyte leukaemia.

Selective depletion of Tregs has been shown to enhance the efficacy of cytotoxic lymphocytes [95]. CAR-T cells are a subset of cytotoxic lymphocytes, and therefore it is thought that selective depletion of Tregs is effective in CAR-T cell therapy. Since administration of the compositions of the invention may deplete Tregs, compositions of the invention may be useful in cell therapy, in particular CAR-T cell therapy.

Therefore, the compositions of the invention may be useful in cell therapy, in particular in enhancing the response to a cell therapy.

Mesynchymal Stem Cell (MSC) Therapy

Mesynchymal stem cell (MSC) therapy has been reported to have immunostimulatory properties. When MSCs are treated with LPS, they upregulate pro-inflammatory cytokines IL-6 and IL-8 which causes increased B cell proliferation [96]. Therefore, since compositions of the invention may increase the expression of IL-6, they may be useful in combination with MSC cell therapy.

Stem Cell Transplantation Therapy

It has been reported that, instead of using undifferentiated stem cells in stem cell transplantation therapy, it may be beneficial to differentiate stem cells to some extent prior to transplantation. For example, Heng et al. [97] reported that cardiomyogenic differentiation of stem cells may be beneficial by having a higher engraftment efficiency, enhanced regeneration of myocytes and increased restoration of heart function. Since administration of the compositions of the invention may initiate neuronal differentiation in undifferentiated neuroblastoma cells, compositions of the invention may be useful for stem cell differentiation in stem cell transplantation therapy.

Hematopoietic Stem Cell Transplantation

Hematopoietic stem cell transplantation is the transplantation of multipotent hematopoietic stem cells, usually derived from bone marrow, peripheral blood, or umbilical cord blood. Colonisation of the gut with Enterococci (*Enterococcus gallinarum* and *Enterococcus casseliflavus*) prior to allogenic hematopoietic stem cell transplantation has been shown to lead to a significantly improved the 2-year survival of patients after due to decreased nonrelapse mortality [98]. Therefore, the immunomodulatory effect shown in the examples may be useful in hematopoietic stem cell transplantation therapy. In certain embodiments, the compositions of the invention may be useful in improving survival after hematopoietic stem cell transplantation and in particular after allogenic hematopoietic stem cell transplantation.

The compositions of the invention may be useful in combination with allogenic hematopoietic stem cell transplantation. The compositions of the invention may be effecting in boosting successful patient response to allogenic hematopoietic stem cell transplantation. In certain embodiments, the compositions of the invention are administered prior to hematopoietic stem cell transplantation. In certain embodiments, the compositions of the invention are for administration to a patient scheduled to receive hematopoietic stem cell transplantation. In certain embodiments, the compositions of the invention are administered following hematopoietic stem cell transplantation. In certain embodiments, the compositions of the invention are for administration to a patient that has received hematopoietic stem cell transplantation.

Immunosenescence

Fulop et al. [99] identified that an increase in Treg cell number and a decrease in B cell number are associated with aging in the adaptive immune system. Therefore, compositions of the invention may be used to prevent or delay immunosenescence. In one embodiment, compositions of the invention are for use in preventing immunosenescence.

In another embodiment, compositions of the invention are for use in delaying immunosenescence characterised by an increase in Treg cell number. In another embodiment, compositions of the invention are for use in delaying immunosenescence characterised by a decrease in B cell number. In another embodiment, compositions of the invention are for use in delaying immunosenescence characterised by an increase in Treg cell number and a decrease in B cell number. In one embodiment, compositions of the invention are for use in delaying immunosenescence by decreasing Treg cell number. In one embodiment, compositions of the invention are for use in delaying immunosenescence by increasing B cell number. In another embodiment, compositions of the invention are for use in delaying immunosenescence by decreasing Treg cell number and increasing B cell number. In one embodiment, compositions of the invention are for use in treating diseases caused by immunosenescence. In one embodiment, compositions of the invention are for use in treating aging-related diseases by delaying and/or preventing immunosenescence.

Furthermore, it has been proposed that vaccine adjuvants may overcome immunosenescence [100]. Since the compositions of the invention are suitable for use as a vaccine adjuvant, compositions of the invention may be useful for preventing or delaying immunosenescence. In another embodiment, compositions of the invention are for use in delaying and/or preventing immunosenescence as a vaccine adjuvant. In another embodiment, compositions of the invention are for use as a vaccine adjuvant, wherein the compositions delay and/or prevent immunosenescence.

Diseases that are associated with immunosenescence include cardiovascular disease, neurodegenerative diseases, such as Alzheimer's disease and Parkinson's disease, cancer, diabetes mellitus type 2 [101] and autoimmune disorders [102].

Modes of Administration

Preferably, the compositions of the invention are administered by injection, preferably subcutaneously or alternatively intravenously, or intraperitoneally. Further details regarding compositions suitable for administered by injection are provided in the next section. In alternative embodiments, the compositions of the invention are to be administered to the gastrointestinal tract. The immune system is known to be modulated by the presence of bacteria and bacterial proteins in the gastrointestinal tract. The compositions of the invention are administered orally, but they may be administered rectally, intranasally, or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a *theobroma* oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily.

In certain embodiments of the invention, treatment according to the invention is accompanied by assessment of the patient's gut microbiota.

The compositions of the invention may be administered to a patient that has been diagnosed with cancer, or that has been identified as being at risk of a cancer. The compositions may also be administered as a prophylactic measure to prevent the development of cancer in a healthy patient.

The compositions of the invention may be administered to a patient that has been identified as having an abnormal gut microbiota. For example, the patient may have reduced or absent colonisation by *Enterococcus* spp, in particular *Enterococcus gallinarum*.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

Compositions

Generally, the composition of the invention comprises a flagellin polypeptide from the genus *Enterococcus* and in particular from the species *Enterococcus gallinarum*.

In preferred embodiments, the composition of the invention is encapsulated to enable delivery of flagellin to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule.

Compositions may thus be pharmaceutically acceptable. They will usually include components in addition to the flagellin polypeptide (or nucleic acid) e.g. they typically include one or more pharmaceutical carrier(s) and/or excipient(s).

Compositions may be administered to a human in aqueous form. In such embodiments, prior to administration, however, the composition may have been in a non-aqueous form. For instance, although some therapeutics are manufactured in aqueous form, then filled and distributed and administered also in aqueous form, other therapeutics are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the therapeutics should be substantially free from (i.e. less than 5 µg/ml) mercurial material e.g. thiomersal-free. Therapeutics containing no mercury are more typical. Preservative-free therapeutics are particularly favoured.

To improve thermal stability, a composition may include a temperature protective agent. Further details of such agents are provided below.

To control tonicity, it is typical to include a physiological salt, such as a sodium salt. Sodium chloride (NaCl) is generally used, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, more often between 240-360 mOsm/kg, and will more typically fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is typically sterile. The composition is also typically non-pyrogenic e.g. containing <1 EU (endotoxin unit, a standard measure) per dose, for example <0.1 EU per dose. The composition is often gluten free.

The composition may include material for a single administration, or may include material for multiple administration (i.e. a 'multidose' kit). The inclusion of a preservative is typical in multidose arrangements. As an alternative (or in addition) to including a preservative in multidose compositions, the compositions may be contained in a container having an aseptic adaptor for removal of material.

Human protein therapeutics are typically administered in a dosage volume of about 0.5 ml, although a half dose (i.e. about 0.25 ml) may be administered to children.

Compositions of the invention may also comprise one or more immunoregulatory agents. Often, one or more of the immunoregulatory agents include one or more adjuvants. The adjuvants may include a TH1 adjuvant and/or a TH2 adjuvant, further discussed below.

The compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a mammal. Such kits may comprise one or more antigens in liquid form and one or more lyophilised antigens. In certain embodiments, the flagellin of the invention present in the composition may be fused or conjugated to one or more antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Compositions used as therapeutics comprise an immunologically effective amount of polypeptide or encoding nucleic acid, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition then two antigens may be present at the same dose as each other or at different doses.

As mentioned above, a composition may include a temperature protective agent, and this component may be particularly useful in adjuvanted compositions (particularly those containing a mineral adjuvant, such as an aluminium salt). As described in reference 103, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGS may have an average molecular weight ranging from 200-20,000 Da. In one embodiment, the polyethylene glycol can have an average molecular weight of about 300 Da (PEG-300').

The invention provides a composition comprising: (i) one or more flagellin polypeptides(s); and (ii) a temperature protective agent. This composition may be formed by mixing (i) an aqueous composition comprising one or more antigen(s), with (ii) a temperature protective agent. The mixture may then be stored e.g. below 0° C., from 0-20° C., from 20-35° C., from 35-55° C., or higher. It may be stored in liquid or frozen form. The mixture may be lyophilised. The composition may alternatively be formed by mixing (i) a dried composition comprising one or more antigen(s), with (ii) a liquid composition comprising the temperature protective agent. Thus component (ii) can be used to reconstitute component (i).

The composition may be administered orally and may be in the form of a tablet, capsule or powder. Other ingredients (such as vitamin C, for example), may be included as oxygen scavengers and prebiotic substrates to improve the delivery and/or partial or total colonisation and survival in vivo.

A composition of the invention includes a therapeutically effective amount of a flagellin polypeptide of the invention. A therapeutically effective amount of a flagellin polypeptide is sufficient to exert a beneficial effect upon a patient.

The compositions of the invention may comprise pharmaceutically acceptable excipients or carriers. Examples of such suitable excipients may be found in the reference [104]. Acceptable carriers or diluents for therapeutic use are well known in the pharmaceutical art and are described, for example, in reference [105]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

In some embodiments, the composition comprises more than one flagellin polypeptide from the genus *Enterococcus* for use in treating or preventing cancer. In certain embodiments, the composition comprises a flagellin polypeptide with SEQ ID NO:1 and at least one further flagellin polypeptide from the genus *Enterococcus*. In certain embodiments, the composition comprises a flagellin polypeptide with SEQ ID NO:1 and at least one flagellin polypeptide from the species *Enterococcus gallinarum*. In certain embodiments, the composition comprises a flagellin polypeptide with SEQ ID NO:1 and at least one flagellin polypeptide selected from a group consisting of SEQ ID NO 2-42. In some embodiments, the composition can comprise at least 3, 4, 5, 6, 7, 8, 9, 10, 11, 12, 13, 14, 15, 20, 25, 30, 35, 40 or 45 flagellin polypeptides from the genus *Enterococcus* and in particular from the species *Enterococcus gallinarum*. In some embodiments, the compositions of the invention comprise less than 50 flagellin polypeptides from within the same species (e.g. less than 45, 40, 35, 30, 25, 20, 15, 12, 10, 9, 8, 7, 6, 5, 4 or 3 strains), and, optionally, do not contain flagellin polypeptides from any other species. In some embodiments, the compositions of the invention comprise 1-40, 1-30, 1-20, 1-19, 1-18, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 flagellin polypeptides from within the same species and, optionally, do not contain flagellin polypeptides from any other species.

In some embodiments in which the composition of the invention comprises more than one flagellin polypeptide, the individual flagellin polypeptides may be for separate, simultaneous or sequential administration. For example, the composition may comprise all of the flagellin polypeptides, or the flagellin polypeptides may be stored separately and be administered separately, simultaneously or sequentially. In some embodiments, the more than one flagellin polypeptides are stored separately but are mixed together prior to use.

The compositions for use in accordance with the invention may or may not require marketing approval.

The compositions of the invention can comprise pharmaceutically acceptable excipients, diluents or carriers.

In certain embodiments, the invention provides a pharmaceutical composition comprising: a flagellin polypeptide as used in the invention; and a pharmaceutically acceptable excipient, carrier or diluent; wherein the flagellin polypeptide is in an amount sufficient to treat a disorder when administered to a subject in need thereof.

In certain embodiments, the invention provides a pharmaceutical composition comprising: a flagellin polypeptide as used in the invention; and a pharmaceutically acceptable excipient, carrier or diluent; wherein the flagellin polypeptide is in an amount sufficient to treat a disorder when administered to a subject in need thereof; and wherein the disorder is breast cancer. In preferred embodiments the cancer is mammary carcinoma. In preferred embodiments the cancer is stage IV breast cancer.

In certain embodiments, the invention provides a pharmaceutical composition comprising: a flagellin polypeptide as used in the invention; and a pharmaceutically acceptable excipient, carrier or diluent; wherein the flagellin polypeptide is in an amount sufficient to treat a disorder when administered to a subject in need thereof; and wherein the disorder is lung cancer. In preferred embodiments the cancer is lung carcinoma.

In certain embodiments, the invention provides a pharmaceutical composition comprising: a flagellin polypeptide as used in the invention; and a pharmaceutically acceptable excipient, carrier or diluent; wherein the flagellin polypeptide is in an amount sufficient to treat a disorder when administered to a subject in need thereof; and wherein the disorder is liver cancer. In preferred embodiments the cancer is hepatoma (hepatocellular carcinoma).

In certain embodiments, the invention provides a pharmaceutical composition comprising: a flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is colon cancer. In preferred embodiments the cancer is colorectal adenocarcinoma.

In certain embodiments, the invention provides a pharmaceutical composition comprising: a flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is carcinoma.

In certain embodiments, the invention provides a pharmaceutical composition comprising: a flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is a non-immunogenic cancer.

In certain embodiments, the invention provides a pharmaceutical composition comprising: a flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is a immunogenic cancer.

In certain embodiments, the invention provides a pharmaceutical composition comprising: a flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is selected from the group consisting of non-small-cell lung carcinoma, small-cell lung carcinoma, squamous-cell carcinoma, adenocarcinoma, glandular tumors, carcinoid tumors undifferentiated carcinomas.

In certain embodiments, the invention provides a pharmaceutical composition comprising: a flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is selected from the group consisting of hepatoblastoma, cholangiocarcinoma, cholangiocellular cystadenocarcinoma or liver cancer resulting from a viral infection.

In certain embodiments, the invention provides a pharmaceutical composition comprising: a flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is selected from the group consisting of invasive ductal carcinoma, ductal carcinoma in situ or invasive lobular carcinoma.

In certain embodiments, the invention provides a pharmaceutical composition comprising: flagellin polypeptide of the invention; and a pharmaceutically acceptable excipient, carrier or diluent; wherein the flagellin polypeptide is in an amount sufficient to treat a disorder when administered to a subject in need thereof; and wherein the disorder is selected from the group consisting of acute lymphoblastic leukemia (ALL), acute myeloid leukemia, adrenocortical carcinoma, basal-cell carcinoma, bile duct cancer, bladder cancer, bone tumor, osteosarcoma/malignant fibrous histiocytoma, brainstem glioma, brain tumor, cerebellar astrocytoma, cerebral astrocytoma/malignant glioma, ependymoma, medulloblastoma, supratentorial primitive neuroectodermal tumors, breast cancer, bronchial adenomas/carcinoids, Burkitt's lymphoma, carcinoid tumor, cervical cancer, chronic lymphocytic leukemia, chronic myelogenous leukemia, chronic myeloproliferative disorders, colon cancer, cutaneous T-cell lymphoma, endometrial cancer, ependymoma, esophageal cancer, Ewing's sarcoma, intraocular melanoma, retinoblastoma, gallbladder cancer, gastric cancer, gastrointestinal carcinoid tumor, gastrointestinal stromal tumor (GIST), germ cell tumor, glioma, childhood visual pathway and hypothalamic, Hodgkin lymphoma, melanoma, islet cell carcinoma, Kaposi sarcoma, renal cell cancer, laryngeal cancer, leukaemias, lymphomas, mesothelioma, neuroblastoma, non-Hodgkin lymphoma, oropharyngeal cancer, osteosarcoma, ovarian cancer, pancreatic cancer, parathyroid cancer, pharyngeal cancer, pituitary adenoma, plasma cell neoplasia, prostate cancer, renal cell carcinoma, retinoblastoma, sarcoma, testicular cancer, thyroid cancer, or uterine cancer.

A dose of a nucleic acid (e.g. a nucleic acid-based therapeutic) may have ≤100 µg nucleic acid; e.g. from 10-100 µg, such as about 10 µg, 25 µg, 50 µg, 75 µg or 100 µg, but expression can be seen at much lower levels; e.g. using ≤1 µg/dose, ≤100 ng/dose, ≤10 ng/dose, ≤1 ng/dose, etc. Similarly, a dose of a protein antigen may have ≤100 µg protein; e.g. from 10-100 µg, such as about 10 µg, 25 µg, 50 µg, 75 µg or 100 µg. The polypeptide may be administered in a dose of about 0.1-10 mg/kg body weight.

In certain embodiments, the pharmaceutical compositions of the invention may be administered in a single dose or in more preferably in repeated doses. Preferably repeat doses are administered about every 2, 5, 10, 7, 10 or 15 days. In certain embodiments, the invention provides the above pharmaceutical composition, wherein the composition is administered at a dose of 100 µg/kg, 200 µg/kg, 300 µg/kg, 400 µg/kg, 500 µg/kg, 1 mg/kg, 2 mg/kg, 5 mg/kg, 10 mg/kg, 20 mg/kg, 30 mg/kg, 50 mg/kg, 100 mg/kg, 200 mg/kg or 500 mg/kg of subjects body weight. Suitable unit doses include 1 mg, 2 mg, 5 mg, 10 mg, 20 mg, 30 mg, 50 mg, 100 mg, 200 mg, 500 mg, 1000 mg, 100-500 mg, 500-1000 mg, 200-400 mg, 5-00-750 mg, 750-1000 mg.

In certain embodiments, the invention provides the above pharmaceutical composition comprising host cells of the invention. A suitable daily dose of the host cells, for example for an adult human, may be from about $1\times10^3$ to about $1\times10^{11}$ colony forming units (CFU); for example, from about $1\times10^7$ to about $1\times10^{10}$ CFU; in another example from about $1\times10^6$ to about $1\times10^{10}$ CFU.

In certain embodiments, the composition contains the host cell in an amount of from about $1\times10^6$ to about $1\times10^{11}$ CFU/g, respect to the weight of the composition; for example, from about $1\times10^8$ to about $1\times10^{10}$ CFU/g. The dose may be, for example, 1 g, 3 g, 5 g, and 10 g. In some embodiments, the composition comprises a mixture of live host cells and host cells that have been killed.

In certain embodiments, the invention provides the above pharmaceutical composition, wherein the composition is administered by a method selected from the group consisting of oral, rectal, subcutaneous, nasal, buccal, sublingual, subcutaneous, intravenous, and intramuscular.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein when the composition is stored in a sealed container at about 4.0 or about 25.0 and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

In some embodiments, the composition of the invention is provided in a sealed container comprising a composition as described herein. In some embodiments, the sealed container is a sachet or bottle. In some embodiments, the composition of the invention is provided in a syringe comprising a composition as described herein.

The composition of the present invention may, in some embodiments, be provided as a pharmaceutical formulation. For example, the composition may be provided as a tablet or capsule. In some embodiments, the capsule is a gelatine capsule ("gel-cap").

In some embodiments, the compositions of the invention are administered orally. Oral administration may involve swallowing, so that the compound enters the gastrointestinal tract, and/or buccal, lingual, or sublingual administration by which the compound enters the blood stream directly from the mouth.

Pharmaceutical formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

In some embodiments the pharmaceutical formulation is an enteric formulation, i.e. a gastro-resistant formulation (for example, resistant to gastric pH) that is suitable for delivery of the composition of the invention to the intestine by oral administration. Enteric formulations may be particularly useful when the bacteria or another component of the composition is acid-sensitive, e.g. prone to degradation under gastric conditions.

In some embodiments, the enteric formulation comprises an enteric coating. In some embodiments, the formulation is an enteric-coated dosage form. For example, the formulation may be an enteric-coated tablet or an enteric-coated capsule, or the like. The enteric coating may be a conventional enteric coating, for example, a conventional coating for a tablet, capsule, or the like for oral delivery. The formulation may comprise a film coating, for example, a thin film layer of an enteric polymer, e.g. an acid-insoluble polymer.

In some embodiments, the enteric formulation is intrinsically enteric, for example, gastro-resistant without the need for an enteric coating. Thus, in some embodiments, the formulation is an enteric formulation that does not comprise an enteric coating. In some embodiments, the formulation is a capsule made from a thermogelling material. In some embodiments, the thermogelling material is a cellulosic material, such as methylcellulose, hydroxymethylcellulose or hydroxypropylmethylcellulose (HPMC). In some embodiments, the capsule comprises a shell that does not contain any film forming polymer. In some embodiments, the capsule comprises a shell and the shell comprises hydroxypropylmethylcellulose and does not comprise any film forming polymer (e.g. see [106]). In some embodiments, the formulation is an intrinsically enteric capsule (for example, Vcaps® from Capsugel).

In some embodiments, the formulation is a soft capsule. Soft capsules are capsules which may, owing to additions of softeners, such as, for example, glycerol, sorbitol, maltitol and polyethylene glycols, present in the capsule shell, have a certain elasticity and softness. Soft capsules can be produced, for example, on the basis of gelatine or starch. Gelatine-based soft capsules are commercially available from various suppliers. Depending on the method of administration, such as, for example, orally or rectally, soft capsules can have various shapes, they can be, for example, round, oval, oblong or torpedo-shaped. Soft capsules can be produced by conventional processes, such as, for example, by the Scherer process, the Accogel process or the droplet or blowing process.

General

The practice of the present invention will employ, unless otherwise indicated, conventional methods of chemistry, biochemistry, molecular biology, immunology and pharmacology, within the skill of the art. Such techniques are explained fully in the literature. See, e.g., references [107] and [108-114], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

The term "flagellin polypeptides from the genus *Enterococcus*" encompasses wild type flagellin polypeptides and mutated flagellin polypeptides that exhibit immunostimulatory properties, for example which can effectively activate TLR5 responses. The term "flagellin polypeptides" also encompasses fragments of wild type flagellin polypeptides and mutated flagellin polypeptides that exhibit immunostimulatory properties, for example which can effectively activate TLR5 responses.

References to a percentage sequence identity between two protein sequences means that, when aligned, that percentage of amino acid residues are the same in comparing the two sequences. This alignment and the percent homology or sequence identity can be determined using software programs known in the art, for example those described in ref. [115]. A preferred method uses MUSCLE alignment of protein sequences and can be performed with Geneious (78.02% pairwise identity), Blossom62 score matrix, threshold=1.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref. [116]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. [117].

Generally, unless specified otherwise (for example in relation to fragments), sequence identity is calculated over the length of the reference sequence (for example SEQ ID NO:1) and not over the length of the query sequence. Therefore, short and irrelevant sequences are not considered to have high sequence identity to the sequences of the invention.

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Example 1—Activation of TLR5 Reporter Cells by MRx0518

Summary

This study tested the efficacy of the bacterial strain MRx0518 to activate TLR5 reporter cells.

TLR5 Activation Assay

HEK-Blue TLR5 cells are HEK293 cells co-transfected with the human TLR5 gene and an inducible SEAP (secreted embryonic alkaline phosphatase) reporter gene. The SEAP gene is placed under the control of the IFN-β minimal promoter fused to five NF-κB and AP-1-binding sites. Stimulation with a TLR5 ligand activates NF-κB and AP-1 which induce the production of SEAP. The level of alkaline phosphatase thus relates to the TLR5 activity.

Materials

Reporter cell line: HEK-Blue hTLR5 (Invivogen, hkb-htlr5)

Cell growth media: DMEM (Sigma, D6171) supplemented with 10% (v/v) FBS (Sigma, F9665), 4 mM L-glutamine (Sigma, G7513), 100 U/ml penicillin and 100 ug/ml streptomiycin (Sigma, P4333), 100 ug/ml normocin (Invivogen, ant-nr-1) and selective antibiotics blasticidin (30 ug/ml, Invivogen, ant-bl-05) and zeocin (100 ug/ml, Invivogen, ant-zn-1)

Antibiotic-free media: DMEM supplemented with 10% (v/v) FBS and 4 mM L-glutamine Bacterial Growth Conditions Bacterial growth conditions: All *Enterococcus gallinarum* MRx0518 cultures were grown in yeast extract-casein hydrolysate-fatty acids (YCFA) broth (E&O Laboratories, UK) at 37° C., under anaerobic conditions.

Stationary phase MRx0518 cells: 16-18 hour cultures of strain MRx0518 were grown under the conditions described above using a 1% inoculum of MRx0518 cells, stored frozen as working cell banks at −80° C.

Late-log phase MRx0518 cells: 3 hour (approx.) cultures of strain MRx0518 were grown under the conditions described above using a 10% inoculum of stationary phase MRx0518 cells.

Procedure

The TLR5 activation assay was performed with the following treatments at two dosages—10:1 ($3 \times 10^5$ bacteria) or 100:1 ($3 \times 10^6$ bacteria):

Live MRx0518 bacteria

Heat killed MRx0518 bacteria

CFS from MRx0518

A positive control was performed with ultrapure FLA-ST at a concentration of 20 ng/ml and 5 ng/ml A negative control were performed with antibiotic-free media containing no reporter cells to control for the production of alkaline phosphatase by anything other than the reporter cells. Two additional controls were performed with YCFA and water. For all treatments three replicates were performed.

Preparation of Live and Cell-Free Supernatant (CFS) MRx0518

Live and CFS treatments were both prepared from one 10 ml culture of late-log phase MRx0518 cells following centrifugation of the cells at 5000×g for 5 mins at room temperature. The bacterial pellet was washed once in PBS (Sigma, D8537) and resuspended in antibiotic-free media to an estimated density of $1.4 \times 10^8$ CFU/ml (2-fold dilution) and $1.4 \times 10^7$ CFU/ml (20-fold dilution). The bacterial supernatant was collected, filtered (0.22 um) under sterile conditions and was diluted 10-fold and 20-fold using $H_2O$ (Sigma, W3500) to provide equivalents for the bacteria suspensions outlined above. The CFS contains MRx0518 flagella shed into the supernatant.

Preparation of Heat Killed (HK) Cells

Separately, HK cells were generated by incubating a 10 ml culture of late-log phase MRx0518 cells at 80° C. for 40 mins. Following centrifugation (conditions described above) the culture supernatant was discarded and the cell pellet was washed once in PBS (Sigma, D8537) and resuspended in antibiotic-free media to an estimated density of $1.4 \times 10^8$ CFU/ml (2-fold dilution) and $1.4 \times 10^7$ CFU/ml (20-fold dilution). Once prepared, all treatments were stored on ice prior to use. Viable cell counts per ml were determined for all live and heat-killed MRx0518 cell preparations.

Preparation of the Positive Control

A known agonist of TLR5, the *S. typhimurium* flagellin (ultrapure, FLA-ST ultrapure from Invitrogen, tlrl-epsitfla) was prepared at 200 ng/ml or 50 ng/ml in $H_2O$.

TLR5 Assay Conditions

20 μl of the appropriate treatment (bacterial cells, cell-free supernatant, positive control ligands, recombinant flagellin, negative controls e.g. YCFA, antibiotic-free media, $H_2O$, PBS) were plated in duplicate or triplicate in 96-well cell culture plates (Sigma, CLS3596). 180 μl of reporter cell suspension was added to each well to give a final volume of 200 ul and a final concentration HEK-blue TLR5 cells of $3 \times 10^4$. The assays were incubated at 37° C., 5% $CO_2$ for 22 h.

Following the incubation, 20 μl of the assay was added to 180 μl of Quantiblue (Invivogen, rep-qbl) substrate in a new 96-well plate and incubated at 37° C., 5% $CO_2$ for 2 h. The Quantiblue-containing plates were imaged on a microplate reader (Bio-Rad, iMark) taking 655 nm optical density readings. Results were averaged from technical replicates and then independent experiments averaged thereafter to provide data for final graphs.

Conclusions

Treatment with live and heat inactivated MRx0518 led to intermediate and high levels of TLR5 responses. These data show that the MRx0518 strain is able to induce a TLR5 response and that this response is not eliminated by heat inactivation. These data suggest flagellin from the genus *Enterococcus* and in particular MRx0518 flagellin can elicit a TLR5 response and that the flagellin is heat stable.

Figure 6:
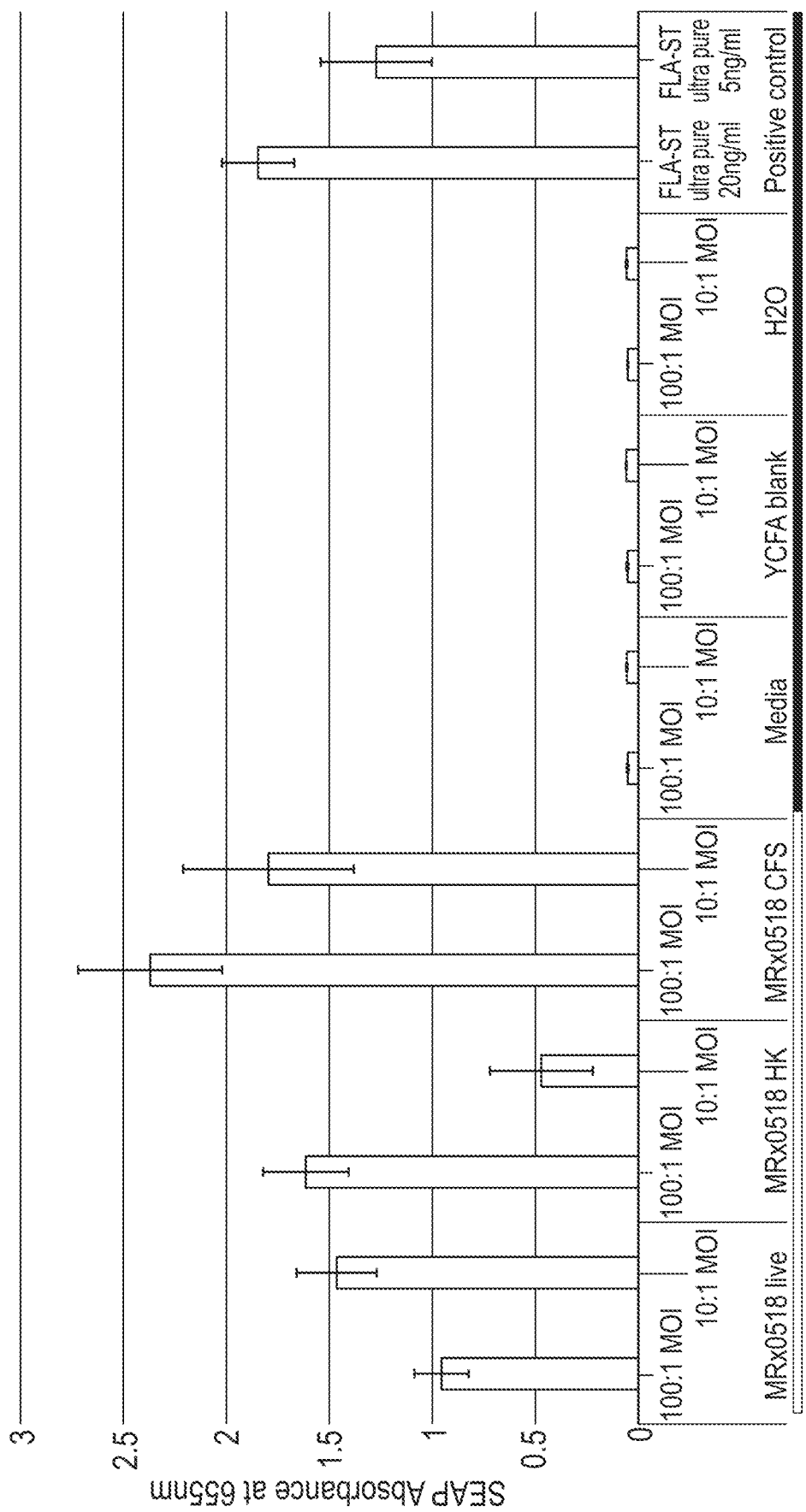
FIG. 6: MRx0518 activation of TLR5 reporter cells.
Figure 7:
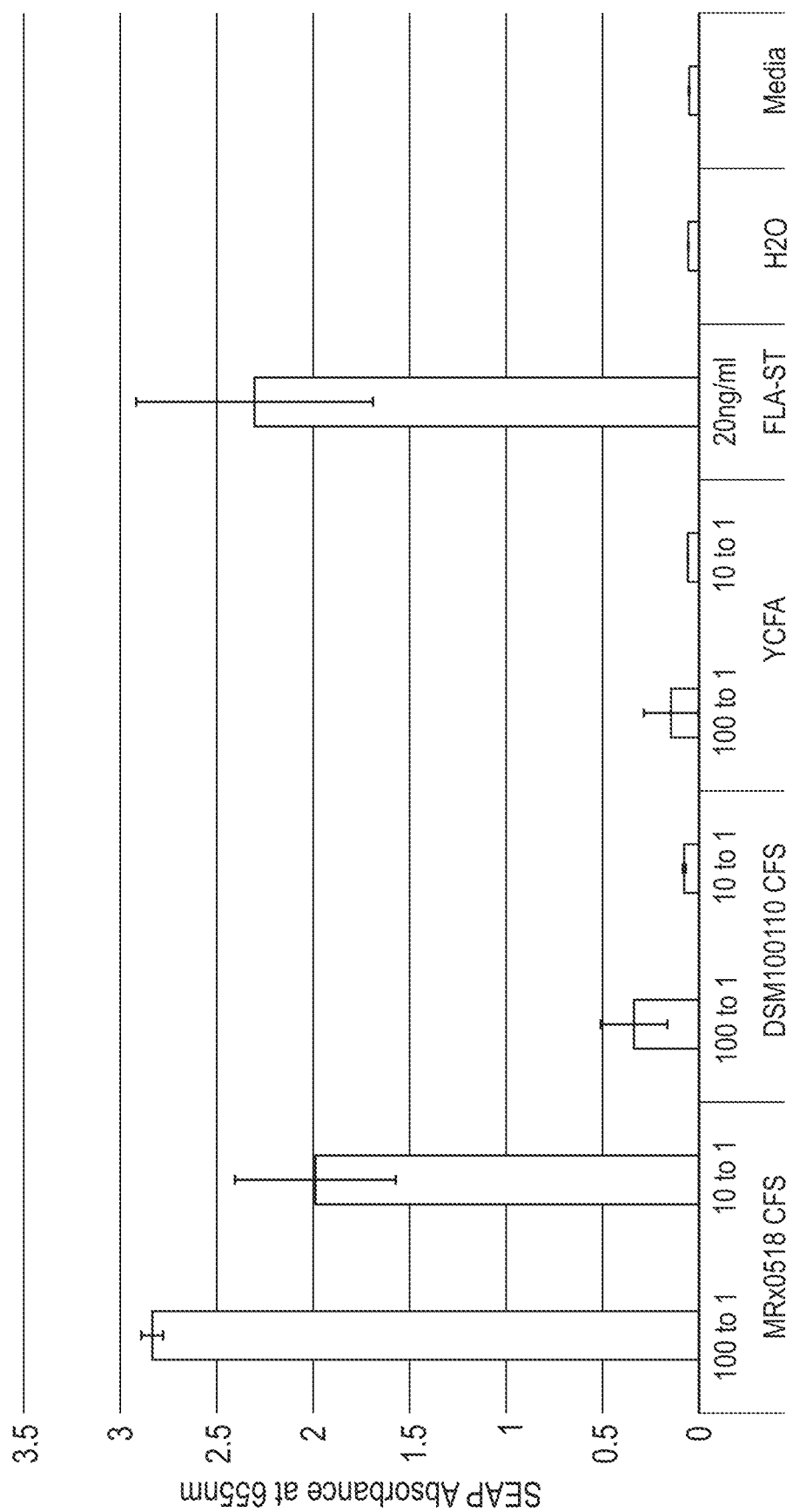
FIG. 7: Strain specific activation of TLR5 reporter cells.

The highest level of TLR5 activity was observed after treatment with MRx0518-CFS and was even higher than the known TLR5 agonist FLA-ST (FIG. 6). The CFS contains MRx0518 flagella shed into the supernatant. These data show that flagellin from the genus *Enterococcus* and in particular from MRx0518 produce a very strong TLR5 response, and so may be useful in therapy, in particular in the treatment of cancer. These data also show that MRx0518 is effective at shedding its flagellin into the supernatant.

Example 2—TLR5 Activation by the CFS is Particularly Strong for MRx0518

Summary

This study tested whether TLR5 activation using the CFS varies between strains. Both MRx0518 and DSM100110 are flagellated *Enterococcus gallinarum* strains. A study was conducted to observe if the CFS from both these strains leads to a TLR5 response.

TLR5 Activation Assay

A TLR5 assay as described in Example 1 was performed.

Procedure

The TLR5 activation assay was performed with the following treatments at two dosages—10:1 and 100:1:

MRx0518-CFS

DSM100110-CFS

Three negative controls were performed with antibiotic-free media, YCFA and water. A positive control was performed with ultrapure FLA-ST at a concentration of 20 ng/ml. For all treatments three replicates were performed.

Conclusions

MRx0518-CFS was able to stimulate a high TLR5 response. DSM100110-CFS also produced a TLR5 response at an MOI of 100:1, although it was reduced relative to MRx0518-CFS. These data show that while supernatant from both strains elicited an immunostimulatory response, this varies between strains. These data are surprising as strains MRx0518 and DSM100110 are both flagellated *Enterococcus gallinarum* strains. The MRx0518-CFS produces a higher TLR5 response compared to DSM100110-CFS, potentially because MRx0518 has an improved ability to shed its flagellin into the supernatant compared to other *Enterococcus gallinarum* strains, which may make it particularly useful in therapy.

These data suggest that flagellin polypeptides from the genus *Enterococcus* may be effective for use in treating or preventing cancer, in particular cancers that are associated with TLR5, such as breast, colorectal and gastric cancer.

Example 3—TLR5 Activation after Trypsin Treatment

Summary

Figure 8:
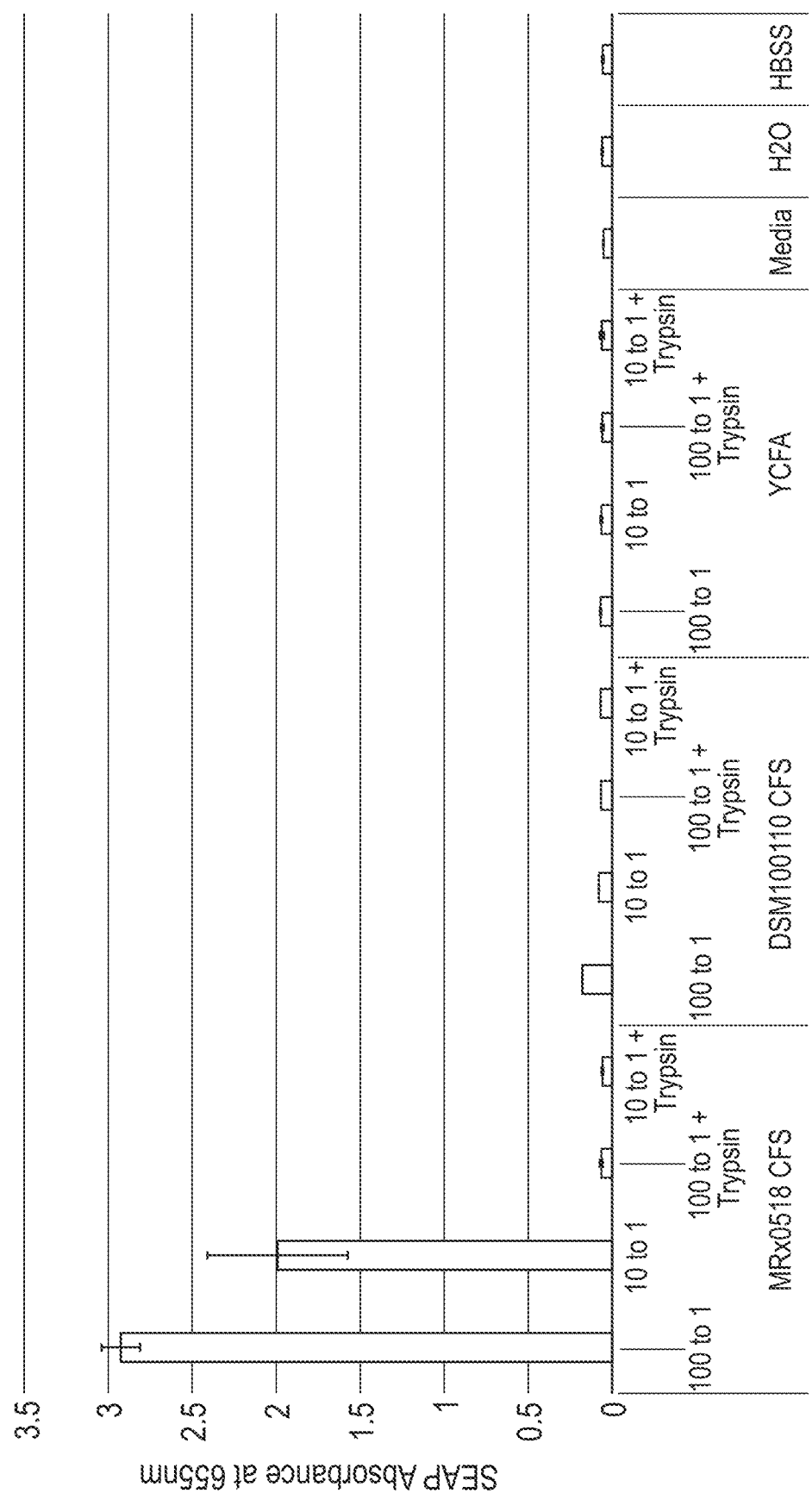
FIG. 8: TLR5 response of CFS from MRx0518 and DSM100110 after Trypsin-treatment.

This study tested whether MRx0518-CFS activation of TLR5 is trypsin-dependent.
TLR5 Activation Assay
  A TLR5 assay as described in Example 1 was performed.
Procedure
  The TLR5 activation assay was performed with the following treatments at two dosages—10:1 and 100:1 alone or in combination with trypsin:
  MRx0518-CFS
  DSM100110-CFS
  YCFA
  For all treatments three replicates were performed.
  CFSs were digested with 500 μg/ml trypsin (0.22 um filtered, Sigma, T3924), or an equivalent volume of trypsin vehicle (Hank's balanced salt solution, Fisher Scientific, 1175129) as a mock digest control, for 1 hr at 37° C., 5% $CO_2$. After incubation digested and mock digested CFS samples were supplemented with FBS to a final concentration of 10% (v/v) to inhibit trypsin activity.
  Three negative controls were performed with antibiotic-free media, HMS and water. A positive control was performed with ultrapure FLA-ST at a concentration of 20 ng/ml.
Conclusions
  TLR5 activation by MRx0518-CFS was abolished by treatment with trypsin (FIG. 8). These data show that the TLR5 response is activated by proteins in the MRx0518-CFS. Degradation of these proteins by trypsin abolishes the TLR5 response. The MRx0518 flagellin protein (FlaA$_{MRx0518}$) contains 36 trypsin cleavage sites, some of which are located in the TLR5 interaction domains.

Example 4—TLR5 Activation with Purified Flagellin Proteins

Summary

Figure 9A:
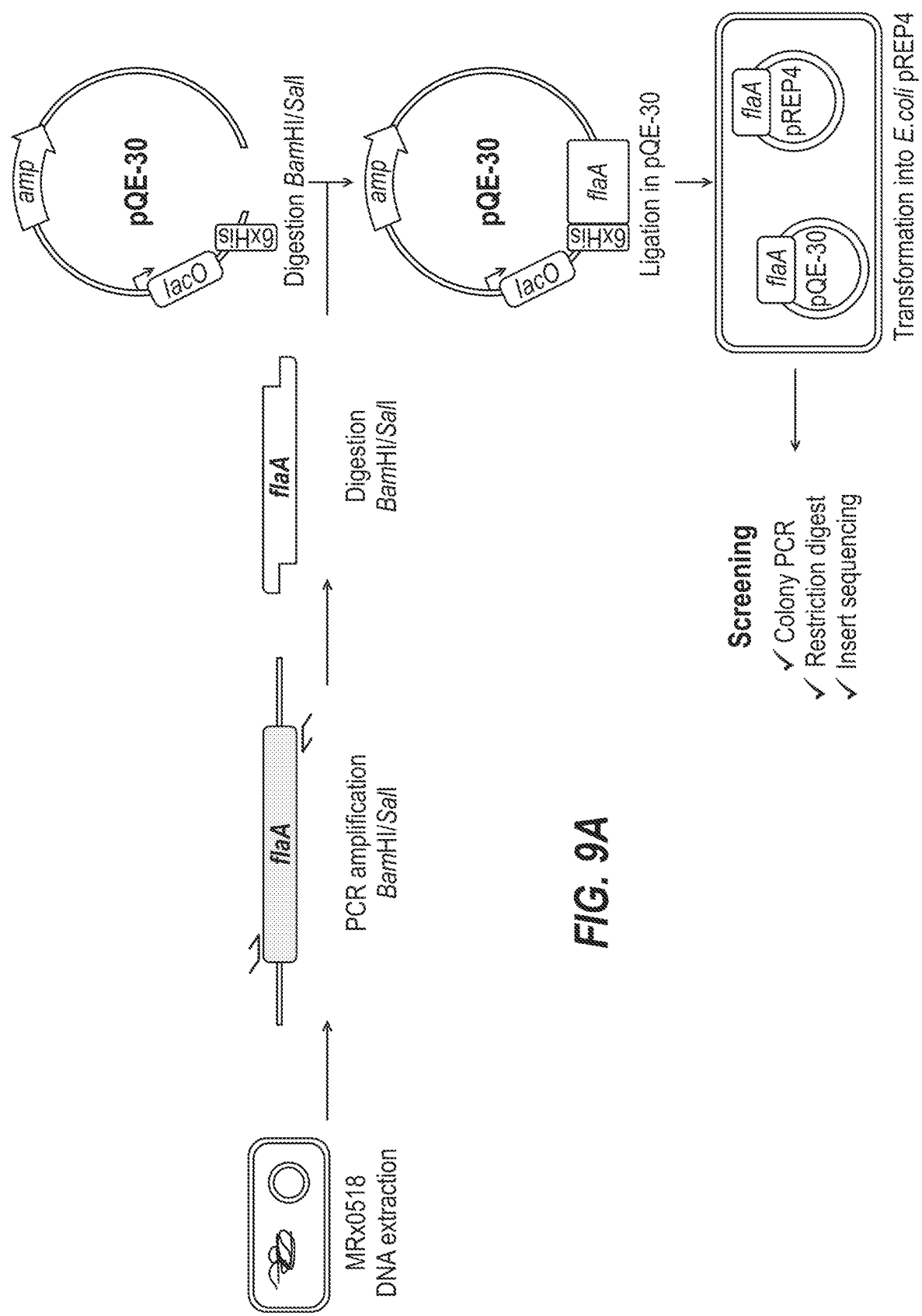
FIGS. 9A-9B: Cloning strategy for the production of recombinant flagellin proteins in *E. coli* (FIG. 9A) ("6×His" disclosed as SEQ ID NO: 49); Quality assessment of purified recombinant flagellin proteins, FlaA$_{MRx0518}$ and FlaA$_{DSM100110}$ on an SDS-PAGE gel (FIG. 9B).

This study tested the stimulatory profiles of purified MRx0518 and DSM100110 flagellin.
Production of Recombinant Flagellin Proteins
  An overview of the cloning strategy is shown if FIG. 9a. The full length genes for MRx0518 and DSM100110 flagellin were cloned into the recombinant expression construct pQE-30 (which has an N-terminal 6×His tag (SEQ ID NO: 49) using a restriction enzyme digest to produce pQE-30-FlaA$_{MRx0518}$ and pQE-30-FlaA$_{DSM100110}$ constructs. Positive colonies were identified using colony PCR, restriction enzymes digests and DNA sequencing techniques well-known in the art.

Figure 9B:
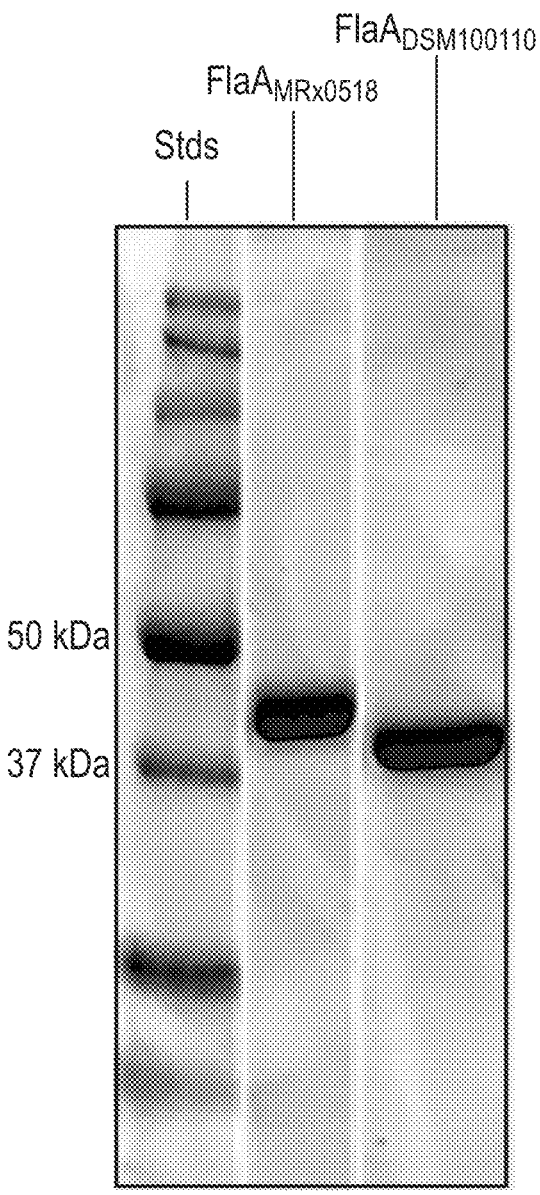

Recombinant flagellin proteins, FlaA$_{MRx0518}$ and FlaA$_{DSM100110}$, were expressed in *E. coli* cells and purified using an Immobilized Metal Affinity Chromatography and imidazole elution, followed by endotoxin removal (see table below). This results in high purity preparations with minimal endotoxin levels. The size and purity of the proteins was confirmed using an SDS-PAGE gel (FIG. 9b).

|  | FlaA$_{MRx0518}$ | FlaA$_{DSM100110}$ | Vehicle |
|---|---|---|---|
| Volume (ml) | 5 | 10 | 10 |
| Protein amount (mg) | 3.13 | 6.26 | 0 |
| Protection concentration (mg/ml) | 0.625 | 0.626 | 0 |
| Endotoxin | 0.88 | 0.99 | 0 |
| Buffer | PBS | PBS | PBS |
| SDS-PAGE | Minor contaminants | Minor contaminants | No band |

Figure 10:
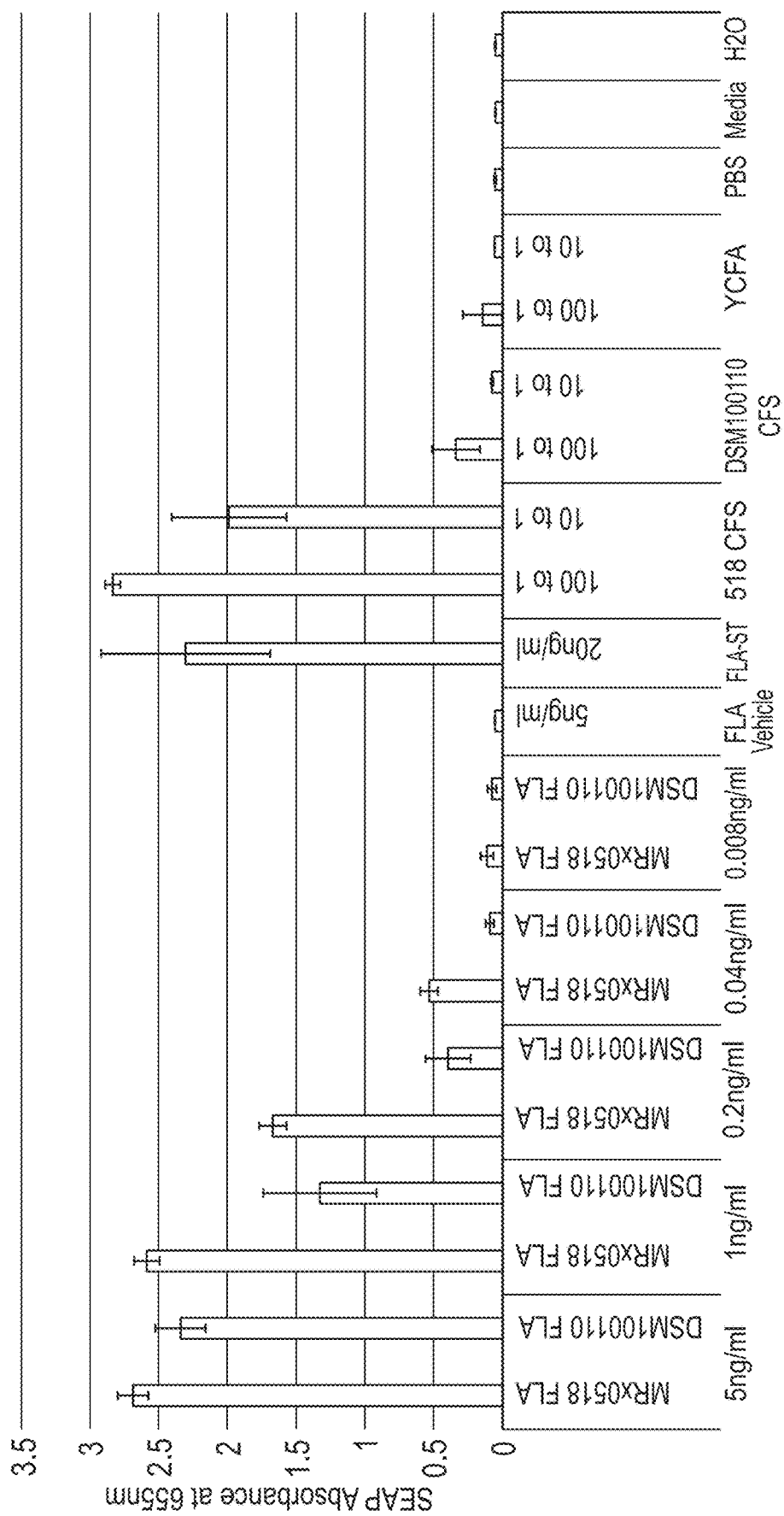
FIG. 10: Comparison of TLR5 activation with FlaA$_{MRx0518}$, FlaA$_{DSM100110}$ and CFS from MRx0518 and DSM100110.

Dose Response to Purified Recombinant FlaA$_{MRx0518}$ and FlaA$_{DSM100110}$ Proteins
  A TLR5 assay as described in Example 1 was performed.
Procedure
  The TLR5 activation assay was performed with the following treatments:
  Recombinant purified FlaA$_{MRx0518}$ at concentrations of 5, 1, 0.2, 0.04 and 0.008 ng/ml
  Recombinant purified FlaA$_{DSM100110}$ at concentrations of 5, 1, 0.2, 0.04 and 0.008 ng/ml
  A negative control was performed with a FLA vehicle at a concentration 5 ng/ml and a positive control was performed with ultrapure FLA-ST at a concentration of 20 ng/ml. For each treatment three replicates were performed.
Conclusions
  Both recombinant FlaA$_{MRx0518}$ and FlaA$_{DSM100110}$ can activate TLR5 responses. FIG. 10 compares the TLR5 activation with different dosages of recombinant FlaA$_{MRx0518}$ and FlaA$_{DSM100110}$ with the treatments described in examples 3 and 4. At a concentration of 5 ng/ml, both recombinant flagellin proteins can produce a TLR5 response that is higher than produced by the well-known TLR5 agonist FLA-ST being used a higher concentration (20 ng/ml). These data show that flagellin polypeptides from the species *Enterococcus gallinarum* are more effective at activating a TLR5 response than *S. typhimurium*. Flagellin polypeptides from *S. typhimurium* are known to suppress tumour growth through TLR5 activation. These data therefore suggest that flagellin polypeptides from *Enterococcus gallinarum* are more effective than flagellin polypeptides from *S. typhimurium* at treating or preventing cancer.

FlaA$_{MRx0518}$ and FlaA$_{DSM100110}$ have different immunostimulatory profiles. At concentrations of 1 ng/ml and 0.2 ng/ml FlaA$_{MRx0518}$ produces approximately five times more potent TLR5 response than FlaA$_{DSM100110}$. Both MRx0518 and DSM100110 are highly related strains. Both are flagellated *Enterococcus gallinarum* strains, however they express fundamentally different flagellin that have different immunostimulatory profiles. The surprising finding that FlaA$_{MRx0518}$ is strong TLR5 activator shows that this flagellin polypeptide is particularly effective at treating or preventing cancer.

These examples demonstrate that flagellin polypeptides from the genus *Enterococcus* are agonists for TLR5. TLR5 agonists have been implicated in treating T and B cell lymphomas. Therefore, flagellin polypeptides from the genus *Enterococcus* may be particularly effective at treating or preventing T and B cell lymphomas.

TLR5 activation has been shown to ameliorate radiation induced tissue damage. The examples show that flagellin polypeptides from the genus *Enterococcus* are strong activators of the TLR5 response. Therefore, flagellin polypeptides from the genus *Enterococcus*, and in particular the species *Enterococcus gallinarum*, may be particularly effective at ameliorating radiation induced tissue damage.

Example 5—Production of MRx0518 flaA$^-$ Mutant

Summary

An insertion mutant of MRx0518 was created which disrupted the flagellin gene.

Experimental Conditions

Figure 13:
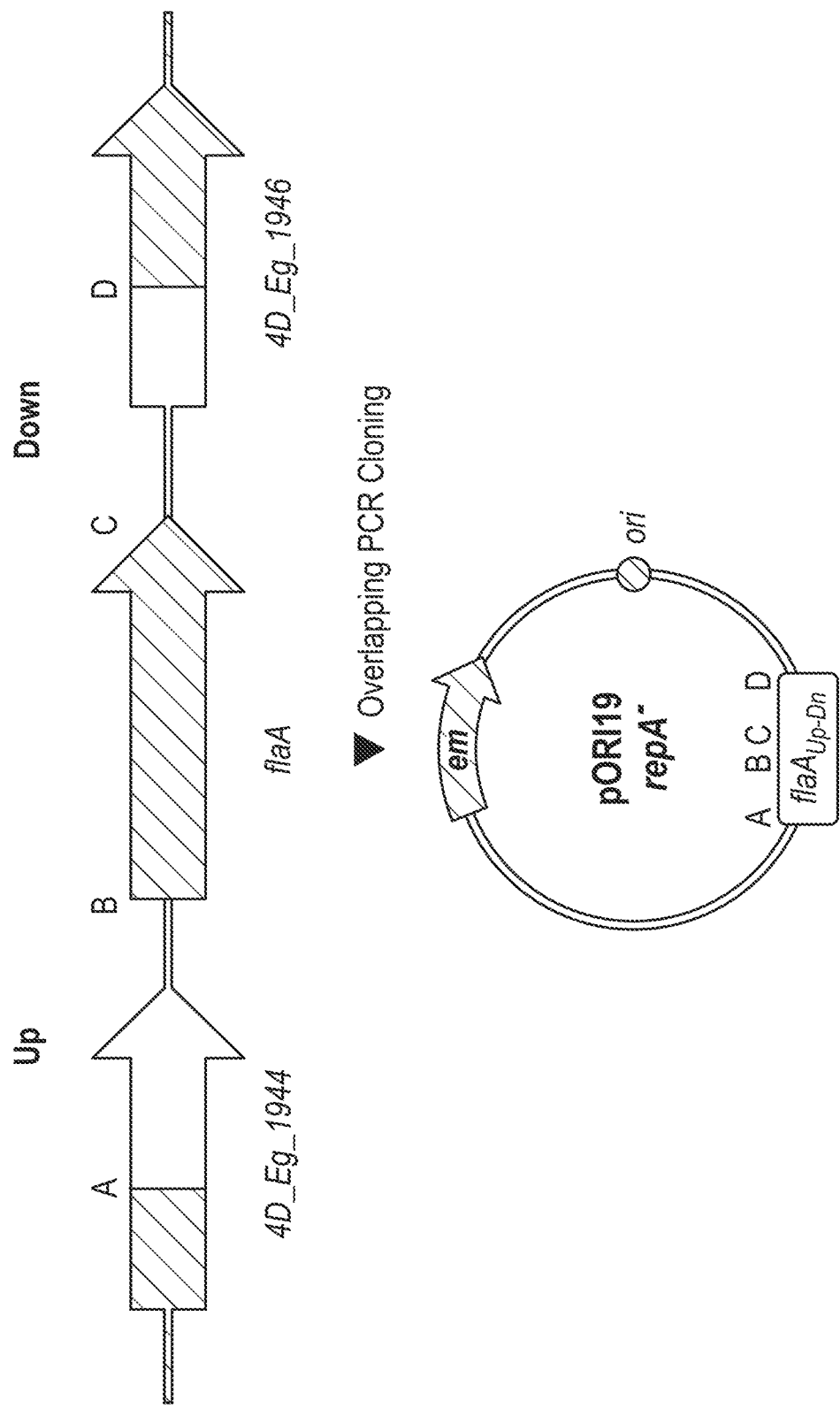
FIG. 13: flaA mutation strategy.

An internal fragment of flaA was cloned into vector pORI19 (repA). The resulting vectors flaA$_{MRx0518}$int-pORI19 was transformed into MRx0518 with and the insert integrated into the bacterial genome using homologous recombination (see FIG. 13).

Figure 11:
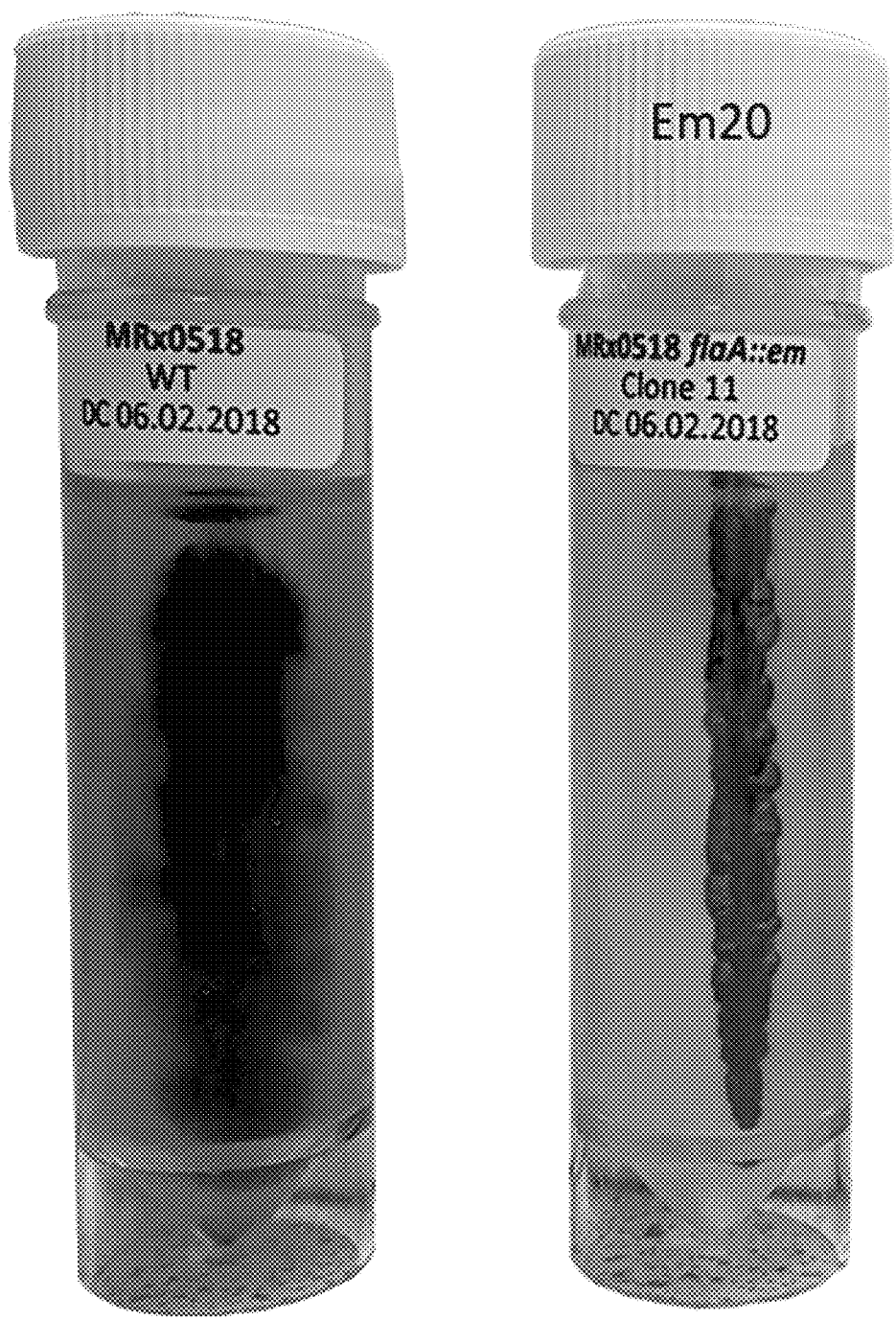
FIG. 11: Phenotypic Characterisation of MRx0518 flaA⁻ mutant.

Positive colonies were screened for the presence of the em gene and using PCR and further confirmed using sequencing. Phenotypic analysis of the mutants using motility assays also confirmed the insertion mutant MRx0518 flaA$^-$. The insert contains erythromycin resistance from the pORI19 vector. FIG. 11 shows that MRx0518 flaA$^-$ mutant is non-motile on BBL motility agar supplemented with 20 µg/ml erythromycin compared to wild type.

Example 6—Activation of TLR5 is Eliminated in the MRx0518 Mutant

Summary

The ability of CFS from the MRx0518 flaA$^-$ mutant to activate a TLR5 response was tested.

TLR5 Activation Assay

A TLR5 assay as described in Example 1 was performed.

Procedure

The TLR5 activation assay was performed with the following treatments at two dosages—10:1 and 100:1:
MRx0518-CFS
MRx0518 flaA$^-$-CFS Positive controls were performed with ultrapure FLA-ST at a concentrations of 5 ng/ml and 20 ng/ml. A negative control was performed with YFCA at two dosages—10:1 and 100:1. For all treatments three replicates were performed.

Conclusions

Figure 12:
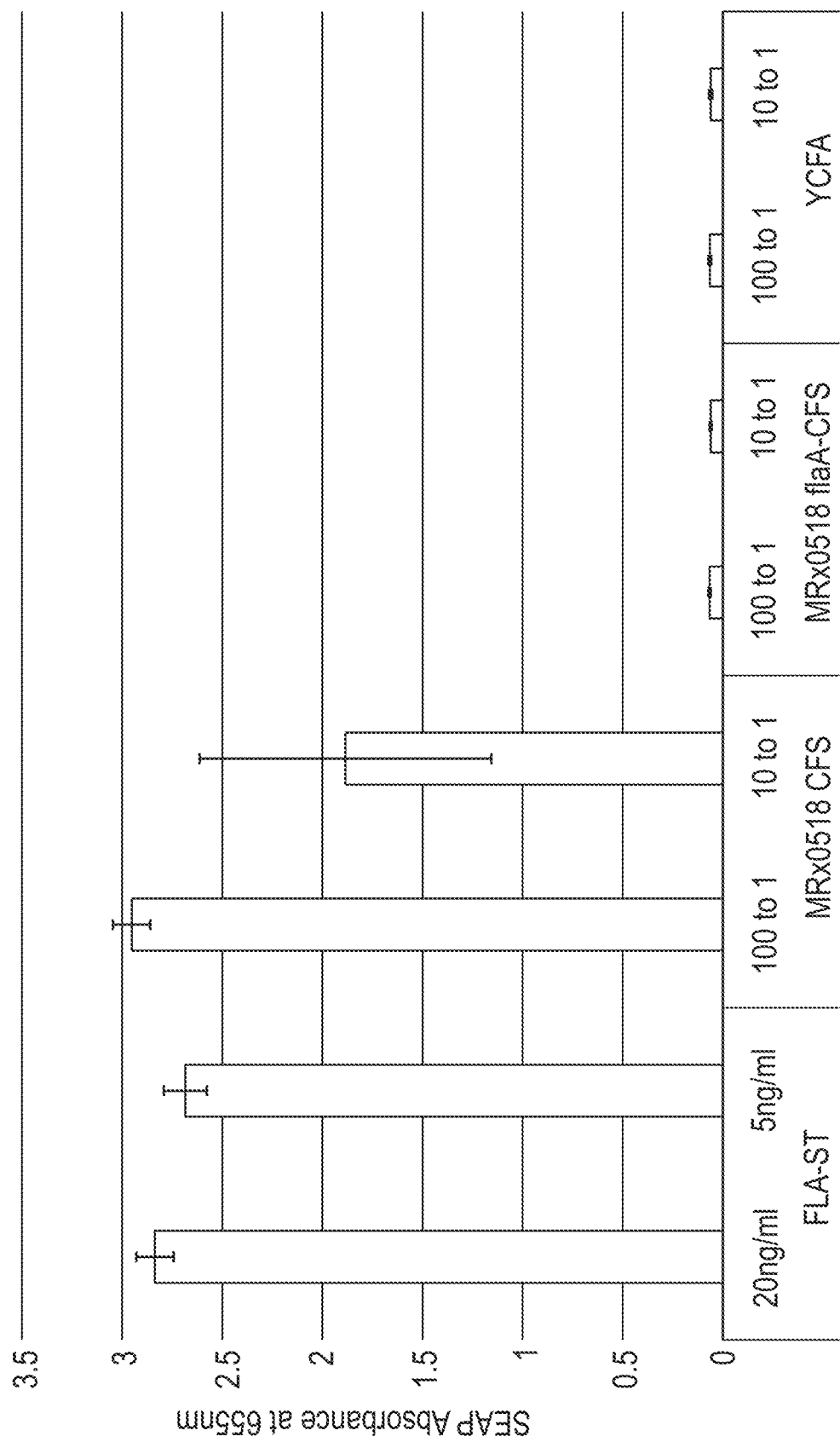
FIG. 12: TLR5 activation with MRx0518 flaA⁻ mutant CFS.

The ability of MRx0518-CFS to stimulate a TLR5 response was eliminated in the MRx0518 flaA$^-$ mutant (FIG. 12). These data show flagellin polypeptide is essential for the activation of the TLR5 response by MRx0518-CFS.

Example 7—Characterisation of MRx0518

Summary

Bacteria morphology such as size, presence or absence of fimbrae/flagella/pilli, or the presence of extracellular matrix influence both motility and adherence and are therefore important in the characterization of bacteria.

MRx0518 cultures were examined at the electron microscope level (Scanning and Transmission) to allow visualization of bacteria structure at a higher resolution and magnification than that allowed by conventional light microscopy methods.

Methodology

Transmission Electron Microscopy

An aliquot of MRx0518 bacterial culture in the exponential phase was received directly from an anaerobic hood in a sealed Eppendorf. Cultures were fixed in freshly made ice cold 2.5% Glutaraldehyde 0.1M Na Cacodylate pH 7.2. The Eppendorf was inverted gently a number of times before being placed on ice and left to fix for 3-5 minutes. Following fixation the bacteria were centrifuged briefly to pellet and resuspended in milli pure water. Using a glass pipette one drop of the fixed culture was applied to Formvar coated 300 mesh Cu grids. The bacteria were allowed to settle and adsorb for approximately 1-2 minutes and the excess solution removed from the grid using Whatman No 3 filter paper. 10 µl 2% Uranyl acetate was applied to the grid for a few seconds and removed by capillary action using filter paper as above. The grids were allowed to dry completely before being examined in a Philips CM100 TEM at varying kV.

Scanning Electron Microscopy

An aliquot from the same culture as above was taken for SEM analysis. The bacteria were fixed as above but not pelleted. SPI PORE FILTERs (25 mm diameter, 0.2 um pore size) were pretreated with 0.01% poly-lysine immediately before the fixed bacteria were pushed through using a Luer-Lok syringe onto the filter. This was followed by gently pushing 1 ml milli pure water through the filter. The filters were cut to size and dehydrated through a series of ethanol solutions (50%, 70% 90% and 3×100%) The filters were then immersed sequentially through increasing concentrations of hexamethyldisilazane (HMDS 25%, 50%, 75% in ethanol) with the final dehydration step carried out using 100% HMDS. This was allowed to evaporate overnight. The filters were critical point dried and coated with 10 nm gold palladium before being examined in a Zeiss EVO MA10 Scanning Electron Microscope.

Conclusions

Both methods of visualization at the electron microscope level showed MRx0518 to have flagella (FIG. 14). Both TEM and SEM analysis showed MRx0518 to have flagella (solid white arrows). The cell size ranged between 1-2 µm. The presence of outer membrane vesicles was only apparent in the SEM images of MRx0518. The SEM image shows what appears to be outer membrane vesicles (white dashed arrow).

Example 8—Activation of Murine TLR5 by Recombinant Flagellin Proteins from *Enterococcus gallinarum* Strains MRx0518 and DSM 100110

Summary

MRx0518 is a bacterial strain isolated from a human sample, whereas DSM 100110 is of murine origin. The ability of the recombinant flagellin proteins from the *Enterococcus gallinarum* strains MRx0518 and DSM 100110 to activate murine TLR5 was tested.

Methodology

Recombinant purified MRx0518 (FliC$_{MRx0518}$) and DSM 100110 (FliC$_{DSM100110}$) were produced as described in Example 4.

A TLR5 assay as described in Example 1 was performed. The TLR5 activation assay was performed with the following treatments:

Recombinant purified FliC$_{MRx0518}$ at concentrations of 5, 1, 0.2, 0.04 and 0.008 ng/ml Recombinant purified FliC$_{DSM100110}$ at concentrations of 5, 1, 0.2, 0.04 and 0.008 ng/ml Three independent replicates were performed.

Conclusions

Figure 15:
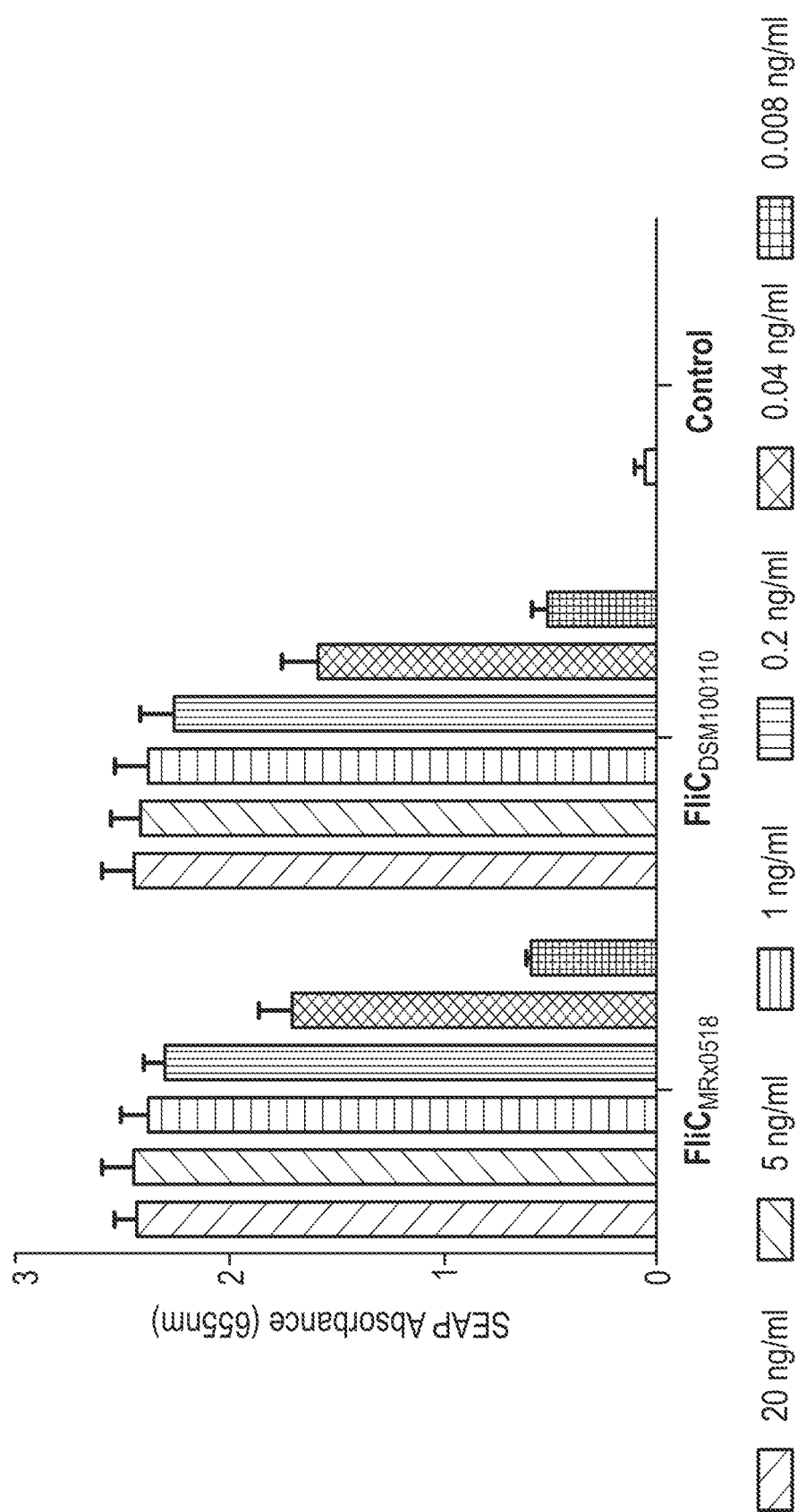
FIG. 15: Activation of murine TLR5 by recombinant flagellin proteins from MRx0518 and DSM 100110. Data is representative of three independent replicates.
Figure 17:
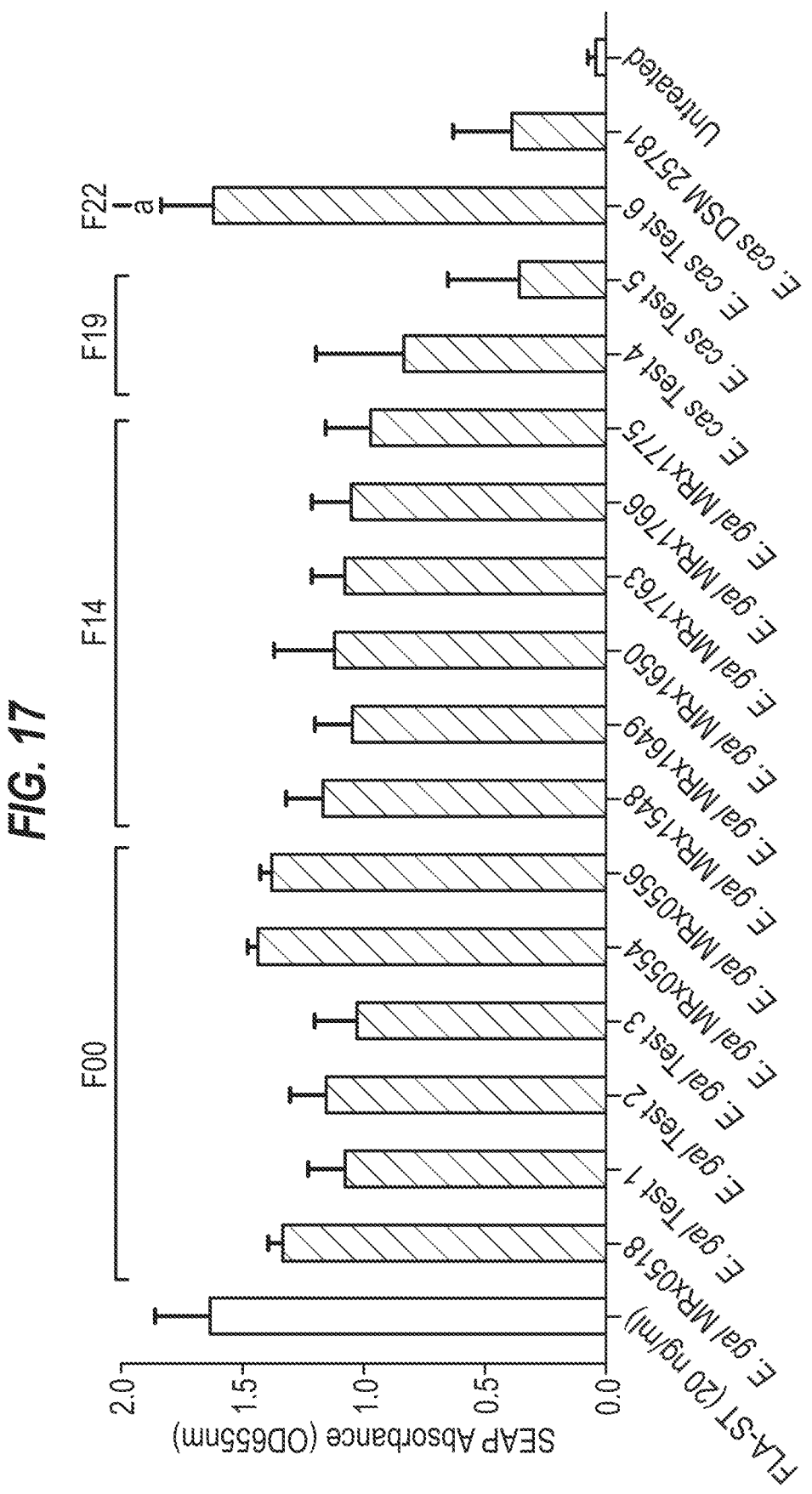
FIG. 17: Activation of human TLR5 by motile *E. gallinarum* and *E. casseliflavus* strains. Data represents the average and standard deviation of 3 biological replicates. Significance was assessed by one-way ANOVA test—"a" denotes $p<0.0001$.

Both $FliC_{MRx0518}$ and $FliC_{DSM100110}$ activated murine TLR5 and there was no difference in the activation levels between $FliC_{MRx0518}$ and $FliC_{DSM100110}$ at any dose (FIG. 15). This effect is different to the results observed for the activation of human TLR5 by $FliC_{MRx0518}$ and $FliC_{DSM100110}$. As shown in Example 4, FIG. 10, $FliC_{MRx0518}$ can stimulate human TLR5 to greater levels than $FliC_{DSM100110}$ at concentrations of 1 ng/ml and lower. Without being bound by any particular theory, the different activation profiles of human and murine TLR5 by recombinant flagellin proteins from different *Enterococcus gallinarum* strains may be due to sequence differences between $FliC_{MRx0518}$ and $FliC_{DSM100110}$, as well as binding site variability between human and murine TLR5.

As shown in FIG. 3, the inventors have noted that the majority of the sequence variation between different flagellin polypeptides is observed in the D2-D3 region. A sequence alignment of $FliC_{MRx0518}$ and $FliC_{DSM100110}$ shows a large variation in the D2-D3 domain (FIG. 16). The alignment was performed using CLUTAL OMEGA v1.2.4 multiple sequence alignment software.

Example 9—Immunostimulatory Capability of Motile *E. gallinarum* and *E. casseliflavus* Strains Derived from Humans Summary The ability of motile *E. gallinarum* and *E. casseliflavus* strains derived from humans to activate human TLR5 in vitro was assessed.

Methodology

Bacterial Strains Tested

| Strain Name | Species |
| --- | --- |
| MRx0518 | *E. gallinarum* |
| Test 1 | *E. gallinarum* |
| Test 2 | *E. gallinarum* |
| Test 3 | *E. gallinarum* |
| MRx0554 | *E. gallinarum* |
| MRx0556 | *E. gallinarum* |
| MRx1548 | *E. gallinarum* |
| MRx1649 | *E. gallinarum* |
| MRx1650 | *E. gallinarum* |
| MRx1763 | *E. gallinarum* |
| MRx1766 | *E. gallinarum* |
| MRx1775 | *E. gallinarum* |
| Test 4 | *E. casseliflavus* |
| Test 5 | *E. casseliflavus* |
| Test 6 | *E. casseliflavus* |
| DSM25781 | *E. casseliflavus* |

The MRX and test strains were isolated from one of four donors from the 4D Pharma culture collection (donor numbers FOO, F14, F19 and F22).

TLR5 Assay Conditions

The bacterial strains were cultured in YCFA broth (E&O Laboratories, Bonnybridge, Scotland, UK) until they reached stationary growth phase. Cells and supernatants were separated by centrifugation at 5,000×g for 5 mins. Supernatants were passed through a 0.22 µm filter and diluted in water.

HEK-Blue™-hTLR5 cells (InvivoGen, San Diego, CA, USA) were routinely cultured in DMEM supplemented with 10% FBS, 4 mM L-glutamine, 4.5 mg/ml glucose, 100 U/ml penicillin, 100 µg/ml streptomycin, 100 µg/ml Normocin™ (InvivoGen), 30 µg/ml blastocidin (InvivoGen) and 100 µg/ml zeocin (InvivoGen) to 90% density. Cell lines were cultured at 37° C. and 5% $CO_2$. All reagents were supplied by Sigma-Aldrich, Gillingham, England, UK unless otherwise stated.

For co-cultures, cells grown to 90% density were washed once with phosphate-buffered saline (PBS) (Sigma-Aldrich) and resuspended in growth media without antibiotic at a density of 140,000 cells/ml. Supernatants were added to cells at a multiplicity of infection (MOI) equivalent of 100:1. The assay positive control, *Salmonella Typhimurium* flagellin (FLA-ST) (InvivoGen), was used at 20 ng/ml. Cells were incubated with supernatants at 37° C. in a 5% $CO_2$ atmosphere for 22 h. QUANTI-Blue™ (InvivoGen) was added, plates were incubated for a further 2 h and optical density at 655 nm was recorded. Three independent biological replicates were carried out for all strains. The data in FIG. 18 represents three independent replicates.

Conclusions

All of the supernatants of the *E. gallinarum* and *E. casseliflavus* strains tested were able to potently activate a TLR5 response compared to the untreated control. Of the three *E. casseliflavus* strains tested, Test 6 was found to strongly activate a TLR5 response, while Test 5 and DSM25781 elicit less potent TLR5 responses.

Example 10—Activation of NF-κB by MRx518

The ability of the bacterial strain MRx0518 to activate NF-κB was investigated. The results are presented in FIG. 18. MRx0518 supernatant was the most potent activator of NF-κB. The activation of NF-κB was eliminated after treatment with trypsin.

These data show that flagellin from the genus *Enterococcus* and in particular from MRx0518 produce a very strong NF-κB response, and so may be useful in therapy.

Example 11—T Cell Differentiation

The ability of MRx0518 to induce T-cell differentiation was explored in vitro on peripheral blood mononuclear cells (PBMCs, Stemcell, Cat: 70025).

Methodology

PBMCs were plated in 96-well plates plated with anti-CD3 (Ebioscience, CD3 monoclonal antibody (OKT3 clone), functional grade, cat. No. 16-0037-81) at 400,000/ well in 50 µl cRPMI medium per well (cRPMI contains RPMI 1640 (+L-Glut, 21875-034) 2 mM final conc. Stock 200 mM.; 10% HI FBS (Gibco life technologies, 10082-147); 50 µm mercaptoethanol (Gibco life technologies, 21985-023); and 1% pen/strep (P4333, 10 mg/ml). MRx518 supernatant was then added to each well, 4,000,000 in 100 µl/well. Supernatants were passed through a 0.22 µm filter and diluted appropriately in co-culture.

Following 3 days in a 37° C. incubator, the cells were removed and re-suspended in a medium containing PMA—(Sigma, Cat no. P8139), Ionomycin (Sigma, Cat no. I3909) and GolgiSTOP (BD, Cat no 554724) for 5 hours. PMA stock was 1 mg/ml in DMSO which was further diluted in 100 ug/ml (each sample required 50 ng/ml in cRPMI), Ionomycin stock was 1 mM in DMSO (1 µM in cRPMI was used) and GolgiStop concentration was used at 4 µl/6 ml.

The cells were then subjected to a flow cytometry staining:

After washing, the cells were incubated with Viobility 405/520 Fixable Dye from Miltenyi biotec (1 µl/sample)+ human Fc block, cat. 564219 (1 µl/sample) in PBS for 10 mins in the dark at room temperature. The surface antibodies (2 µl of each) were then added directly to the wells for 10 mins in the dark at room temperature—CD3-APC-Vio 770 (Miltenyi, cat. No. 130-113-136), CD4-VioBlue (Miltenyi, cat. No. 130-114-534) and CD25-VioBright FITC (Miltenyi, cat. No. 130-113-283). The cells were then washed twice in PBS and spun down at 300 g/5 min/RT.

The eBioscience FoxP3 transcription factor staining buffer was then used to fix and permeabilise the cells (cat. No. 00-5523). Following the eBioscience protocol, a perm/fix buffer was prepared using 1× concentrate and 3 diluent. The cells were fixed for 1 h at RT and then washed 2× in 1× Perm wash and spun down at 300 g/5 min/RT. The following intracellular staining or transcription factor antibodies were added to the samples in perm wash (1×) for 45 mis/dark/RT or in the fridge overnight (up to 18 h), followed by washing the antibodies 2× using Perm wash (300 µl) and re-suspension in PBS (250 µl) to acquire on the cytometer:

| Intracellular markers | Transcription factors |
|---|---|
| 2 ul IL10-PE | 5.5 ul FoxP3-PE-Cy7 |
| 2 ul IFNy-PE Vio770 | 9 ul Tbet-APC |
| 10 ul IL17a-APC | 9 ul RoRyt-PE |

Anti IFNγ-PE Vio770 human antibodies (Miltenyi, cat. No. 130-114-025)
Anti IL10-PE human antibodies (Miltenyi, cat. No. 130-112-728)
Anti IL17a-APC human antibodies (Miltenyi, cat. No. 130-099-202)
Anti RoRyt-PE human antibodies (Miltenyi, cat. No. 130-103-837)
Anti Tbet-APC human antibodies (Miltenyi, cat. No. 130-098-655
Foxp3 monoclonal antibody (236A/E7), Pe cy7 (ebioscience) cat. No. 25-4777-41

Conclusions

Figure 19:
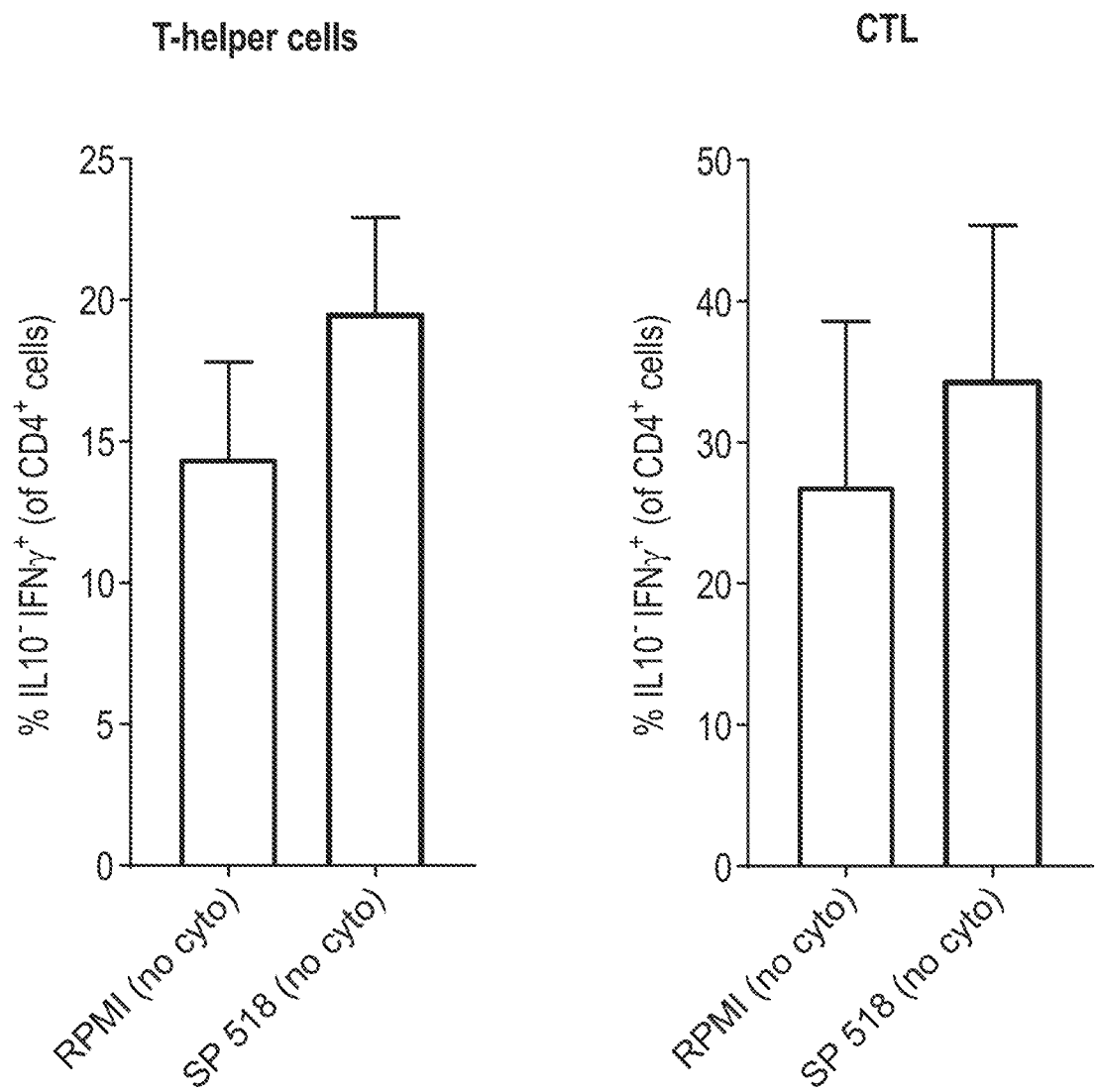
FIG. 19: Induction of T-cell differentiation in a population of (A) T-helper cells and (B) Cytotoxic T Lymphocytes (CTL) using Supernatant from MRx518 and RPMI medial as a control, without addition of cytokines (no cyto).

As can be seen in FIG. 19, MRx518 supernatant (SP 518) can induce the differentiation of T helper cells and cytotoxic T cells.

Figure 20:
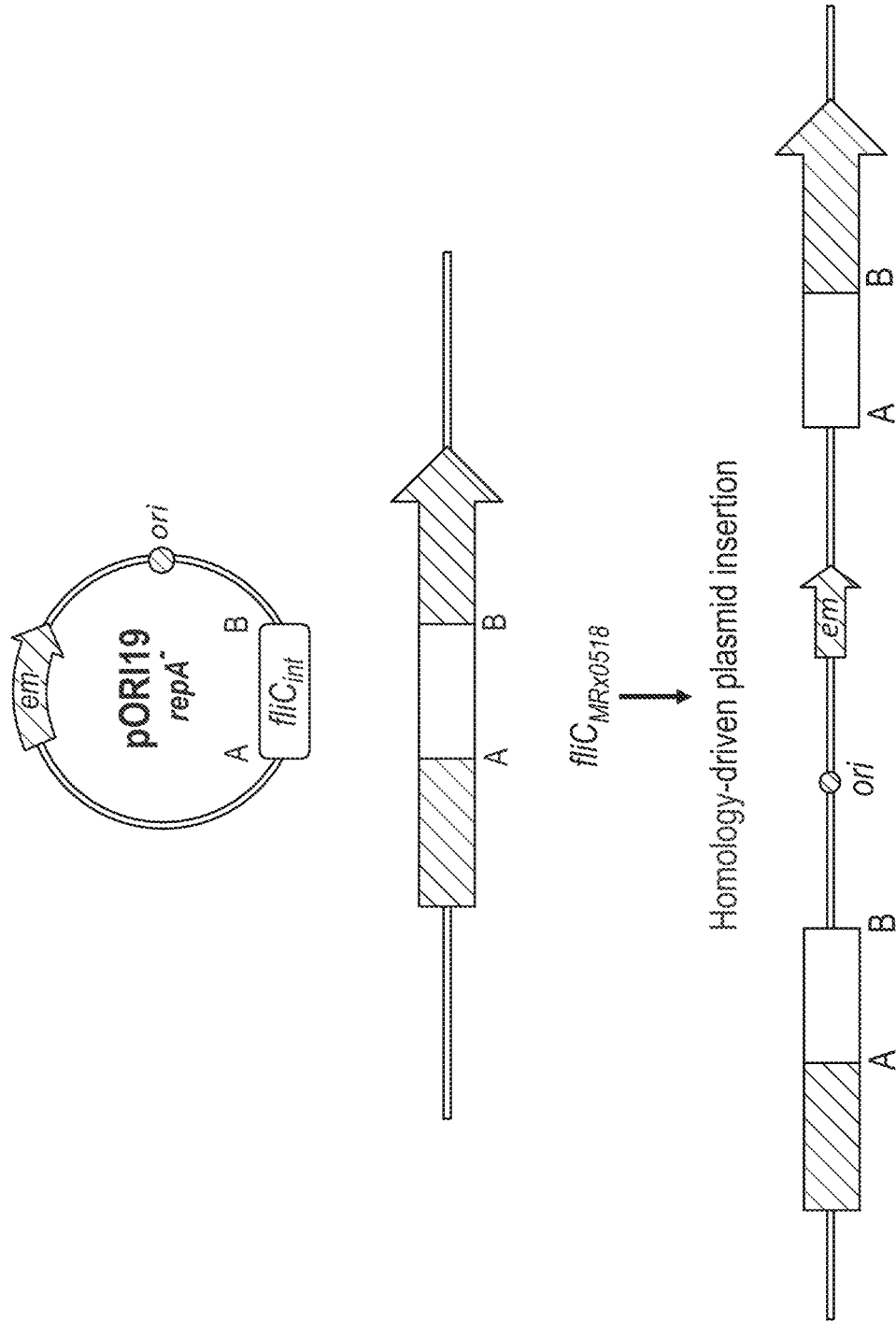
FIG. 20: An alternative flaA mutation strategy.

Example 12—Generation of an *E. gallinarum* MRx0518 Flagellin Gene Insertion Mutant This example provides an alternative strategy for inactivating the flagellin gene compared to Example 5. The fliC gene was disrupted by homology-driven insertion of the suicide plasmid pORI19 (see FIG. 20). Insertion of pORI19 within the fliC gene was confirmed by DNA sequencing and the non-motile phenotype of the resulting mutant strain was confirmed in vitro.

Methodology

The flagellin insertion mutant was created using the non-replicative plasmid pORI19 (Emr repA− Ori+; cloning vector [118]). An internal fragment of *E. gallinarum* MRx0518 fliC gene was amplified using primers DC020 (SEQ ID NO: 43: CCCGGGG-GATCCGCGGTAAATGTTGCTAAAGCATCATCG) and DC021 (SEQ ID NO: 44: ACGACGGTCGACCCACAG-CATCTTAGGGCGTATGCG) and cloned into pORI19. Restriction enzymes and Quick Ligase (New England Biolabs, Ipswich, MA, USA) were used according to the manufacturer's instructions. This construct was propagated in *E. coli* EC101 by chemical transformation [118] and isolated using the Genopure Plasmid Maxi Kit (Roche Diagnostics, Basel, Switzerland) from a 500-ml culture. Isolated plasmid DNA was concentrated using 0.3 M sodium acetate pH 5.2 and ethanol down to 20 µl.

Electrocompetent cells were successfully generated by growing bacterial cultures in sub-inhibitory concentrations of glycine followed by mutanolysin and lysozyme treatments to further weaken the cell wall peptidoglycan layer. A protocol was developed to prepare *E. gallinarum* MRx0518 electrocompetent cells, which was adapted from a previously published method [119]. In brief, *E. gallinarum* MRx0518 was grown for 18 h in GM17 broth, supplemented with 0.5 M sucrose and 3% (w/v) glycine (Sigma-Aldrich). Cells were then washed twice with 0.5 M sucrose and 10% (v/v) glycerol and treated with 10 µg/ml lysozyme and 10 U/ml mutanolysin (Sigma-Aldrich) for 30 min at 37° C. *E. gallinarum* MRx0518 cells were then transformed by electroporation with 10 µg of plasmid DNA and recovered in BHI broth before plating on selective BHI agar. Positive colonies were screened for the presence of the em gene using primers DC047 (SEQ ID NO:45: CCAAAT-TAAAGAGGGTTATAATGAACGAG) and DC048 (SEQ ID NO:46: GATGCAGTTTATGCATCCCTTAAC). Plasmid insertion was confirmed for successful transformants by PCR amplification and sequencing (GATC Biotech, Konstanz, Germany) using primers DC013 (SEQ ID NO:47: CCGATAAATAGTAGCAGAGGGAAACC) and DC014 (SEQ ID NO:48: GGCTGAATATC-CATCAGAGCTTCCTC).

In vitro motility of the flagellin insertion mutant was assessed using BBL™ Motility Test Medium supplemented with 0.005% (w/v) 2,3,5-triphenyltetrazolium chloride (BD, Sparks, MD, USA). In brief, a fresh colony was stab-inoculated in 20 ml equilibrated media and incubated for 48 h at 37° C. in anaerobic conditions. All assays were performed in triplicate.

Sequences
SEQ ID NO:1—Flagellin polypeptide from *Enterococcus gallinarum* MRx0518
SEQ ID NO:2—Flagellin polypeptide from *Enterococcus gallinarum* DSM100110
SEQ ID NO:3—Flagellin polypeptide from *Enterococcus gallinarum* MRx0554
SEQ ID NO:4—Flagellin polypeptide from *Enterococcus gallinarum* MRx0556
SEQ ID NO:5—Flagellin polypeptide from *Enterococcus gallinarum* MRx1548
SEQ ID NO:6—Flagellin polypeptide from *Enterococcus gallinarum* MRx1650
SEQ ID NO:7—Flagellin polypeptide from *Enterococcus gallinarum* MRx1763
SEQ ID NO:8—Flagellin polypeptide from *Enterococcus gallinarum* MRx1766
SEQ ID NO:9—Flagellin polypeptide from *Enterococcus gallinarum* MRx1775
SEQ ID NO:10—Flagellin polypeptide from *Enterococcus gallinarum* MRx1886
SEQ ID NO:11—Flagellin polypeptide from *Enterococcus gallinarum* 2A8
SEQ ID NO:12—Flagellin polypeptide from *Enterococcus gallinarum* 9402
SEQ ID NO:13—Flagellin polypeptide from *Enterococcus gallinarum* A6981
SEQ ID NO:14—Flagellin polypeptide from *Enterococcus gallinarum* MRx1649
SEQ ID NO:15—Flagellin polypeptide from *Enterococcus gallinarum* EG2

SEQ ID NO:16—Flagellin polypeptide from *Enterococcus gallinarum* SKF1
SEQ ID NO:17—Flagellin polypeptide from *Enterococcus casseliflavus* DSM 7370
SEQ ID NO:18—Flagellin polypeptide from *Enterococcus casseliflavus* 1a6A
SEQ ID NO:19—Flagellin polypeptide from *Enterococcus casseliflavus* 3h10B
SEQ ID NO:20—Flagellin polypeptide from *Enterococcus casseliflavus* 14-MB-W-14
SEQ ID NO:21—Flagellin polypeptide from *Enterococcus casseliflavus* ATCC12755
SEQ ID NO:22—Flagellin polypeptide from *Enterococcus casseliflavus* DSM4841
SEQ ID NO:23—Flagellin polypeptide from *Enterococcus casseliflavus* DSM20680
SEQ ID NO:24—Flagellin polypeptide from *Enterococcus casseliflavus* EC10
SEQ ID NO:25—Flagellin polypeptide from *Enterococcus casseliflavus* EC20
SEQ ID NO:26—Flagellin polypeptide from *Enterococcus casseliflavus* EC30
SEQ ID NO:27—Flagellin polypeptide from *Enterococcus casseliflavus* F1129
SEQ ID NO:28—Flagellin polypeptide from *Enterococcus casseliflavus* F1129F46
SEQ ID NO:29—Flagellin polypeptide from *Enterococcus casseliflavus* NBRC 100478
SEQ ID NO:30—Flagellin polypeptide from *Enterococcus casseliflavus* PAVET15
SEQ ID NO:31—Flagellin polypeptide from *Enterococcus casseliflavus* NLAE-z1-G268
SEQ ID NO:32—Flagellin polypeptide from *Enterococcus casseliflavus* NLAE-z1-C414
SEQ ID NO:33—Flagellin polypeptide from *Enterococcus gallinarum* FDAARGOS-163
SEQ ID NO:34—Flagellin polypeptide from *Enterococcus casseliflavus* MRx0858
SEQ ID NO:35—Flagellin polypeptide from *Enterococcus casseliflavus* DSM25781
SEQ ID NO:36—Flagellin polypeptide from *Enterococcus gallinarum* DSM28564
SEQ ID NO:37—Flagellin polypeptide from *Enterococcus gallinarum* DSM28565
SEQ ID NO:38—Flagellin polypeptide from *Enterococcus gallinarum* F1213F 228
SEQ ID NO:39—Flagellin polypeptide from *Enterococcus gallinarum* DSM20718
SEQ ID NO:40—Flagellin polypeptide from *Enterococcus gallinarum* DSM20628
SEQ ID NO:41—Flagellin polypeptide from *Enterococcus gallinarum* NBRC100675
SEQ ID NO:42—Flagellin polypeptide from *Enterococcus gallinarum* DSM24841

REFERENCES

[1] Spor et al. (2011) *Nat Rev Microbiol.* 9(4):279-90.
[2] Eckburg et al. (2005) *Science.* 10; 308(5728):1635-8.
[3] Macpherson et al. (2001) *Microbes Infect.* 3(12):1021-35
[4] Macpherson et al. (2002) *Cell Mol Life Sci.* 59(12):2088-96.
[5] Mazmanian et al. (2005) *Cell* 15; 122(1):107-18.
[6] Chung & Kasper (2010) *Curr. Opin. Immunol.* 22: 455-460
[7] Macpherson (2006) *Curr. Top. Microbiol. Immunol.* 308: 117-136.
[8] Gaboriau-Routhiau et al. (2009) *Immunity.* 31: 677-689.
[9] Ivanov et al. (2009) *Cell* 139: 485-498
[10] Geuking et al. (2011) *Immunity* 34(5):794-806
[11] Atarashi et al. (2011) *Science,* 331, 6015, 337-341.
[12] Nutsch & Hsieh, (2012) *Current opinion in immunology,* 24, 4, 385-391.
[13] Prakash et al. (2011) *Cell host & microbe,* 10, 3, 273-284.
[14] Sczesnak et al. (2011) *Cell host & microbe,* 10, 3, 260-272.
[15] Hajam et al. (2017) Experimental & Molecular Medicine 49, e373;
[16] WO2012/097012
[17] Zheng et al. (2017) Science Translational Medicine 9
[18] WO2008/144889
[19] Frank et al. (2007) *PNAS* 104(34):13780-5.
[20] Scanlan et al. (2006) *J Clin Microbiol.* 44(11):3980-8.
[21] Kang et al. (2010) *Inflamm Bowel Dis.* 16(12):2034-42.
[22] Machiels et al. (2013) Gut. 63(8):1275-83.
[23] WO 2013/050792
[24] WO 03/046580
[25] WO 2013/008039
[26] WO 2014/167338
[27] Goldin and Gorbach (2008) *Clin Infect Dis.* 46 Suppl 2:S96-100.
[28] Azad et al. (2013) BMJ. 347:f6471.
[29] Strickertsson et al. (2014) *Genes* 5(3): 726-738.
[30] Lu et al. (2015). Functional properties of flagellin as a stimulator of innate immunity. Nat Publ Gr.
[31] Yonekura et al. (2003) *Nature* 424, 643-650.
[32] Jacchieri et al. (2003) *J Bacteriol* 185, 4243-7.
[33] Smith et al. (2003) *Nat Immunol* 4, 1247-1253.
[34] Yoon et al. (2013). *NIH Public Access* 335, 859-864.
[35] Beatson et al. (2006). *Trends Microbiol* 14, 151-155.
[36] She et al. (2015) *Anal. Chem.,* 87 (8), pp 4218-4224
[37] Song et al. (2017) *Sci Rep.* 7: 40878
[38] Kelly et al. (2015) *Nature Protocols* 10, 845-858
[39] Pettersen E F et al. (2004), *J Comput Chem* 25(13): 1605-12.
[40] Sun et al. (2013) *J Bacteriol.* 195(11):2550-61.
[41] Attmannspacher et al. (2008) *Mol Microbiol* 68, 328-341.
[42] Okino et al. (1989) *J Bacteriol* 171, 2075-82.
[43] Darnton and Berg (2008) *J Bacteriol* 190, 8223-4.
[44] Kawai and Akira (2007) *Trends in Molecular Medicine* 13, 11, 460-469
[45] Gewirtz et at (2011) *Journal of Immunology* 167, 1882-1885
[46] Uematsu, S. et al. (2006 Nature Immunology 7, 868-874
[47] Steiner (2007). *Infection and Immunity* 75, 545-552
[48] Cai et al. (2011) *Cancer Res.* 71(7): 2466-2475
[49] Zheng et al. (2017) *Sci Transl Med.* 8; 9(376).
[50] WO2017/085520
[51] Rhee et al (2008) *Gastroenterology,* 135, 2, 518-528.e3
[52] Melo et al. (2015) *Immunology and Cell Biology* 93, 86-98
[53] Cai et al. (2011) *Cancer Res.* 71(7): 2466-2475
[54] Bohnhorst et al. (2006) *Leukemia,* 20, 1138-1144
[55] Okamoto et al. (2009) *British Journal of Haematology,* 147, 582-590
[56] Rakoff-Nahoum et al (2009) *Nat Rev Cancer* 9: 57-63.
[57] Leigh et al. (2013) *PLOSone* 9, 1, e85587
[58] Brackett et al. (2016) *PNAS* E874-E883
[59] Sfondrini et al. (2006) *J Immunol* 176 (11) 6624-6630
[60] Haabeth et al. (2012) *Oncolmmunology* 1(1):1146-1152.

[61] Lejeune et al. (2006) *Cancer Immun.* 6:6
[62] Pace et al. (1983) *PNAS.* 80:8782-6.
[63] Sgadari et al. (1996) *PNAS.* 93:13791-6.
[64] Arenberg et al. (1996) *J Exp. Med.* 184:981-92.
[65] Sgadari et al. (1997) *Blood.* 89:2635-43.
[66] Vijay-Kumar et al. (2008) *J Immunol;* 180:8280-8285
[67] Toshkov et al. (2017) *Radiat Res.* 187(5): 570-580
[68] Porte et al. (2015) *Antimicrob. Agents Chemother.* 59,10 6064-6072
[69] Bloch et al. (2016) *Eur Cytokine Netw.;* 27(3):63-67
[70] Weinberger (2018) *Curr Opin Pharmacol,* 41, 34-41.
[71] Lim (2015) *Aging Cell* 14, 907-915
[72] Mohanty et al. (2015) *J Infect Dis,* 211(7) 1174-1184.
[73] Fernandez-Ruiz et al., (2015) *Vaccine* 2015 33(51)
[74] Morel et al., (2011) *Vaccine,* 29(13) 2461-2473.
[75] Leal et al., (2001) *Immunol* 103(3) 375-381
[76] Knudsen et al. (2016), *Sci Reps,* 6 (19570).
[77] Su et al., (2008) *Vaccine* 26(40), 5111-22
[78] Li et al, (2007) *J Immunol,* 178(8), 5271-5276
[79] Coffman et al., (2012) *Immunity* 33(4) 492-503
[80] Olafsdottir et al., *Vaccine* 33(40) 5302-5307
[81] Didierlaurent et al., *J Immunol* 2014, 193(4) 1920-1930
[82] Park et al., (2002) *J Immunol,* 169(3), 1433-1443
[83] Berthoud et al. (2009) *J Immunol Methods* 340(1) 33-41
[84] Mori et al. (2012), *Eur J Immunol* 42, 2709-2719
[85] Ren and Tones (2009) *Brain Res Rev.;* 60(1):57-64
[86] Martinon et al. (2002) *Mol Cell.;* 10(2):417-26.
[87] Murphy et al. (2003) *J Exp Med.* 2003; 198(12): 1951-1957.
[88] Chan et al. (2006) *J Exp Med.;* 203(12): 2577-2587.
[89] *The Immune Response Basic and Clinical Principles,* 1st Edition (2006)
[90] Gaur and Aggarwal (2003). *Biochem Pharmacol.;* 66(8):1403-8.
[91] Wang and Lin (2008) *Acta Pharmacol Sin.;* 29(11): 1275-1288.
[92] Tanaka et al. (2014) *Cold Spring Harb Perspect Biol.;* 6(10): a016295.
[93] Bettelli et al. (2006) *Nature* 441:235-238
[94] Fraietta, et al. (2018) *Nat Med.* 24(5):563-571
[95] Zhou, et al. (2010) *Blood* 116(14):2484-93.
[96] Glenn and Whartenby (2014) *World J Stem Cells.;* 6(5): 526-539.
[97] Heng et al. (2004) *Cardiovasc Res.* 2004 Apr. 1; 62(1):34-42.
[98] Rashidi et al. (2018) *Biol Blood Marrow Transplant* 24, 1260-1263
[99] Fulop et al (2013) *Crit Rev Oncog.* 2013; 18(6):489-513.
[100] Bektas et al. (2017) *J Leukoc Biol.;* 102(4):977-988.
[101] Fulop et al (2016) *Rev Invest Clin.;* 68(2):84-91.
[102] Fulop et al. (2018) *Front Immunol.;* 8:1960.
[103] WO2006/110603.
[104] Handbook of Pharmaceutical Excipients, 2nd Edition, (1994), Edited by A Wade and P J Weller
[105] Remington's Pharmaceutical Sciences, Mack Publishing Co. (A. R. Gennaro edit. 1985)
[106] US 2016/0067188
[107] Gennaro (2000) *Remington: The Science and Practice of Pharmacy.* 20th edition, ISBN: 0683306472.
[108] *Molecular Biology Techniques: An Intensive Laboratory Course,* (Ream et al., eds., 1998, Academic Press).
[109] *Methods In Enzymology* (S. Colowick and N. Kaplan, eds., Academic Press, Inc.)
[110] *Handbook of Experimental Immunology,* Vols. I-IV (D. M. Weir and C. C. Blackwell, eds, 1986, Blackwell Scientific Publications)
[111] Sambrook et al. (2001) *Molecular Cloning: A Laboratory Manual,* 3rd edition (Cold Spring Harbor Laboratory Press).
[112] *Handbook of Surface and Colloidal Chemistry* (Birdi, K. S. ed., CRC Press, 1997)
[113] Ausubel et al. (eds) (2002) *Short protocols in molecular biology,* 5th edition (Current Protocols).
[114] *PCR (Introduction to Biotechniques Series),* 2nd ed. (Newton & Graham eds., 1997, Springer Verlag)
[115] *Current Protocols in Molecular Biology* (F. M. Ausubel et al., eds., 1987) Supplement 30
[116] *Current Protocols in Molecular Biology* (F. M. Ausubel et al., eds., 1987) Supplement 30
[117] Smith & Waterman (1981) *Adv. Appl. Math.* 2: 482-489.
[118] Law J et al. (1995) *J Bacteriol* 177:7011-7018.
[119] Shepard et al., B. D. & Gilmore, M. S. In Electroporation and efficient transformation of *Enterococcus faecalis* grown in high concentrations of glycine in Methods in molecular biology: Vol 47: Electroporation protocols for microorganisms Vol 47 (ed J. A. Nickoloff) 217-226 (Humana Press Inc., 1995)

The invention claimed is:

1. A pharmaceutical composition that comprises an isolated *Enterococcus* flagellin polypeptide in a unit dose comprising the *Enterococcus* flagellin polypeptide and a pharmaceutically acceptable excipient, diluent, or carrier, wherein the pharmaceutical composition is an enteric formulation, and wherein the *Enterococcus* flagellin polypeptide is from an *Enterococcus gallinarum* strain and comprises an amino acid sequence with at least 98% sequence identity to SEQ ID NO: 1.

2. The pharmaceutical composition of claim 1, wherein the composition comprises a therapeutically effective amount of the flagellin polypeptide sufficient to stimulate an immune response in a subject when administered as a unit dose to the subject.

3. The pharmaceutical composition of claim 1, wherein the *Enterococcus* flagellin polypeptide comprises a polypeptide sequence with at least 99% sequence identity to the polypeptide sequence of SEQ ID NO: 1.

4. The pharmaceutical composition of claim 1, wherein the *Enterococcus* flagellin polypeptide comprises a polypeptide sequence with 100% sequence identity to the polypeptide sequence of SEQ ID NO: 1.

5. The pharmaceutical composition of claim 1, wherein the *Enterococcus* flagellin polypeptide is from the *Enterococcus gallinarum* strain deposited under accession number NCIMB 42488.

6. A pharmaceutical composition that comprises an isolated recombinant *Enterococcus* flagellin polypeptide in a unit dose comprising a therapeutically effective amount of the *Enterococcus* flagellin polypeptide to stimulate an immune response in a subject when administered to the subject and a pharmaceutically acceptable excipient, diluent, or carrier, wherein the pharmaceutical composition is an enteric formulation, and wherein the *Enterococcus* flagellin polypeptide comprises an amino acid sequence with at least 98% sequence identity to SEQ ID NO: 1.

7. The pharmaceutical composition of claim 1, wherein the pharmaceutical composition is a solid composition.

8. The pharmaceutical composition of claim 1, wherein the pharmaceutical composition is formulated as a tablet or a capsule.

9. The pharmaceutical composition of claim 1, wherein the pharmaceutical composition is formulated for delivery to an intestine of the subject.

10. The pharmaceutical composition of claim 1, wherein the pharmaceutical composition comprises a preservative, an antioxidant, or a stabilizer.

11. The pharmaceutical composition of claim 1, wherein the at least 98% sequence identity to SEQ ID NO:1 is determined by a Smith-Waterman homology search algorithm using an affine gap search with a gap open penalty of 12 and a gap extension penalty of 2.

* * * * *

SEQUENCE LISTING

<160> NUMBER OF SEQ ID NOS: 53

<210> SEQ ID NO 1
<211> LENGTH: 360
<212> TYPE: PRT
<213> ORGANISM: Enterococcus gallinarum
<220> FEATURE:
<223> OTHER INFORMATION: Enterococcus gallinarum MRx0518

<400> SEQUENCE: 1

Met Arg Ile Asn Thr Asn Val Ser Ala Leu Asn Thr Tyr Ser Arg Leu
1               5                   10                  15

Thr Ala Ala Asn Ala Ser Lys Ser Asn Ser Leu Ser Lys Leu Ser Ser
            20                  25                  30

Gly Leu Arg Ile Asn Lys Ala Gly Asp Asp Ala Ala Gly Leu Ala Ile
        35                  40                  45

Ser Glu Lys Met Lys Gly Gln Ile Gly Gly Leu Ser Gln Ala Lys Ser

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Asp Ala Lys
130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
210                 215                 220

Thr Ala Ile Asp Thr Ala Ala Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 2
<211> LENGTH: 361
<212> TYPE: PRT
<213> ORGANISM: Enterococcus gallinarum
<220> FEATURE:
<223> OTHER INFORMATION: Enterococcus gallinarum DSM100110

<400> SEQUENCE: 2

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Met Arg Ile Asn Lys Ala Gly Asp Asp Ala Gly Leu Ala Ile
            35                  40                  45

Ser Glu Lys Met Lys Gly Gln Ile Gly Gly Leu Ser Gln Ala Lys Ser
```

```
                50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Thr Asp Asp Arg Glu Ala Ile Ser Lys
                100                 105                 110

Glu Phe Ser Ala Leu Ser Asp Glu Ile Asp Arg Ile Ser Thr Thr Thr
            115                 120                 125

Glu Phe Asn Thr Lys Ser Leu Leu Lys Gly Gly Glu Ser Gly Glu Lys
            130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                165                 170                 175

Lys Leu Glu Glu Ala Lys Asp Ala Glu Ser Glu Ile Ala Lys Lys Val
            180                 185                 190

Glu Thr Ala Phe Leu Asp Ala Ala Asn Ser Asp Lys Tyr Asp Ala Asp
            195                 200                 205

Gly Lys Ile Asp Ala Ser Ala Gly Lys Thr Ala Ala Glu Leu Lys Asp
            210                 215                 220

Ala Ile Glu Asn Ala Ala Asp Asp Thr Ala Lys Ala Ala Ala Gln Lys
225                 230                 235                 240

Thr Tyr Asp Ala Ala Leu Glu Thr Phe Lys Ala Ser Thr Asn Gly Gln
                245                 250                 255

Thr Ala Ile Ala Thr Ala Lys Thr Glu Val Glu Glu Ala Ser Lys Asn
            260                 265                 270

Ser Thr Val Ser Lys Ile Asp Glu Ala Ile Lys Thr Val Ser Ala Gln
            275                 280                 285

Arg Ala Asp Leu Gly Ala Ala Gln Asn Arg Leu Glu His Thr Ile Asn
            290                 295                 300

Asn Leu Gly Thr Thr Gln Glu Asn Leu Ser Glu Ala Asn Ser Arg Ile
305                 310                 315                 320

Arg Asp Val Asp Met Ala Gln Glu Met Met Ser Phe Thr Lys Ser Asn
                325                 330                 335

Ile Leu Ser Gln Ala Ala Thr Ser Met Leu Ala Gln Ala Asn Ser Met
            340                 345                 350

Pro Asn Ser Val Leu Ser Leu Leu Gln
            355                 360

<210> SEQ ID NO 3
<211> LENGTH: 360
<212> TYPE: PRT
<213> ORGANISM: Enterococcus gallinarum
<220> FEATURE:
<223> OTHER INFORMATION: Enterococcus gallinarum MRx0554

<400> SEQUENCE: 3

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Arg Asp Thr Thr
                115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
                180                 185                 190

Ala Val Ala Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
    210                 215                 220

Thr Ala Ile Asp Thr Ala Ala Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 4
<211> LENGTH: 360
<212> TYPE: PRT
<213> ORGANISM: Enterococcus gallinarum
<220> FEATURE:
<223> OTHER INFORMATION: Enterococcus gallinarum MRx0556

<400> SEQUENCE: 4

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Asp Ala Lys
130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
            210                 215                 220

Thr Ala Ile Asp Thr Ala Ala Asp Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 5
<211> LENGTH: 360
<212> TYPE: PRT
<213> ORGANISM: Enterococcus gallinarum
<220> FEATURE:
<223> OTHER INFORMATION: Enterococcus gallinarum MRx1548

<400> SEQUENCE: 5

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Lys Ala Asp Thr Thr Thr Lys Tyr Ala Ala
            195                 200                 205

Asp Gly Lys Val Asp Ala Ala Gly Lys Thr Val Ala Asp Leu Gln
            210                 215                 220

Thr Ala Ile Asp Thr Ala Ala Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 6
<211> LENGTH: 360
<212> TYPE: PRT
<213> ORGANISM: Enterococcus gallinarum
<220> FEATURE:
<223> OTHER INFORMATION: Enterococcus gallinarum MRx1650

<400> SEQUENCE: 6

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
              50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Arg Asp Thr Thr
                115                 120                 125

Glu Phe Asn Thr Lys Ser Leu Leu Thr Gly Glu Gly Asp Asp Ala Lys
                130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Ala Lys Asp Lys
                180                 185                 190

Ala Val Ala Ala Ala Phe Lys Ala Asp Thr Thr Thr Lys Tyr Ala Ala
                195                 200                 205

Asp Gly Lys Val Asp Ala Ala Ala Gly Lys Thr Val Ala Asp Leu Gln
                210                 215                 220

Thr Ala Ile Asp Thr Ala Ala Asp Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
                260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
                290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
                340                 345                 350

Ser Val Leu Ser Leu Leu Gln Gly
                355                 360

<210> SEQ ID NO 7
<211> LENGTH: 360
<212> TYPE: PRT
<213> ORGANISM: Enterococcus gallinarum
<220> FEATURE:
<223> OTHER INFORMATION: Enterococcus gallinarum MRx1763

<400> SEQUENCE: 7

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Asp Ala Lys
130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
            210                 215                 220

Thr Ala Ile Asp Thr Ala Ala Asp Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
                340                 345                 350

Ser Val Leu Ser Leu Leu Gln Gly
            355                 360

<210> SEQ ID NO 8
<211> LENGTH: 360
<212> TYPE: PRT
<213> ORGANISM: Enterococcus gallinarum
<220> FEATURE:
<223> OTHER INFORMATION: Enterococcus gallinarum MRx1766

<400> SEQUENCE: 8

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
    210                 215                 220

Thr Ala Ile Asp Thr Ala Ala Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 9
<211> LENGTH: 360
<212> TYPE: PRT
<213> ORGANISM: Enterococcus gallinarum
<220> FEATURE:
<223> OTHER INFORMATION: Enterococcus gallinarum MRx1775

<400> SEQUENCE: 9

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
                50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
        115                 120                 125

Glu Phe Asn Thr Lys Ser Leu Leu Thr Gly Glu Gly Asp Asp Ala Lys
    130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Lys Ala Asp Thr Thr Thr Lys Tyr Ala Ala
        195                 200                 205

Asp Gly Lys Val Asp Ala Ala Gly Lys Thr Val Ala Asp Leu Gln
    210                 215                 220

Thr Ala Ile Asp Thr Ala Ala Asp Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
        275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 10
<211> LENGTH: 360
<212> TYPE: PRT
<213> ORGANISM: Enterococcus gallinarum
<220> FEATURE:
<223> OTHER INFORMATION: Enterococcus gallinarum MRx1886

<400> SEQUENCE: 10

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
210                 215                 220

Thr Ala Ile Asp Thr Ala Ala Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 11
<211> LENGTH: 360
<212> TYPE: PRT
<213> ORGANISM: Enterococcus gallinarum
<220> FEATURE:
<223> OTHER INFORMATION: Enterococcus gallinarum 2A8

<400> SEQUENCE: 11

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Val Ala Lys
            130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
            210                 215                 220

Thr Ala Ile Asp Thr Ala Ala Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 12
<211> LENGTH: 360
<212> TYPE: PRT
<213> ORGANISM: Enterococcus gallinarum
<220> FEATURE:
<223> OTHER INFORMATION: Enterococcus gallinarum 9402

<400> SEQUENCE: 12

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Arg Asp Thr Thr
                115                 120                 125

Glu Phe Asn Thr Lys Ser Leu Leu Thr Gly Glu Gly Asn Val Ala Lys
            130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
                180                 185                 190

Ala Val Ala Ala Ala Phe Lys Ala Asp Thr Thr Lys Tyr Ala Ala
            195                 200                 205

Asp Gly Lys Val Asp Ala Ala Gly Lys Thr Val Ala Asp Leu Gln
    210                 215                 220

Thr Ala Ile Asp Thr Ala Ala Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 13
<211> LENGTH: 360
<212> TYPE: PRT
<213> ORGANISM: Enterococcus gallinarum
<220> FEATURE:
<223> OTHER INFORMATION: Enterococcus gallinarum A6981

<400> SEQUENCE: 13

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asn Thr Thr
            115                 120                 125

Glu Phe Asn Thr Lys Ser Leu Leu Thr Gly Glu Gly Asn Asp Ala Lys
        130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Val Leu Asp Val Lys Gly Leu Asp
                165                 170                 175

Leu Thr Gln Ala Phe Ala Thr Ser Asp Ile Ala Ala Lys Asp Lys
            180                 185                 190

Ala Val Ala Ala Ala Phe Ile Ala Asp Thr Thr Lys Tyr Ala Ala
        195                 200                 205

Asp Gly Lys Val Asp Ala Ala Gly Lys Thr Ala Ala Asp Leu Gln
    210                 215                 220

Thr Ala Ile Gly Thr Ala Ala Asp Asp Ala Ala Lys Ala Thr Ala Gln
225                 230                 235                 240

Lys Thr Tyr Asp Asp Ala Leu Ala Thr Phe Thr Ala Ser Asp Lys Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
        290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 14
<211> LENGTH: 360
<212> TYPE: PRT
<213> ORGANISM: Enterococcus gallinarum
<220> FEATURE:
<223> OTHER INFORMATION: Enterococcus gallinarum MRx1649

<400> SEQUENCE: 14

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Arg Asn Thr Thr
                115                 120                 125

Glu Phe Asn Thr Lys Ser Leu Leu Thr Gly Glu Gly Asn Asp Ala Lys
            130                 135                 140

Ser Phe Thr Phe Gln Ile Gly Ala Asn Ala Asn Gln Thr Met Ser Val
145                 150                 155                 160

Ser Ile Lys Asn Met Ser Ser Thr Val Leu Asp Val Lys Gly Leu Asp
                165                 170                 175

Leu Thr Gln Ala Phe Ser Thr Ser Glu Ile Ala Ala Lys Asp Lys
                180                 185                 190

Ala Val Ala Ala Ala Phe Ile Ala Asp Thr Thr Lys Tyr Ala Ala
            195                 200                 205

Asp Gly Lys Val Asp Ala Ala Gly Lys Thr Ala Ala Asp Leu Gln
            210                 215                 220

Thr Ala Ile Gly Thr Ala Ala Asp Asp Ala Ala Lys Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
                275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 15
<211> LENGTH: 360
<212> TYPE: PRT
<213> ORGANISM: Enterococcus gallinarum
<220> FEATURE:
<223> OTHER INFORMATION: Enterococcus gallinarum EG2

<400> SEQUENCE: 15

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Arg Asn Asn Thr
            115                 120                 125

Glu Phe Asn Thr Lys Ser Leu Leu Thr Gly Glu Gly Asn Asp Ala Lys
        130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Val Leu Asp Val Lys Gly Leu Asp
                165                 170                 175

Leu Thr Gln Ala Phe Ser Thr Ser Glu Ile Ala Ala Lys Asp Lys
            180                 185                 190

Ala Val Ala Ala Phe Ile Ala Asp Thr Thr Lys Tyr Ala Ala
        195                 200                 205

Asp Gly Lys Val Asp Ala Ala Gly Lys Thr Ala Ala Asp Leu Gln
    210                 215                 220

Thr Ala Ile Gly Thr Ala Ala Asp Asp Ala Ala Glu Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
        275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 16
<211> LENGTH: 360
<212> TYPE: PRT
<213> ORGANISM: Enterococcus gallinarum
<220> FEATURE:
<223> OTHER INFORMATION: Enterococcus gallinarum SKF1

<400> SEQUENCE: 16

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asn Asn Thr
        115                 120                 125

Glu Phe Asn Thr Lys Ser Leu Leu Thr Gly Glu Gly Asn Asp Ala Lys
    130                 135                 140

Ser Phe Thr Phe Gln Ile Gly Ala Asn Ala Asn Gln Thr Met Ser Val
145                 150                 155                 160

Ser Ile Lys Asn Met Ser Ser Thr Val Leu Asp Val Lys Gly Leu Asp
                165                 170                 175

Leu Thr Gln Ala Phe Ser Thr Ser Glu Ile Ala Ala Lys Asp Lys
            180                 185                 190

Ala Val Ala Ala Ala Phe Ile Ala Asp Thr Thr Lys Tyr Ala Ala
        195                 200                 205

Asp Gly Lys Val Asp Ala Ala Gly Lys Thr Ala Ala Asp Leu Gln
    210                 215                 220

Thr Ala Ile Gly Thr Ala Ala Asp Asp Ala Ala Glu Ala Thr Ala Gln
225                 230                 235                 240

Lys Thr Tyr Asp Asp Ala Leu Ala Thr Phe Thr Ala Ser Asp Glu Gly
                245                 250                 255

Lys Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
        275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 17
<211> LENGTH: 360
<212> TYPE: PRT
<213> ORGANISM: Enterococcus casseliflavus
<220> FEATURE:
<223> OTHER INFORMATION: Enterococcus casseliflavus DSM 7370

<400> SEQUENCE: 17

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
            245                 250                 255

Asp Glu Gly Lys Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 18
<211> LENGTH: 360
<212> TYPE: PRT
<213> ORGANISM: Enterococcus casseliflavus
<220> FEATURE:
<223> OTHER INFORMATION: Enterococcus casseliflavus 1a6A

<400> SEQUENCE: 18

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
            210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 19
<211> LENGTH: 360
<212> TYPE: PRT
<213> ORGANISM: Enterococcus casseliflavus
<220> FEATURE:
<223> OTHER INFORMATION: Enterococcus casseliflavus 3h10B

<400> SEQUENCE: 19

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Ala Gly Lys Thr Val Ala
            210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 20
<211> LENGTH: 360
<212> TYPE: PRT
<213> ORGANISM: Enterococcus casseliflavus
<220> FEATURE:
<223> OTHER INFORMATION: Enterococcus casseliflavus 14-MB-W-14

<400> SEQUENCE: 20

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
            210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 21
<211> LENGTH: 360
<212> TYPE: PRT
<213> ORGANISM: Enterococcus casseliflavus
<220> FEATURE:
<223> OTHER INFORMATION: Enterococcus casseliflavus ATCC12755

<400> SEQUENCE: 21

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
            210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 22
<211> LENGTH: 360
<212> TYPE: PRT
<213> ORGANISM: Enterococcus casseliflavus
<220> FEATURE:
<223> OTHER INFORMATION: Enterococcus casseliflavus DSM4841

<400> SEQUENCE: 22

Met Arg Ile Asn Thr Asn Val Ser Ala Leu Asn Thr Tyr Ser Arg Leu
  1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                     85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Ser Asn Thr Thr
                115                 120                 125

Glu Phe Asn Thr Lys Ser Leu Leu Thr Gly Glu Gly Asp Asp Ala Lys
130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
                180                 185                 190

Lys Asp Lys Ala Val Ala Thr Ala Phe Lys Ala Asp Ala Thr Thr Lys
                195                 200                 205

Tyr Ala Ala Asp Gly Thr Val Asp Ala Ala Gly Lys Thr Val Ala
210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
                260                 265                 270

Ile Thr Lys Ile Asp Glu Ala Ile Lys Ala Val Ser Ala Gln Arg Ala
                275                 280                 285

Asp Leu Gly Ala Ala Gln Asn Arg Leu Glu His Thr Ile Asn Asn Leu
                290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
                340                 345                 350

Ser Val Leu Ser Leu Leu Gln Gly
            355                 360

<210> SEQ ID NO 23
<211> LENGTH: 360
<212> TYPE: PRT
<213> ORGANISM: Enterococcus casseliflavus
<220> FEATURE:
<223> OTHER INFORMATION: Enterococcus casseliflavus DSM20680

<400> SEQUENCE: 23

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
             100                 105                 110

Glu Tyr Thr Ala Leu Ser Asp Glu Ile Asp Arg Ile Ser Asn Thr Thr
             115                 120                 125

Glu Phe Asn Thr Lys Ser Leu Leu Thr Gly Glu Gly Asp Asp Ala Lys
         130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                 165                 170                 175

Leu Thr Gln Ala Ile Asp Thr Ser Asp Ala Lys Ala Val Ala Ala Ala
             180                 185                 190

Lys Asp Lys Ala Val Ala Thr Ala Phe Lys Ala Asp Ala Thr Thr Lys
         195                 200                 205

Tyr Ala Ala Asp Gly Thr Val Asp Ala Ala Gly Lys Thr Val Ala
210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                 245                 250                 255

Asp Glu Gly Lys Ala Ala Ala Ala Thr Val Ser Val Glu Asn Asn Pro
             260                 265                 270

Ile Thr Lys Ile Asp Glu Ala Ile Lys Ala Val Ser Ala Gln Arg Ala
         275                 280                 285

Asp Leu Gly Ala Ala Gln Asn Arg Leu Glu His Thr Ile Asn Asn Leu
         290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                 325                 330                 335

Ser Gln Ala Ala Thr Ser Met Leu Ala Gln Ala Asn Ser Met Pro Asn
             340                 345                 350

Ser Val Leu Ser Leu Leu Gln Gly
         355                 360

<210> SEQ ID NO 24
<211> LENGTH: 360
<212> TYPE: PRT
<213> ORGANISM: Enterococcus casseliflavus
<220> FEATURE:
<223> OTHER INFORMATION: Enterococcus casseliflavus EC10

<400> SEQUENCE: 24

Met Arg Ile Asn Thr Asn Val Ser Ala Leu Asn Thr Tyr Ser Arg Leu
1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 25
<211> LENGTH: 360
<212> TYPE: PRT
<213> ORGANISM: Enterococcus casseliflavus
<220> FEATURE:
<223> OTHER INFORMATION: Enterococcus casseliflavus EC20

<400> SEQUENCE: 25

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
            210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 26
<211> LENGTH: 360
<212> TYPE: PRT
<213> ORGANISM: Enterococcus casseliflavus
<220> FEATURE:
<223> OTHER INFORMATION: Enterococcus casseliflavus EC30

<400> SEQUENCE: 26

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Ser Asn Thr Thr
                115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
                180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
                260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
        290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 27
<211> LENGTH: 360
<212> TYPE: PRT
<213> ORGANISM: Enterococcus casseliflavus
<220> FEATURE:
<223> OTHER INFORMATION: Enterococcus casseliflavus F1129

<400> SEQUENCE: 27

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
                50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Ser Asn Thr Thr
                115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
        195                 200                 205

Tyr Ala Ala Asp Gly Thr Val Asp Ala Ala Gly Lys Thr Val Ala
    210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
        275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 28
<211> LENGTH: 360
<212> TYPE: PRT
<213> ORGANISM: Enterococcus casseliflavus
<220> FEATURE:
<223> OTHER INFORMATION: Enterococcus casseliflavus F1129F 46

<400> SEQUENCE: 28

Met Arg Ile Asn Thr Asn Val Ser Ala Leu Asn Thr Tyr Ser Arg Leu
1               5                   10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
    130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
    195                 200                 205

Tyr Ala Ala Asp Gly Thr Val Asp Ala Ala Gly Lys Thr Val Ala
210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 29
<211> LENGTH: 360
<212> TYPE: PRT
<213> ORGANISM: Enterococcus casseliflavus
<220> FEATURE:
<223> OTHER INFORMATION: Enterococcus casseliflavus NBRC 100478

<400> SEQUENCE: 29

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Ala Gly Lys Thr Val Ala
            210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 30
<211> LENGTH: 360
<212> TYPE: PRT
<213> ORGANISM: Enterococcus casseliflavus
<220> FEATURE:
<223> OTHER INFORMATION: Enterococcus casseliflavus PAVET15

<400> SEQUENCE: 30

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Ser Asn Thr Thr
            115                 120                 125

Glu Phe Asn Thr Lys Ser Leu Leu Thr Gly Glu Gly Asp Asp Ala Lys
            130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
            180                 185                 190

Lys Asp Lys Ala Val Ala Thr Ala Phe Lys Ala Asp Ala Thr Thr Lys
            195                 200                 205

Tyr Ala Ala Asp Gly Thr Val Asp Ala Ala Gly Lys Thr Val Ala
            210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
            260                 265                 270

Ile Thr Lys Ile Asp Glu Ala Ile Lys Ala Val Ser Ala Gln Arg Ala
            275                 280                 285

Asp Leu Gly Ala Ala Gln Asn Arg Leu Glu His Thr Ile Asn Asn Leu
            290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
            355                 360

<210> SEQ ID NO 31
<211> LENGTH: 360
<212> TYPE: PRT
<213> ORGANISM: Enterococcus casseliflavus
<220> FEATURE:
<223> OTHER INFORMATION: Enterococcus casseliflavus NLAE-zl-G268

<400> SEQUENCE: 31

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
             100                 105                 110

Glu Tyr Thr Ala Leu Ser Asp Glu Ile Asp Arg Ile Ser Asn Thr Thr
             115                 120                 125

Glu Phe Asn Thr Lys Ser Leu Leu Thr Gly Glu Gly Asp Asp Ala Lys
             130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                 165                 170                 175

Leu Thr Gln Ala Ile Asp Thr Ser Asp Ala Lys Ala Val Ala Ala Ala
             180                 185                 190

Lys Asp Lys Ala Val Ala Thr Ala Phe Lys Ala Asp Ala Thr Thr Lys
             195                 200                 205

Tyr Ala Ala Asp Gly Thr Val Asp Ala Ala Gly Lys Thr Val Ala
             210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                 245                 250                 255

Asp Glu Gly Lys Ala Ala Ala Ala Thr Val Ser Val Glu Asn Asn Pro
             260                 265                 270

Ile Thr Lys Ile Asp Glu Ala Ile Lys Ala Val Ser Ala Gln Arg Ala
             275                 280                 285

Asp Leu Gly Ala Ala Gln Asn Arg Leu Glu His Thr Ile Asn Asn Leu
             290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                 325                 330                 335

Ser Gln Ala Ala Thr Ser Met Leu Ala Gln Ala Asn Ser Met Pro Asn
             340                 345                 350

Ser Val Leu Ser Leu Leu Gln Gly
             355                 360

<210> SEQ ID NO 32
<211> LENGTH: 360
<212> TYPE: PRT
<213> ORGANISM: Enterococcus casseliflavus
<220> FEATURE:
<223> OTHER INFORMATION: Enterococcus casseliflavus NLAE-zl-C414

<400> SEQUENCE: 32

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asp Asp Arg Ser Ala Ile Asn Lys
             100                 105                 110

Glu Tyr Thr Ala Leu Ser Asp Glu Ile Asp Arg Ile Ser Asn Thr Thr
             115                 120                 125

Glu Phe Asn Thr Lys Ser Leu Leu Thr Gly Glu Gly Asp Asp Ala Lys
             130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                 165                 170                 175

Leu Thr Gln Ala Ile Asp Thr Ser Asp Ala Lys Ala Val Ala Ala Ala
             180                 185                 190

Lys Asp Lys Ala Val Ala Thr Ala Phe Lys Ala Asp Ala Thr Thr Lys
             195                 200                 205

Tyr Ala Ala Asp Gly Thr Val Asp Ala Ala Gly Lys Thr Val Ala
210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                 245                 250                 255

Asp Glu Gly Lys Ala Ala Ala Thr Val Ser Val Glu Asn Asn Pro
             260                 265                 270

Ile Thr Lys Ile Asp Glu Ala Ile Lys Ala Val Ser Ala Gln Arg Ala
             275                 280                 285

Asp Leu Gly Ala Ala Gln Asn Arg Leu Glu His Thr Ile Asn Asn Leu
             290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                 325                 330                 335

Ser Gln Ala Ala Thr Ser Met Leu Ala Gln Ala Asn Ser Met Pro Asn
                 340                 345                 350

Ser Val Leu Ser Leu Leu Gln Gly
             355                 360

<210> SEQ ID NO 33
<211> LENGTH: 360
<212> TYPE: PRT
<213> ORGANISM: Enterococcus gallinarum
<220> FEATURE:
<223> OTHER INFORMATION: Enterococcus gallinarum FDAARGOS-163

<400> SEQUENCE: 33

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Leu Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
                    50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                     85                  90                  95

Ser Ser Asn Gly Thr Leu Ser Asp Asp Arg Ser Ala Ile Asn Lys
                100                 105                 110

Glu Tyr Thr Ala Leu Ser Asp Glu Ile Asp Arg Ile Ser Asn Thr Thr
                115                 120                 125

Glu Phe Asn Thr Lys Ser Leu Leu Thr Gly Glu Gly Asp Asp Ala Lys
                130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Gly Leu Asp
                165                 170                 175

Leu Thr Gln Ala Ile Asp Thr Ser Asp Ala Lys Ala Val Ala Ala Ala
                180                 185                 190

Lys Asp Lys Ala Val Ala Thr Ala Phe Glu Ala Asp Ala Thr Thr Lys
                195                 200                 205

Tyr Ala Ala Asp Gly Thr Val Asp Ala Ala Ala Gly Lys Thr Val Ala
                210                 215                 220

Glu Leu Gln Thr Ala Ile Asp Thr Ala Ala Asp Asp Thr Ala Lys Ala
225                 230                 235                 240

Thr Ala Gln Lys Thr Tyr Asp Asp Ala Leu Ala Thr Phe Thr Ala Ser
                245                 250                 255

Asp Glu Gly Lys Ala Ala Ala Ala Thr Val Ser Val Glu Asn Asn Pro
                260                 265                 270

Ile Thr Lys Ile Asp Glu Ala Ile Lys Ala Val Ser Ala Gln Arg Ala
                275                 280                 285

Asp Leu Gly Ala Ala Gln Asn Arg Leu Glu His Thr Ile Asn Asn Leu
                290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
                340                 345                 350

Ser Val Leu Ser Leu Leu Gln Gly
                355                 360

<210> SEQ ID NO 34
<211> LENGTH: 360
<212> TYPE: PRT
<213> ORGANISM: Enterococcus casseliflavus
<220> FEATURE:
<223> OTHER INFORMATION: Enterococcus casseliflavus MRx0858

<400> SEQUENCE: 34

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
                35                  40                  45

Ser Glu Lys Met Lys Gly Gln Ile Gly Gly Leu Ser Gln Ala Lys Ser
```

```
                    50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                     85                  90                  95

Ser Ser Asn Gly Thr Leu Ser Asn Asp Asp Arg Asp Ala Ile Lys Lys
                100                 105                 110

Glu Tyr Thr Ala Leu Ser Asp Glu Ile Asp Arg Ile Arg Asp Thr Thr
            115                 120                 125

Glu Phe Asn Thr Lys Ser Leu Leu Thr Gly Glu Gly Asp Asp Ala Lys
        130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Ala Leu Lys Val Lys Val Leu Asp
                165                 170                 175

Leu Thr Gln Ala Phe Asp Thr Ser Asp Ala Lys Ala Val Ala Ala Ala
            180                 185                 190

Lys Asp Lys Ala Val Ala Thr Ala Phe Glu Ala Asp Thr Thr Thr Lys
        195                 200                 205

Tyr Ala Leu Asp Gly Thr Val Gly Ala Ala Asp Gly Lys Thr Ala Val
    210                 215                 220

Glu Leu Lys Thr Ala Phe Lys Ser Glu Thr Asp Val Thr Arg Lys Ala
225                 230                 235                 240

Glu Ala Lys Lys Ala Tyr Asp Asn Ala Leu Ala Thr Phe Thr Ala Ser
                245                 250                 255

Asp Glu Gly Lys Ala Ala Glu Ala Thr Val Ser Phe Glu Asn Asn Pro
            260                 265                 270

Ile Thr Lys Ile Asp Glu Ala Ile Lys Ala Val Ser Ala Gln Arg Ala
        275                 280                 285

Asp Leu Gly Ala Ala Gln Asn Arg Leu Glu His Thr Ile Asn Asn Leu
    290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
            340                 345                 350

Ser Val Leu Ser Leu Leu Gln Gly
        355                 360

<210> SEQ ID NO 35
<211> LENGTH: 361
<212> TYPE: PRT
<213> ORGANISM: Enterococcus casseliflavus
<220> FEATURE:
<223> OTHER INFORMATION: Enterococcus casseliflavus DSM25781

<400> SEQUENCE: 35

Met Arg Ile Asn Thr Asn Val Ser Ala Leu Asn Thr Tyr Ser Arg Leu
1               5                   10                  15

Thr Ala Ala Asn Ala Ser Lys Ser Asn Ser Leu Ser Lys Leu Ser Ser
                20                  25                  30

Gly Leu Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Asn Asp Arg Asp Ala Ile Lys Lys
             100                 105                 110

Glu Tyr Thr Ala Leu Ser Asp Glu Ile Asp Arg Ile Ser Asn Thr Thr
             115                 120                 125

Glu Phe Asn Thr Lys Lys Leu Leu Thr Gly Glu Gly Asp Asp Ala Lys
         130                 135                 140

Ser Phe Thr Phe Gln Ile Gly Ala Asn Ala Asn Gln Thr Met Ser Val
145                 150                 155                 160

Ser Ile Asn Asn Met Ser Ser Ser Val Leu Lys Val Lys Gly Leu Asp
                 165                 170                 175

Leu Thr Gln Ala Phe Asp Thr Ser Asp Val Lys Ala Val Ala Ala Ala
             180                 185                 190

Lys Asp Lys Ala Val Ala Thr Ala Phe Glu Ala Asp Thr Thr Thr Lys
         195                 200                 205

Tyr Ala Glu Asp Gly Thr Val Asp Ala Thr Asp Gly Lys Thr Val Phe
210                 215                 220

Glu Leu Lys Lys Ala Met Glu Ser Glu Lys Asp Ala Thr Glu Lys Ala
225                 230                 235                 240

Lys Ala Lys Glu Thr Tyr Asp Lys Ala Leu Ala Ile Phe Thr Asp Ser
                 245                 250                 255

Asp Glu Gly Asn Ala Ala Ala Ala Thr Val Ser Gly Asp Asn Asn
             260                 265                 270

Pro Ile Thr Lys Ile Asp Glu Ala Ile Lys Val Val Ser Ala Gln Arg
         275                 280                 285

Ala Asp Leu Gly Ala Ala Gln Asn Arg Leu Glu His Thr Ile Asn Asn
         290                 295                 300

Leu Gly Thr Thr Gln Glu Asn Leu Ser Glu Ala Asn Ser Arg Ile Arg
305                 310                 315                 320

Asp Val Asp Met Ala Gln Glu Met Met Ser Phe Thr Lys Ser Asn Ile
                 325                 330                 335

Leu Ser Gln Ala Ala Thr Ser Met Leu Ala Gln Ala Asn Ser Met Pro
             340                 345                 350

Asn Ser Val Leu Ser Leu Leu Gln Gly
         355                 360

<210> SEQ ID NO 36
<211> LENGTH: 361
<212> TYPE: PRT
<213> ORGANISM: Enterococcus gallinarum
<220> FEATURE:
<223> OTHER INFORMATION: Enterococcus gallinarum DSM28564

<400> SEQUENCE: 36

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Met Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Thr Asp Asp Arg Glu Ala Ile Ser Lys
                100                 105                 110

Glu Phe Ser Ala Leu Ser Asp Glu Ile Asp Arg Ile Ser Thr Thr Thr
            115                 120                 125

Glu Phe Asn Thr Lys Ser Leu Leu Lys Gly Gly Glu Ser Gly Glu Lys
            130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                165                 170                 175

Lys Leu Glu Glu Ala Lys Asp Ala Glu Ser Glu Ile Ala Lys Lys Val
            180                 185                 190

Glu Thr Ala Phe Leu Asp Ala Ala Asn Ser Asp Lys Tyr Asp Ala Asp
            195                 200                 205

Gly Lys Ile Asp Ala Ser Ala Gly Lys Thr Ala Ala Glu Leu Lys Asp
            210                 215                 220

Ala Ile Glu Asn Ala Ala Asp Asp Thr Ala Lys Ala Ala Ala Gln Lys
225                 230                 235                 240

Thr Tyr Asp Ala Ala Leu Glu Thr Phe Lys Ala Ser Thr Asn Gly Gln
                245                 250                 255

Thr Ala Ile Ala Thr Ala Lys Thr Glu Val Glu Glu Ala Ser Lys Asn
                260                 265                 270

Ser Thr Val Ser Lys Ile Asp Glu Ala Ile Lys Thr Val Ser Ala Gln
                275                 280                 285

Arg Ala Asp Leu Gly Ala Ala Gln Asn Arg Leu Glu His Thr Ile Asn
            290                 295                 300

Asn Leu Gly Thr Thr Gln Glu Asn Leu Ser Glu Ala Asn Ser Arg Ile
305                 310                 315                 320

Arg Asp Val Asp Met Ala Gln Glu Met Met Ser Phe Thr Lys Ser Asn
                325                 330                 335

Ile Leu Ser Gln Ala Ala Thr Ser Met Leu Ala Gln Ala Asn Ser Met
            340                 345                 350

Pro Asn Ser Val Leu Ser Leu Leu Gln
            355                 360

<210> SEQ ID NO 37
<211> LENGTH: 361
<212> TYPE: PRT
<213> ORGANISM: Enterococcus gallinarum
<220> FEATURE:
<223> OTHER INFORMATION: Enterococcus gallinarum DSM28565

<400> SEQUENCE: 37

Met Arg Ile Asn Thr Asn Val Ser Ala Leu Asn Thr Tyr Ser Arg Leu
  1               5                  10                  15

Thr Ala Ala Asn Ala Ser Lys Ser Asn Ser Leu Ser Lys Leu Ser Ser
                 20                  25                  30

Gly Met Arg Ile Asn Lys Ala Gly Asp Asp Ala Ala Gly Leu Ala Ile
             35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Thr Asp Asp Arg Glu Ala Ile Ser Lys
                100                 105                 110

Glu Phe Ser Ala Leu Ser Asp Glu Ile Asp Arg Ile Ser Thr Thr Thr
            115                 120                 125

Glu Phe Asn Thr Lys Ser Leu Leu Lys Gly Gly Glu Ser Gly Glu Lys
            130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                165                 170                 175

Lys Leu Glu Glu Ala Lys Asp Ala Glu Ser Glu Ile Ala Lys Lys Val
            180                 185                 190

Glu Thr Ala Phe Leu Asp Ala Ala Asn Ser Asp Lys Tyr Asp Ala Asp
            195                 200                 205

Gly Lys Ile Asp Ala Ser Ala Gly Lys Thr Ala Ala Glu Leu Lys Asp
            210                 215                 220

Ala Ile Glu Asn Ala Ala Asp Thr Ala Lys Ala Ala Ala Gln Lys
225                 230                 235                 240

Thr Tyr Asp Ala Ala Leu Glu Thr Phe Lys Ala Ser Thr Asn Gly Gln
                245                 250                 255

Thr Ala Ile Ala Thr Ala Lys Thr Glu Val Glu Ala Ser Lys Asn
                260                 265                 270

Ser Thr Val Ser Lys Ile Asp Glu Ala Ile Lys Thr Val Ser Ala Gln
            275                 280                 285

Arg Ala Asp Leu Gly Ala Ala Gln Asn Arg Leu Glu His Thr Ile Asn
290                 295                 300

Asn Leu Gly Thr Thr Gln Glu Asn Leu Ser Glu Ala Asn Ser Arg Ile
305                 310                 315                 320

Arg Asp Val Asp Met Ala Gln Glu Met Met Ser Phe Thr Lys Ser Asn
                325                 330                 335

Ile Leu Ser Gln Ala Ala Thr Ser Met Leu Ala Gln Ala Asn Ser Met
            340                 345                 350

Pro Asn Ser Val Leu Ser Leu Leu Gln
            355                 360

<210> SEQ ID NO 38
<211> LENGTH: 358
<212> TYPE: PRT
<213> ORGANISM: Enterococcus gallinarum
<220> FEATURE:
<223> OTHER INFORMATION: Enterococcus gallinarum F1213F 228

<400> SEQUENCE: 38

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Met Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
            50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Thr Asp Asp Arg Glu Ala Ile Ser Lys
                100                 105                 110

Glu Phe Ser Ala Leu Ser Asp Glu Ile Asp Arg Ile Ser Thr Thr Thr
            115                 120                 125

Glu Phe Asn Thr Lys Ser Leu Leu Lys Gly Gly Glu Ser Gly Glu Lys
        130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                165                 170                 175

Lys Leu Glu Glu Ala Lys Asp Ala Glu Ser Glu Ile Ala Lys Lys Val
            180                 185                 190

Glu Thr Ala Phe Leu Ala Gly Thr Glu Thr Tyr Asp Ala Asp Gly Lys
        195                 200                 205

Ile Asp Ala Ser Gly Thr Lys Ala Ser Asp Leu Gln Thr Ala Ile Ala
210                 215                 220

Asn Ala Thr Asp Thr Ala Lys Ala Ala Gln Lys Thr Tyr Asp
225                 230                 235                 240

Ala Ala Leu Glu Ser Phe Lys Ala Ser Ala Asn Gly Gln Thr Ala Ile
                245                 250                 255

Ala Thr Ala Lys Thr Glu Val Glu Asp Ala Lys Asn Ser Thr Val
            260                 265                 270

Ser Lys Ile Asp Glu Ala Ile Lys Thr Val Ser Ala Gln Arg Ala Asp
        275                 280                 285

Leu Gly Ala Ala Gln Asn Arg Leu Glu His Thr Ile Asn Asn Leu Gly
    290                 295                 300

Thr Thr Gln Glu Asn Leu Ser Glu Ala Asn Ser Arg Ile Arg Asp Val
305                 310                 315                 320

Asp Met Ala Gln Glu Met Met Ser Phe Thr Lys Ser Asn Ile Leu Ser
                325                 330                 335

Gln Ala Ala Thr Ser Met Leu Gln Ala Asn Ser Met Pro Asn Ser
            340                 345                 350

Val Leu Ser Leu Leu Gln
        355

<210> SEQ ID NO 39
<211> LENGTH: 352
<212> TYPE: PRT
<213> ORGANISM: Enterococcus gallinarum
<220> FEATURE:
<223> OTHER INFORMATION: Enterococcus gallinarum DSM20718

<400> SEQUENCE: 39

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                20                  25                  30

Gly Met Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
```

```
                50                  55                  60
Asn Ala Gln Asp Gly Ile Ser Leu Ile Gln Thr Ala Glu Gly Ala Leu
 65                  70                  75                  80

Asn Glu Thr His Ser Ile Leu Gly Arg Met Arg Asp Leu Ala Val Gln
                 85                  90                  95

Ser Ser Asn Gly Thr Leu Ser Thr Asp Asp Arg Glu Ala Ile Ser Lys
                100                 105                 110

Glu Phe Ser Ala Leu Ser Asp Glu Ile Asp Arg Ile Ser Thr Thr Thr
                115                 120                 125

Glu Phe Asn Thr Lys Ser Leu Leu Lys Gly Gly Glu Ser Gly Glu Lys
                130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                165                 170                 175

Lys Leu Glu Glu Ala Gly Asp Glu Glu Lys Val Thr Asn Lys Ala Phe
                180                 185                 190

Thr Asp Asn Thr Asn Leu Lys Tyr Asp Ala Ala Thr Gly Ala Ile Asp
                195                 200                 205

Asn Ser Gly Ser Thr Gly Lys Thr Ala Thr Glu Leu Lys Asp Ala Ile
                210                 215                 220

Thr Asn Ala Ala Asp Asp Thr Ala Lys Ala Ala Gln Lys Ala Tyr
225                 230                 235                 240

Asp Ala Ala Leu Glu Ala Tyr Lys Asn Ser Asp Glu Gly Lys Ala Glu
                245                 250                 255

Leu Lys Ala Ile Ala Asp Glu Asn Thr Ile Ser Lys Ile Asp Asn Ala
                260                 265                 270

Ile Lys Ala Val Ser Ala Gln Arg Ala Asp Leu Gly Ala Ala Gln Asn
                275                 280                 285

Arg Leu Glu His Thr Ile Asn Asn Leu Gly Thr Thr Gln Glu Asn Leu
                290                 295                 300

Ser Glu Ala Asn Ser Arg Ile Arg Asp Val Asp Met Ala Gln Glu Met
305                 310                 315                 320

Met Ser Phe Thr Lys Ser Asn Ile Leu Ser Gln Ala Thr Ser Met
                325                 330                 335

Leu Ala Gln Ala Asn Ser Met Pro Asn Ser Val Leu Ser Leu Leu Gln
                340                 345                 350

<210> SEQ ID NO 40
<211> LENGTH: 352
<212> TYPE: PRT
<213> ORGANISM: Enterococcus gallinarum
<220> FEATURE:
<223> OTHER INFORMATION: Enterococcus gallinarum DSM20628

<400> SEQUENCE: 40

Met Arg Ile Asn Thr Asn Val Ser Ala Leu Asn Thr Tyr Ser Arg Leu
 1               5                  10                  15

Thr Ala Ala Asn Ala Ser Lys Ser Asn Ser Leu Ser Lys Leu Ser Ser
                 20                  25                  30

Gly Met Arg Ile Asn Lys Ala Gly Asp Asp Ala Ala Gly Leu Ala Ile
                 35                  40                  45

Ser Glu Lys Met Lys Gly Gln Ile Gly Gly Leu Ser Gln Ala Lys Ser
                 50                  55                  60

Asn Ala Gln Asp Gly Ile Ser Leu Ile Gln Thr Ala Glu Gly Ala Leu
```

-continued

```
                65                  70                  75                  80
Asn Glu Thr His Ser Ile Leu Gly Arg Met Arg Asp Leu Ala Val Gln
                    85                  90                  95

Ser Ser Asn Gly Thr Leu Ser Thr Asp Asp Arg Glu Ala Ile Ser Lys
                    100                 105                 110

Glu Phe Ser Ala Leu Ser Asp Glu Ile Asp Arg Ile Ser Thr Thr Thr
                    115                 120                 125

Glu Phe Asn Thr Lys Ser Leu Leu Lys Gly Gly Glu Ser Gly Glu Lys
                    130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                    165                 170                 175

Lys Leu Glu Glu Ala Gly Asp Glu Glu Lys Val Thr Asn Lys Ala Phe
                    180                 185                 190

Thr Asp Asn Thr Asn Leu Lys Tyr Asp Ala Ala Thr Gly Ala Ile Asp
                    195                 200                 205

Asn Ser Gly Ser Thr Gly Lys Thr Ala Thr Glu Leu Lys Asp Ala Ile
            210                 215                 220

Thr Asn Ala Ala Asp Asp Thr Ala Lys Ala Ala Ala Gln Lys Ala Tyr
225                 230                 235                 240

Asp Ala Ala Leu Glu Ala Tyr Lys Asn Ser Asp Glu Gly Lys Ala Glu
                    245                 250                 255

Leu Lys Ala Ile Ala Asp Glu Asn Thr Ile Ser Lys Ile Asp Asn Ala
                    260                 265                 270

Ile Lys Ala Val Ser Ala Gln Arg Ala Asp Leu Gly Ala Ala Gln Asn
                    275                 280                 285

Arg Leu Glu His Thr Ile Asn Asn Leu Gly Thr Thr Gln Glu Asn Leu
            290                 295                 300

Ser Glu Ala Asn Ser Arg Ile Arg Asp Val Asp Met Ala Gln Glu Met
305                 310                 315                 320

Met Ser Phe Thr Lys Ser Asn Ile Leu Ser Gln Ala Ala Thr Ser Met
                    325                 330                 335

Leu Ala Gln Ala Asn Ser Met Pro Asn Ser Val Leu Ser Leu Leu Gln
                    340                 345                 350
```

<210> SEQ ID NO 41
<211> LENGTH: 352
<212> TYPE: PRT
<213> ORGANISM: Enterococcus gallinarum
<220> FEATURE:
<223> OTHER INFORMATION: Enterococcus gallinarum NBRC100675

<400> SEQUENCE: 41

```
Met Arg Ile Asn Thr Asn Val Ser Ala Leu Asn Thr Tyr Ser Arg Leu
1               5                   10                  15

Thr Ala Ala Asn Ala Ser Lys Ser Asn Ser Leu Ser Lys Leu Ser Ser
                    20                  25                  30

Gly Met Arg Ile Asn Lys Ala Gly Asp Asp Ala Ala Gly Leu Ala Ile
            35                  40                  45

Ser Glu Lys Met Lys Gly Gln Ile Gly Gly Leu Ser Gln Ala Lys Ser
            50                  55                  60

Asn Ala Gln Asp Gly Ile Ser Leu Ile Gln Thr Ala Glu Gly Ala Leu
65                  70                  75                  80

Asn Glu Thr His Ser Ile Leu Gly Arg Met Arg Asp Leu Ala Val Gln
```

```
                 85                  90                  95

Ser Ser Asn Gly Thr Leu Ser Thr Asp Asp Arg Glu Ala Ile Ser Lys
            100                 105                 110

Glu Phe Ser Ala Leu Ser Asp Glu Ile Asp Arg Ile Ser Thr Thr Thr
        115                 120                 125

Glu Phe Asn Thr Lys Ser Leu Leu Lys Gly Gly Glu Ser Gly Glu Lys
    130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                165                 170                 175

Lys Leu Glu Glu Ala Gly Asp Glu Glu Lys Val Thr Asn Lys Ala Phe
            180                 185                 190

Thr Asp Asn Thr Asn Leu Lys Tyr Asp Ala Ala Thr Gly Ala Ile Asp
        195                 200                 205

Asn Ser Gly Ser Thr Gly Lys Thr Ala Thr Glu Leu Lys Asp Ala Ile
    210                 215                 220

Thr Asn Ala Ala Asp Asp Thr Ala Lys Ala Ala Gln Lys Ala Tyr
225                 230                 235                 240

Asp Ala Ala Leu Glu Ala Tyr Lys Asn Ser Asp Gly Lys Ala Glu
                245                 250                 255

Leu Lys Ala Ile Ala Asp Glu Asn Thr Ile Ser Lys Ile Asp Asn Ala
            260                 265                 270

Ile Lys Ala Val Ser Ala Gln Arg Ala Asp Leu Gly Ala Ala Gln Asn
        275                 280                 285

Arg Leu Glu His Thr Ile Asn Asn Leu Gly Thr Thr Gln Glu Asn Leu
    290                 295                 300

Ser Glu Ala Asn Ser Arg Ile Arg Asp Val Asp Met Ala Gln Glu Met
305                 310                 315                 320

Met Ser Phe Thr Lys Ser Asn Ile Leu Ser Gln Ala Ala Thr Ser Met
                325                 330                 335

Leu Ala Gln Ala Asn Ser Met Pro Asn Ser Val Leu Ser Leu Leu Gln
            340                 345                 350

<210> SEQ ID NO 42
<211> LENGTH: 352
<212> TYPE: PRT
<213> ORGANISM: Enterococcus gallinarum
<220> FEATURE:
<223> OTHER INFORMATION: Enterococcus gallinarum DSM24841

<400> SEQUENCE: 42

Met Arg Ile Asn Thr Asn Val Ser Ala Leu Asn Thr Tyr Ser Arg Leu
1               5                   10                  15

Thr Ala Ala Asn Ala Ser Lys Ser Asn Ser Leu Ser Lys Leu Ser Ser
            20                  25                  30

Gly Met Arg Ile Asn Lys Ala Gly Asp Ala Ala Gly Leu Ala Ile
        35                  40                  45

Ser Glu Lys Met Lys Gly Gln Ile Gly Gly Leu Ser Gln Ala Lys Ser
    50                  55                  60

Asn Ala Gln Asp Gly Ile Ser Leu Ile Gln Thr Ala Glu Gly Ala Leu
65                  70                  75                  80

Asn Glu Thr His Ser Ile Leu Gly Arg Met Arg Asp Leu Ala Val Gln
                85                  90                  95

Ser Ser Asn Gly Thr Leu Ser Thr Asp Asp Arg Glu Ala Ile Ser Lys
```

```
            100                 105                 110
Glu Phe Ser Ala Leu Ser Asp Glu Ile Asp Arg Ile Ser Thr Thr Thr
        115                 120                 125

Glu Phe Asn Thr Lys Ser Leu Leu Lys Gly Gly Glu Ser Gly Glu Lys
    130                 135                 140

Ala Ser Phe Ile Phe Gln Ile Gly Ala Asn Ala Asn Gln Thr Met Ser
145                 150                 155                 160

Val Lys Ile Gly Asp Met Gly Ala Lys Ala Leu Gly Val Asp Ala Leu
                165                 170                 175

Lys Leu Glu Glu Ala Gly Asp Glu Glu Lys Val Thr Asn Lys Ala Phe
            180                 185                 190

Thr Asp Asn Thr Asn Leu Lys Tyr Asp Ala Ala Thr Gly Ala Ile Asp
        195                 200                 205

Asn Ser Gly Ser Thr Gly Lys Thr Ala Thr Glu Leu Lys Asp Ala Ile
    210                 215                 220

Thr Asn Ala Ala Asp Asp Thr Ala Lys Ala Ala Gln Lys Ala Tyr
225                 230                 235                 240

Asp Ala Ala Leu Glu Ala Tyr Lys Asn Ser Asp Gly Lys Ala Glu
                245                 250                 255

Leu Lys Ala Ile Ala Asp Glu Asn Thr Ile Ser Lys Ile Asp Asn Ala
            260                 265                 270

Ile Lys Ala Val Ser Ala Gln Arg Ala Asp Leu Gly Ala Ala Gln Asn
        275                 280                 285

Arg Leu Glu His Thr Ile Asn Asn Leu Gly Thr Thr Gln Glu Asn Leu
    290                 295                 300

Ser Glu Ala Asn Ser Arg Ile Arg Asp Val Asp Met Ala Gln Glu Met
305                 310                 315                 320

Met Ser Phe Thr Lys Ser Asn Ile Leu Ser Gln Ala Ala Thr Ser Met
                325                 330                 335

Leu Ala Gln Ala Asn Ser Met Pro Asn Ser Val Leu Ser Leu Leu Gln
            340                 345                 350

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      DC020 primer

<400> SEQUENCE: 43 cccggggat ccgcggtaaa tgttgctaaa gcatcatcg                          39

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      DC021 primer

<400> SEQUENCE: 44
acgacggtcg acccacagca tcttagggcg tatgcg                            36

<210> SEQ ID NO 45
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      DC047 primer

<400> SEQUENCE: 45
ccaaattaaa gagggttata atgaacgag                                     29

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      DC048 primer

<400> SEQUENCE: 46
gatgcagttt atgcatccct taac                                          24

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      DC013 primer

<400> SEQUENCE: 47
ccgataaata gtagcagagg gaaacc                                        26

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      DC014 primer

<400> SEQUENCE: 48
ggctgaatat ccatcagagc ttcctc                                        26

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 49

His His His His His His
1               5

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Gly Gly
1

<210> SEQ ID NO 51
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 51

Gly Gly Gly Gly Ser
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Gly Gly Gly Gly Ser
1               5

<210> SEQ ID NO 53
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Arg Ile Asn Thr Asn Val Ser Ala Leu Asn Thr Tyr Ser Arg Leu
1               5                   10                  15

Thr Ala Ala Asn Ala Ser Lys Ser Asn Ser Leu Ser Lys Leu Ser Ser
            20                  25                  30

Gly Leu Arg Ile Asn Lys Ala Gly Asp Asp Ala Ala Gly Leu Ala Ile
        35                  40                  45

Ser Glu Lys Met Lys Gly Gln Ile Gly Gly Leu Ser Gln Ala Lys Ser
    50                  55                  60

Asn Ala Gln Asp Gly Ile Ser Leu Ile Gln Thr Ala Glu Gly Ala Leu
65                  70                  75                  80

Asn Glu Thr His Ser Ile Leu Gly Arg Met Arg Asp Leu Ala Val Gln
                85                  90                  95

Ser Ser Asn Gly Thr Leu Ser Asp Asp Arg Ser Ala Ile Asn Lys
            100                 105                 110

Glu Tyr Thr Ala Leu Ser Asp Glu Ile Asp Arg Ile Arg Asp Thr Thr
        115                 120                 125

Glu Phe Asn Thr Lys Ser Leu Leu Thr Gly Glu Gly Asp Asp Ala Lys
    130                 135                 140

Ser Phe Thr Phe Gln Ile Gly Ala Asn Ala Asn Gln Thr Met Ser Val
145                 150                 155                 160

Ser Ile Thr Asn Met Ser Ser Thr Ala Leu Lys Val Lys Gly Leu Asp
                165                 170                 175

Leu Thr Gln Ala Phe Ala Thr Ser Asp Ile Ala Ala Lys Asp Lys
        180                 185                 190

Ala Val Ala Ala Ala Phe Lys Ala Asp Thr Thr Thr Lys Tyr Ala Ala
    195                 200                 205

Asp Gly Lys Val Asp Ala Ala Ala Gly Lys Thr Ala Ala Asp Leu Gln
        210                 215                 220

Thr Ala Ile Asp Thr Ala Ala Asp Ala Ala Lys Ala Thr Ala Gln
225                 230                 235                 240
```

-continued

```
Lys Thr Tyr Asp Asp Ala Leu Ala Thr Phe Thr Ala Ser Asp Glu Gly
            245                 250                 255

Lys Ala Ala Ala Ala Ala Ala Glu Thr Ala Ile Val Glu Asn Asn Pro
            260                 265                 270

Ile Thr Lys Ile Asp Lys Ala Ile Lys Ala Val Ser Ala Gln Arg Ala
            275                 280                 285

Asp Leu Gly Ala Ala Gln Asn Arg Leu Glu His Thr Ile Asn Asn Leu
        290                 295                 300

Gly Thr Thr Gln Glu Asn Leu Ser Glu Ala Asn Ser Arg Ile Arg Asp
305                 310                 315                 320

Val Asp Met Ala Gln Glu Met Met Ser Phe Thr Lys Ser Asn Ile Leu
                325                 330                 335

Ser Gln Ala Ala Thr Ser Met Leu Ala Gln Ala Asn Ser Met Pro Asn
                340                 345                 350

Ser Val Leu Ser Leu Leu Gln Gly
            355             360
```